US007820166B2

(12) United States Patent
Lanzavecchia

(10) Patent No.: US 7,820,166 B2
(45) Date of Patent: Oct. 26, 2010

(54) POTENT T CELL MODULATING MOLECULES

(75) Inventor: Antonio Lanzavecchia, Bellinzona (CH)

(73) Assignee: Micromet AG, Munich (DE)

( * ) Notice: Subject to any disclaimer, the term of this patent is extended or adjusted under 35 U.S.C. 154(b) by 857 days.

(21) Appl. No.: 10/682,845

(22) Filed: Oct. 10, 2003

(65) Prior Publication Data

US 2004/0162411 A1    Aug. 19, 2004

Related U.S. Application Data

(60) Provisional application No. 60/419,149, filed on Oct. 18, 2002.

(30) Foreign Application Priority Data

Oct. 11, 2002    (CA)    ................................ 2403313

(51) Int. Cl.
  *A61K 39/395*    (2006.01)
(52) U.S. Cl. ............... 424/144.1; 424/154.1; 424/156.1
(58) Field of Classification Search .................. None
  See application file for complete search history.

(56) References Cited

U.S. PATENT DOCUMENTS 5,859,205 A * 1/1999 Adair et al. .............. 530/387.3
6,352,694 B1   3/2002 June et al.

FOREIGN PATENT DOCUMENTS

WO    WO 99/54440 A1    10/1999

OTHER PUBLICATIONS

Bortoletto et al., Eur. J. Immunol. 2002. 32: 3102-3107, published online Oct. 16, 2002.by Wiley InterSceince/Eur. J. Immunol.*
Bortoletto et al., Eur. J. Immunol. 2002. 32: 3102-3107, published as a hard copy in the Nov. 2002 issue of the Eur. J. Immunol.*
Janeway et al., Immunobiology, 5th Ed., Garland Science, pp. 94-105 (2001).*
Vajdos et al., J Mol Biol. Jul. 5, 2002;320(2):415-28.*
Rudikoff et al, Proc. Natl. Acad. Sci. USA, 79: 1979-1 983, Mar. 1982.*
Chien et al., Proc Natl Acad Sci U S A. Jul. 1989;86(14):5532-6.*
Alegre et al., J Immunol. Feb. 15, 1991;146(4):1184-91.*
Woodle et al., Transplantation. Sep. 15, 1999;68(5):608-16.*
Colman P. M., Research in Immunology, 145:33-36, 1994.*
Chatenoud et al., Curr Opin Immunol. Dec. 2005;17(6):632-7.*
Schlereth et al., Cancer Immunol Immunother. May 2006;55(5):503-14.*
Portolano et al., J Immunol. Feb. 1, 1993;150(3):880-7.*
Eduardo Padlan, Mol Immunol. Feb. 1994;31(3):169-217.*
Presentation entitled "Enablement Issues in the Examination of Antibodies," presented to the BCP Customer Partnership, Jun. 13, 2007.*
Presentation of Bennett Celsa (Quality Assurance Specialist, TC 1600) entitled "Written Description: Antibodies" presented to the BCP Customer Partnership, Jun. 2, 2009.*

Bachmann et al., "The role of T-cell receptor dimerization in T-cell activation," *Immunology Today*, Dec. 1999, pp. 568-575, vol. 20, No. 12.
Baker et al., "αβ T Cell Receptor Ligan-Specific Oligomerization Revisited," *Immunity* Jun. 2001, pp. 681-693, vol. 14, Cell Press.
Brühl et al., "Depletion of CCR5-Expressing Cells with Bispecific Antibodies and Chemokine Toxins: A New Strategy in the Treatment of Chronic Inflammatory Diseases and HIV," *The Journal of Immunology*, 2001, pp. 2420-2426, vol. 166, The American Association of Immunologists.
Davis et al., "Ligand Recognition by αβT Cell Receptors," *Annu. Rev. Immunol.*, 1998, pp. 523-544, vol. 16, Annual Reviews.
Ding et al., "Four A6-TCR/Peptide/HLA-A2 Structures that Generate Very Different T Cell Signals Are Nearly Identical," *Immunity*, Jul. 1999, pp. 45-56, vol. 11, Cell Press.
Garcia et al., "CD8 enchances formation of stable T-cell receptor/MHC class I molecule complexes," *Nature*, Dec. 12, 1996, pp. 577-581, vol. 384.
Germain et al., "The Dynamics of T Cell Receptor Signaling: Complex Orchestration and the Key Roles of Tempo and Cooperation," *Annu. Rev. Immunol.*, 1999, pp. 467-522, vol. 17.
Janeway, Jr., "Ligands for the T-cell receptor: hard times for avidity models," *Immunology Today*, 1995, pp. 223-225, vol. 16, No. 5.
Kipriyanov et al., "Bispecific Tandem Diabody for Tumor Therapy with Improved Antigen Binding and Pharmacokinetics," *J. Mol. Biol.*, 1999, pp. 41-56, vol. 293, Academic Press.
Kufer et al., "Construction and biological activity of a recombinant bispecific single-chain antibody designed for therapy of minimal residual colorectal cancer," *Cancer Immunol. Immunother.*, 1997, pp. 193-197, vol. 45, Springer-Verlag.
Löffler et al., "A recombinant bispecific single-chain antibody, CD19 X CD3, induces rapid and high lymphoma-directed cytotoxicity by unstimulated T lymphocytes," *Blood*, Mar. 15, 2000, pp. 2098-2103, vol. 95, No. 6.
Mack et al., "A small bispecific antibody construct expressed as a functional single-chain molecule with high tumor cell cytotoxicity," *Proc. Natl. Acad. Sci. USA*, Jul. 1995, pp. 7021-7025, vol. 92.
Mack et al., "Biologic Properties of a Bispecific Single-Chain Antibody Directed Against 17-1A (EpCAM) and CD3," *The Journal of Immunology*, 1997, pp. 3965-3970, vol. 158.

(Continued)

*Primary Examiner*—Zachary Skelding
(74) *Attorney, Agent, or Firm*—Foley & Lardner LLP

(57) ABSTRACT

The present invention relates to a polypeptide construct comprising at least one CDR3 region, wherein at least one of the at least CDR3 regions comprises at least one substitution in the amino acid sequence YYDDHY (SEQ ID NO.1) and wherein the at least one substitution comprises: in the first position of SEQ ID NO.1 a substitution from Y to H; in the second position of SEQ ID NO. 1 a substitution from Y to S, from Y to N, from Y to F or from Y to H; in third position of SEQ ID NO. 1 a substitution from D to N or from D to E; in the forth position of SEQ ID NO. 1 a substitution from D to Q, from D to A, from D to V, from D to E or from D to G; in the fifth position of SEQ ID NO. 1 a substitution from H to Q, from H to P, from H to Y, from H to R or from H to N; or in the sixth position a substitution from Y to N.

30 Claims, 4 Drawing Sheets

OTHER PUBLICATIONS

Matsui et al., "Low Affinity Interaction of Peptide-MHC Complexes with T Cell Receptors," *Science*, Dec. 20, 1991, pp. 1788-1791, vol. 254.

Sykulev et al., "Kinetics and Affinity of Reactions between an Antigen-Specific T Cell Receptor and Peptide-MHC Complexes," *Immunity*, Apr. 1994, pp. 15-22, vol. 1, Cell Press.

Sykulev et al., "Evidence that a Single Peptid-MHC Complex on a Target Cell Can Elicit a Cytolytic T Cell Response," *Immunity*, Jun. 1996, pp. 565-571, vol. 4, Cell Press.

Vailtutti et al., "Serial triggering of many T-cell receptors by a few peptide-MHC complexes," *Nature*, May 11, 1995, pp. 148-151, vol. 375.

van der Merwe et al., "Cytoskeletal polarization and redistribution of cell-surface molecules during T cell antigen recognition," *Seminars in Immunology*, 2000, pp. 5-21, vol. 12.

Lanzavecchia et al., "From TCR Engagement to T Cell Activation: A Kinetic View of T Cell Behavior," *Cell*, Jan. 8, 1999, pp. 1-4, vol. 96.

\* cited by examiner

POTENT T CELL MODULATING MOLECULES

This application claims priority to Canadian Application 2,403,313 filed Oct. 11, 2002 and U.S. Provisional Application 60/419,149 filed Oct. 18, 2002.

BACKGROUND OF THE INVENTION

The present invention relates to a polypeptide construct comprising at least one CDR3 region, wherein at least one of said at least CDR3 regions comprises at least one substitution in the amino acid sequence YYDDHY (SEQ ID NO.1) and wherein said at least one substitution comprises: in the first position of SEQ ID NO:1 a substitution from Y to H; in the second position of SEQ ID NO. 1 a substitution from Y to S, from Y to N, from Y to F or from Y to H; in third position of SEQ ID NO. 1 a substitution from D to N or from D to E; in the forth position of SEQ ID NO. 1 a substitution from D to Q, from D to A, from D to V, from D to E or from D to G; in the fifth position of SEQ ID NO. 1 a substitution from H to Q, from H to P, from H to Y, from H to R or from H to N; or in the sixth position a substitution from Y to N.

Furthermore, the invention provides for polynucleotides encoding said polypeptides as well as for vectors and host cells comprising said polynucleotides. Additionally, the invention relates to compositions, preferably pharmaceutical or diagnostic compositions comprising the polypeptides, polynucleotides, vectors or host cells of the invention.

Several documents are cited throughout the text of this specification. Each of the documents cited herein (including any manufacturer's specifications, instructions, etc.) are hereby incorporated by reference.

T cells are a major population of lymphocytes. These cells express a unique membrane bound antigen-binding molecule, the T-cell receptor (TCR). The T-cell receptor associates with the cluster of differentiation "CD3", forming the TCR-CD3 membrane complex.

Despite advances in understanding how T cells are activated (Davis, 1998, Annu. Rev. Immunol. 16, 523-44) and how the T cell signal is propagated within the cell (Germain, 1999, Annu. Rev. Immunol. 17, 467-522), few details are known of the mechanism by which engagement of a TCR by its ligand results in signaling.

A number of models have been proposed concerning the mechanism of T-cell activation and signal transduction (Davis, 1998, Annu. Rev. Immunol. 16, 523-44; Baker 2001, Immunity 14, 681-692). These include oligomerization of TCR-peptide/MHC complexes (Bachmann, 1999, Immunol. Today 20, 568-576), serial triggering (Vallitutti, 1995, Nature 375, 148-151; Viola, 1999, Cell 96, 1-4), conformational changes occurring within a single TCR heterodimer (Janeway, 1995, Immunol. Today 16, 223-225), geometrical rearrangements within a multivalent TCR/CD3 complex (Ding, 1999, Immunity 11, 45-56), and segregation of kinase and phosphatases due to varying sizes of extracellular domains (van der Merwe, 2000, Semin. Immunol. 12, 5-21). In each model, the molecular event (e.g. oligomerization or conformational change) is presumed to alter the degree of phosphorylation on the cytoplasmic side of the membrane in favor of signal transduction.

When defined oligomers of MHC class II-peptide complexes were used to trigger T cells, it was found that at least three TCRs need to be brought together in order to induce a calcium response (Boniface, 1998, Immunity 9, 459-466). In another study T cell activation could be induced either by dimers of MHC class I-peptide complexes or by monomers that cross-link the TCR with the CD8 coreceptor-Lck kinase complex (Delon, 1998, Science 281, 572-575).

The serial triggering model proposes that a small number of peptide/MHC complexes can cause activation by transiently binding many TCRs (Viola, 1996, loc. cit.). The actual measurements have been difficult, however, partly because the membrane-bound nature of MHC molecules and TCRs required the engineering of soluble forms, partly because the affinities are only measurable with highly sensitive technology.

The first measurements of TCR affinities for peptide/MHC complexes were made by Matsui 1991, Science 254, 1788-1791 and Weber 1992, Nature 356, 793-796, which showed low affinity binding $K_D \sim 10\text{-}50\,\mu M$. Later experiments (Sykulev 1994, Immunity 1, 15-22; Sykulev 1996, Immunity 4, 565-571) used a different experimental approach and showed higher affinities $K_D \sim 0.1\,\mu M$.

Recently the development of surface plasmon resonance instruments, particularly the BIAcore™ (Pharmacia Biosensor) allowed measuring the kinetics of TCR binding to the peptide/MHC complex. In some cases the fast off-rate measured was significantly stabilized if soluble CD8 was introduced (Garcia 1996, Nature 384, 577-81). This indicates that T cell activation might involve the interaction of additional components like CD8 with the peptide/MHC complex, although recognition of the peptide/MHC complex is mediated solely by the TCR-CD3 complex.

The TCR-peptide/MHC complex interaction as well as the interaction of additional T cell components with the peptide/MHC complex may require an optimal dwell time (Kalergis 2001, Nature Immunol. 2, 229-234; Viola 1996, loc. cit.) and may have an effect upon the kinetics of T cell activation. Half lives for the interaction complexes were measured between 10-30 sec (Davis 1998, loc. cit.).

In contrast, data on dissociation rates measured by BIAcore™ do not support the serial triggering model (Davis 1998, loc. cit.). This is because, thus far, all improvements in TCR/peptide/MHC complex stability within any one system result in a more robust T cell response (Davis et al. 1998, Annu. Rev. Immunol. 16, 523-44) rather than exhibiting a normal distribution around some optimum value as proposed (Kalergis 2001, Nature Immunol. 2, 229-234). In summary, it has to be emphasized that to date, the data from TCR-peptide/MHC interactions available in the literature do not preferentially support any one T cell activation model.

It has been known since the early 1980s that T cell activation can also be induced by anti-TCR antibodies. Recent data on antibody-induced T cell activation have provided support for oligomerization of TCRs upon ligand contact (Reich 1997, Nature 387, 617-20; Brown 1993, Nature 364, 33-39), although there are dissenting views.

Some experiments have used bispecific reagents for T cell targeting (Traunecker 1991, Embo J. 10, 3655-3659; Mack 1995, PNAS 92, 7021-7025; Mack 1997, J. Immunol. 158, 3965-3970). Bispecific antibodies can be used for the binding to the TCR/CD3 complex and to a cell surface antigen to target cytotoxic T lymphocytes against a target of choice (Staerz 1985, Nature 314, 628-631; Lanzavecchia 1987, Eur. J. Immunol. 17, 105-111). The monovalent binding to CD3 does not result in T cell activation. Therefore, bispecific antibodies have been used to arm in vitro polyclonal CTL populations that have been subsequently reinfused into tumor patients (Roosnek 1989, J. Exp. Med. 170, 297-302; Bolhuis 1992, Int. J. Cancer Suppl. 7, 78-81). For this "T cell arming" approach a high affinity binding to CD3 is absolutely required so that the T cells can retain the bispecific molecule on their surface until they have a chance to interact with tumor cells.

However, these results can not be generalized. In different experimental settings different binding affinities might be measured.

It has to be especially emphasized that the data on T cell activation generated from TCR-peptide/MHC complexes cannot be transferred to the situation of an antibody-induced T cell activation. In the artificial situation of an antibody-induced T cell activation, the kinetics of the process may be completely different from the kinetics during the natural TCR-peptide/MHC interaction, since for example one of the major components, the peptide/MHC complex, is not present. Consequently, the kinetics are no longer determined by the TCR-peptide/MHC interaction or by the interaction of additional components like CD8 with the peptide/MHC complex.

Therefore, the available TCR-peptide/MHC T cell activation data cannot be applied to the mechanism of an antibody-induced T cell activation nor the T cell activation mechanism induced by any other biosynthetic molecule.

The CD3 complex denotes an antigen that is expressed on T-cells as part of the multimolecular T-cell receptor complex. It consists of several different chains for instance γ, δ, ε, ζ. or/and η chains. Clustering of CD3 on T cells, e.g., by immobilized anti-CD3-antibodies, leads to T cell activation similar to the engagement of the T cell receptor but independent from its clone typical specificity. Actually, most anti-CD3-antibodies recognize the CD3ε-chain.

Prior art has exemplified T cell activation events employing antibody molecules. For example, U.S. Pat. No. 4,361,544 proposes a hybrid cell line for the production of monoclonal antibody to an antigen found on normal human T cells and cutaneous T lymphoma cells and defines the antibody produced as "OKT3". In U.S. Pat. No. 5,885,573 the murine OKT3 (described in U.S. Pat. No. 4,361,549) has been transferred into a human antibody framework in order to reduce its immunogenicity. Furthermore, U.S. Pat. No. 5,885,573 discloses specific mutations in the FcR-binding segment of OKT-3 which leads to a Glu at position 235, a Phe at position 234 or a Leu at position 234, i.e. to specific mutations in the CH2 region which are supposed to result in modified binding affinities for human FcR. In proliferation assays or in assays relating to the release of cytokines, the mutated OKT-3 antibodies disclosed in.

U.S. Pat. No. 5,885,573 appear to result in comparable cell proliferations to that observed with PBMC stimulated with the original murine OKT3 and to similar amounts of cytokines produced. Merely the mutated Glu-235 mAb induced smaller quantities of TNF-α and GM-CSF and no IFN-γ. No T cell proliferation was induced by Glu-235 mab using PBMC from three different donors at mab concentrations up to 10 μg/ml, suggesting that the alteration of the FcR binding region of this mab had impaired its mitogenic properties. T cell activation by Glu-235 mab also resulted in lower levels of expression of surface markers Leu23 and IL-2 receptor. U.S. Pat. No. 5,929,212 discloses a recombinant antibody molecule in which the binding regions have been derived from the heavy and/or light chain variable regions of a murine anti-CD3 antibody, e.g. OKT3, and have been grafted into a human framework. Similarly, U.S. Pat. No. 5,885,573 discloses the transfer of binding specificity from OKT3 into a human framework. WO 98/52975 discloses a mutated variant of the murine anti-CD3 antibody OKT3. The mutated OKT3 antibody is produced using a recombinant expression system and WO 98/52975 proposes that the mutated anti-CD3 antibody is more stable than the parental OKT3 protein during extended storage periods. U.S. Pat. No. 5,955,358 discloses a method of shuffling, at the DNA level, multiple CDR domains, either from the same or different antibodies, meaning that their order within antibody variable domains is altered to yield new combinations of binding regions.

As mentioned above, the OKT3 antibody is a mouse anti-human CD3 monoclonal antibody (mAb), derived from the murine hybridoma OKT3. It recognizes an epitope on the epsilon subunit of the human CD3 complex. OKT3 was originally described in U.S. Pat. No. 4,361,544 and U.S. Pat. No. 4,658,019; Kung 1979, Science 206, 347-349; Van Wauwe 1980, J. Immunol. 124, 2708-2713; Transy 1989, Eur. J. Immunol. 19, 947-950. Since then, OKT3 has been used as potent immunosuppressive agent in clinical transplantation to treat allograft rejection (Thistlethwaite 1984, Transplantation 38, 695-701; Woodle 1991, Transplantation 51, 1207-1212; Choi 2001, Eur. J. Immunol. 31(1), 94-106). Major drawbacks of this therapy are T cell activation manifested in cytokine release due to cross-linking between T cells and FcgammaR-bearing cells and the human anti-mouse antibody (HAMA) response. Several publications have described alterations like humanization of OKT3 to reduce those side effects: U.S. Pat. No. 5,929,212; U.S. Pat. No. 5,885,573 and others. On the other hand, OKT3 or other anti-CD3-antibodies can be used as immunopotentiating agents to stimulate T cell activation and proliferation (U.S. Pat. No. 6,406,696 Bluestone; U.S. Pat. No. 6,143,297 Bluestone; U.S. Pat. No. 6,113,901 Bluestone; Yannelly 1990, J. Immunol. Meth. 1, 91-100). Anti-CD3-antibodies have also been described as agents used in combination with anti-CD28-antibodies to induce T cell proliferation (U.S. Pat. No. 6,352,694).

OKT3 has further been used by itself or as a component of a bispecific antibody to target cytotoxic T cells to tumor cells or virus infected cells (Nitta 1990, Lancet 335, 368-376; Sanna 1995, Bio/Technology 13, 1221-1224; WO 99/54440). Approaches up to now using antibodies as agents for recruiting T-cells have been hampered by several findings. First, natural or engineered antibodies having a high binding affinity to T-cells often do not activate the T-cells to which they are bound. Second, natural or engineered antibodies having a low binding affinity to T-cells are also often ineffective with respect to their ability to trigger T-cell mediated cell lysis.

A recently described novel approach to stimulate and/or modify T-cell response, in particular in human patients, comprise the use of single chain antibody constructs as well as bispecific molecules/bispecific antibody molecules. Such molecules and approaches are described in WO 99/54440, Mack, J. Immunol. (1997), 158, 3965-3970, Mack, PNAS, (1995), 92, 7021-7025, Kufer, Cancer Immunol. Immunother., (1997), 45, 193-197, Löffler, Blood, (2000), 95, 6, 2098-2103, Brühl, Immunol., (2001), 166, 2420-2426, Kipriyanov, J. Mol. Biol., (1999), 293, 41-56.

Antibody constructs, in particular single chain constructs and/or constructs of a bispecific formate, triggering T cell activation in the presence of a target cell are highly potent molecules in treatment of tumorous diseases, autoimmune diseases, inflammatory and infectious diseases. Such constructs are described, inter alia in WO 99/54440, wherein T-cell activation is mediated via anti-CD3 part of such antibody constructs. Bispecific single chain antibody constructs are activating T-cells only in presence of a specific target cell leading to a cytotoxic activity on the target cells. T-cell activation relates to expression of numerous genes, in particular genes encoding cytokines like IFNy, IL-2, IL-3, TGF-β, TNF-β, IL4, IL5, IL6 and GM-CSF (see Kuby, Immunology 4th edition, p. 249). It is also known that therapeutic application of antibody constructs as described in the prior art with strong T-cell activating capacity as described in the prior art also induce a strong release of cytokines.

Cancer and especially autoimmune diseases are known to be associated with release of different cytokines. Release of sIL-2R, IL-4, IL-6, IL-8, IL-10, IL-12 and TNF-alpha was shown in patients with various autoimmune disturbances such as persistent neutropenia, immune thrombocytopenia, pure red-cell aplasia, Hashimoto's thyroiditis, sicca syndrome, systemic lupus erythemathosus, systemic scleroderma (Shvidel, Hematol J. 2002, 3, 32-7). For these reasons, antibody therapy employing, inter alia, single chain constructs in patients with autoimmune diseases should not induce a further increase of the level of pro-inflammatory cytokines.

In patients with immunogenic tumors like malign melanoma or kidney cell carcinoma very few spontaneously occurring T-cells directed against tumor cells are found. The tumor specific immune response observed in patients suffering from these diseases is not sufficient to reduce or eliminate the tumor. Accordingly, it is desired to establish a therapeutic approach which leads to a reduction or elimination of the tumor without inducing severe side effects, like increased expression of soluble cytokines. Accordingly, in these patients it is desired to enhance the antigen specific immune response via activating of (an) already existing small sub-population(s) of T-cells specific for a tumor antigen. A similar situation is observed in patients with virus infections without spontaneous recovery, for example in chronic hepatitis (like hepatitis C). Endogenous virus-specific T-cell immunity exists but is not sufficient to control the virus infection. In these cases an enhancement of this low antigen-specific T-cell response would be desirable.

Accordingly, in certain medical settings, selective and modified activation of endogenous antigen-specific T-cell population(s) is desired.

Therefore, the technical problem underlying the present invention was to provide for means and methods for pharmaceutical intervention of disorders where selective and/or modified activation of specific T-cell populations is desired and wherein the endogenous immune response of the patient to be treated has to be modified, selectively enhanced and/or "fine-tuned". The solution to said technical problem is achieved by providing the embodiments characterized in the claims.

SUMMARY OF THE INVENTION

Accordingly, the present invention provides for a polypeptide construct comprising at least one CDR3 region, wherein at least one of said at least one CDR3 regions comprises at least one substitution in the amino acid sequence YYDDHY (SEQ ID NO:1) and wherein said at least one substitution comprises:

in the first position of SEQ ID NO.1 a substitution from Y to H;

in the second position of SEQ ID NO. 1 a substitution from Y to S, from Y to N, from Y to F or from Y to H;

in third position of SEQ ID NO. 1 a substitution from D to N or from D to E;

in the forth position of SEQ ID NO. 1 a substitution from D to Q, from D to A; from D to V, from D to E or from D to G;

in the fifth position of SEQ ID NO. 1 a substitution from H to Q, from H to P, from H to Y, from H to R or from H to N; or in the sixth position a substitution from Y to N.

Kato-3 (A) and peripheral blood T cells (B) were incubated with wildtype (WT) or mutant (M13, M76) bispecific antibodies followed by and anti-HIS6 mAb and PE-conjugated goat anti-mouse Ig. (C) Geometric mean fluorescence data.

Figure 2:
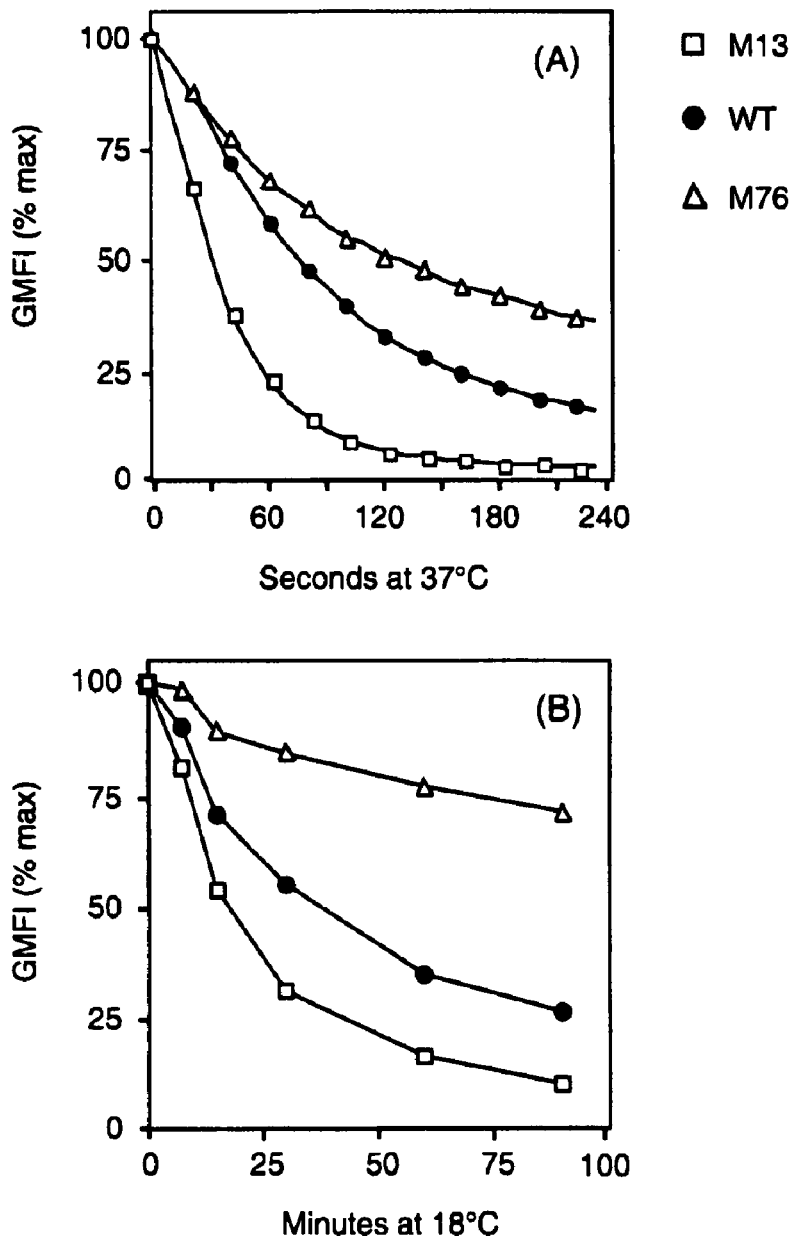

FIG. 2. Dissociation kinetics of wildtype and CD3 mutant bispecific antibodies from T cells.

T cells were incubated at 4° C. with bispecific antibodies followed by anti HIS6 mAb and PE-conjugated goat anti-mouse Ig. Dissociation was measured at 37° C. (A) and 18° C. (B) in the presence of azide and an excess of soluble anti-CD3 monoclonal antibodies to prevent rebinding. Dissociation from Kato-3 cells was comparable for WT and mutants. Wildtype (filled circles), M13 (empty squares), M76 (empty triangles).

Figure 3:
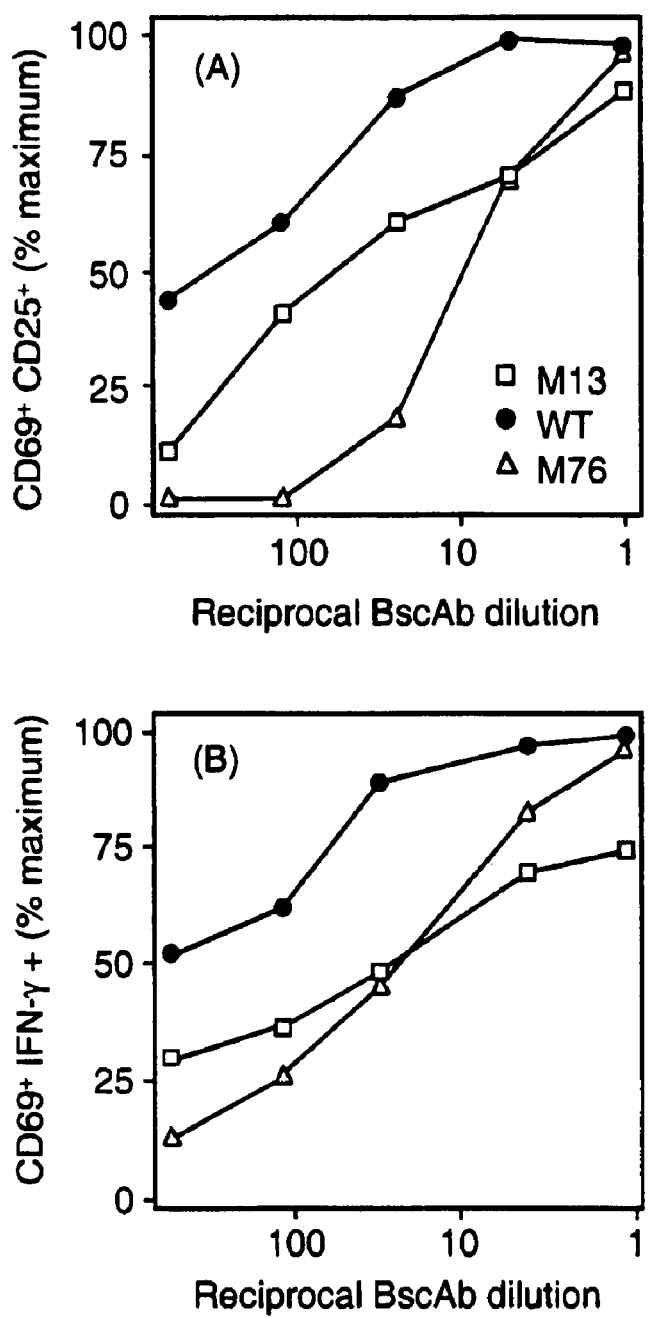

FIG. 3. Efficient T cell activation by low doses low affinity bispecific antibodies.

Kato-3 cells were pulsed with serial dilutions of WT and CD3 mutant bispecific antibodies starting from concentrations that give the same level of staining. Cells pulsed with bispecific antibodies were incubated with naïve CD4+ T cells (A) or T cell blasts (B). (A) CD69+ CD25+ T cells after 20 hours and (B) CD69+ IFN-γ+ T cells after 6 hrs.

Figure 4:
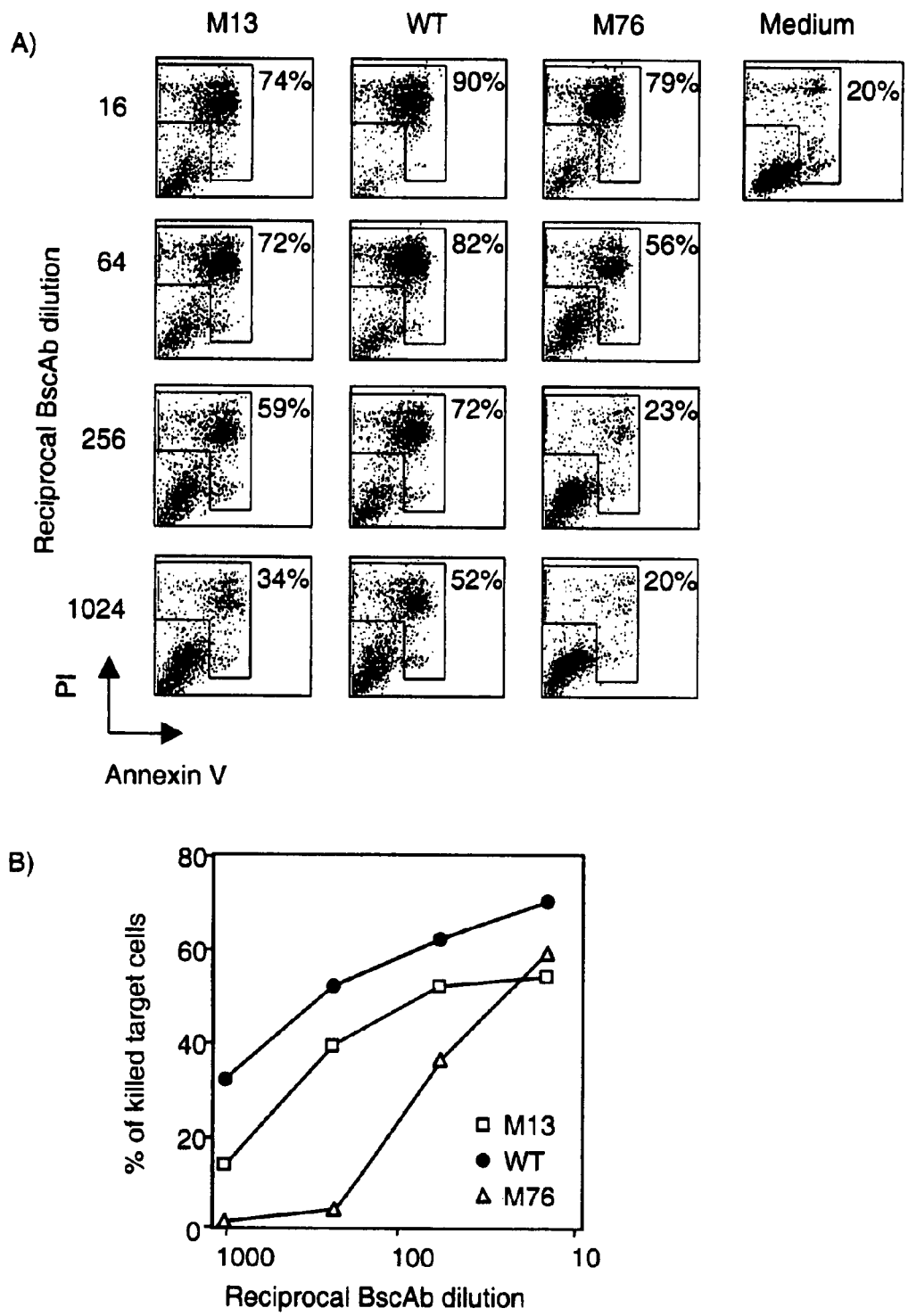

FIG. 4. Efficient CTL targeting by low affinity bispecific antibodies.

Kato-3 cells were pulsed with serial dilution of bispecific antibodies as in FIG. 3, washed and incubated with influenza-specific CTL clone. Killing was measured after 5 hours by staining Kato-3 cells with Annexin V and propidium iodide. (A) Dot plot analysis; (B) percent tumour cells killed.

DETAILED DESCRIPTION OF THE INVENTION

In accordance with the present invention it was surprisingly found that a CDR3 region of an antibody molecule, preferably directed against the CD3 on the surface of a T-cell, may be specifically modified/mutated. This specific modification(s)/mutation(s) as disclosed herein provide(s) for modified antibody molecules or antibody constructs as disclosed herein with altered physiological and/or biochemical activities. Accordingly, the present invention provides for molecules or polypeptide constructs which are preferably capable of interacting with/binding to CD3 of T-cells, whereby the modified constructs as disclosed herein are capable of activating T-cell(s). Therefore, the present invention provides for antibodies and/or polypeptide constructs which, on one hand preferably bind to CD3 and, on the other hand, are able to activate specifically T-cells, whereby said T-cell activation may be chosen to be "low", "moderate" or "high" as will be defined herein below.

In accordance with the present invention, the term "polypeptide construct" relates to, in its broadest sense, any polypeptide comprising at least one CDR3-region as defined herein. It is preferred that said "polypeptide construct" is an antibody construct, whereby said antibody construct may comprise single chain constructs, bispecific constructs, Fab-fragments, F(ab')2-fragments, scFvs, bispecific scFv, antibody fusion proteins or antibody-antigen-constructs as defined herein below. These antibody constructs may also comprise antibodies or antibody fragments as defined herein which comprise further effector domains, like toxins or radioisotopes. In a particular preferred embodiment of the invention, the polypeptide construct is a bispecific single chain construct, e.g. a bispecific scFv as described in the appended examples. Most preferably, the polypeptide construct of the invention is a bispecific single chain construct with two binding affinities wherein at least one of these binding affinities comprise a CDR-3 region wherein, in accordance with the invention, the YYDDHY-motif has been modified/substituted as disclosed herein. In a preferred embodiment of the invention said polypeptide construct of the invention is capable of triggering the activation of T-cells in presence of target cells (i.e. cells expressing specific molecules, preferably on their cell surface, like receptors, antibodies, membrane proteins or molecules which are to be secreted) and does not provide for a general activation of T-cells.

Preferably, the polypeptide construct of the present invention consists of at least two domains, wherein one of said at least two domains is capable of interacting with/binding to T-cells. Most preferably said domain interacts with/binds to CD3 of T-cells. It is also envisaged that the polypeptide construct comprises more than two functional domains, i.e. at least three, at least four or at least five functional domains. Polypeptide constructs comprising several functional domains are known in the art an, inter alia, described in WO 00/06605. It is of particular note that in a polypeptide construct of the invention (which is in the format a molecule and which comprises two domains as defined herein) at least one domain comprises the CDR-3 region comprising the modified YYDDHY-motif as disclosed herein and wherein the second domain is, inter alia, binding molecule/part of a binding molecule or an antigen/antigen part which is capable to interact with/binding to another specific moiety. In a preferred embodiment, the first and second binding domains are covalently connected to one another as a single chain. This connection can be effected either directly (domain1-domain2) or through an additional polypeptide linker sequence (domain1-linker sequence-domain2). In the event that a linker is used, this linker is preferably of a length and sequence sufficient to ensure that each of the first and second domains can, independently from one another, retain their differential binding specificities. In the event that such a bispecific single chain Fv is used, the modification may be performed in one domain so that the resulting bispecific single chain Fv contains the biosynthetic polypeptide in the domain in which the modification was performed. The resulting bispecific single chain Fv which comprises one domain comprising the CDR-3 region with modified YYDDHY-motif according to the invention, is one example of what is termed "polypeptide construct" according to the invention.

The term "CDR-3 region" as used herein denotes the "Complementary determining region 3" of an antibody molecule. Most preferably said CDR-3 region is the CDR-3 region of an antibody directed against the CD3 of a T-cell. Most preferably said CDR-3 region comprised in the inventive polypeptide construct is derived or is the CDR-3 region of the $V_H$-region of the OKT-3 antibody, whereby in accordance with this invention, the comprised amino acid sequence YYDDHY (SEQ ID NO: 1) is modified by substitution as described herein. It is envisaged that the polypeptide construct of the present invention does not only comprise a CDR-3 region, but also comprises (a) CDR-1 or CDR-2 region(s) of antibodies. Most preferably, the polypeptide construct of the invention comprises a modified CDR-3 region as defined herein (i.e. a CDR-3 region wherein the sequence YYDDHY (SEQ ID NO: 1) comprises at least one substitution as disclosed herein) and comprises in addition at least one further CDR-1 region and at least one further CDR-2 region. In a most preferred embodiment, said CDR-1 and regions and in particular said modified CDR-3 regions comprised in the polypeptide construct of the invention are the CDR-regions of the $V_H$-part of an antibody. Yet, as also illustrated herein below and in the appended examples, the polypeptide constructs of the present invention may comprise a plurality (at least two) CDR-3 regions, CDR-2 regions and/or CDR-1 regions. Accordingly, the polypeptide construct of the invention may comprise CDR-1, CDR-2, CDR-3 region of $V_L$ as well as CDR-1, CDR-2, CDR-3 region of $V_H$ of a given antibody or antibody fragment or antibody derivative. It is most preferred that the CDR-regions of $V_L$ and $V_H$ of OKT-3 is employed in accordance with this invention, wherein the CDR-3 region of $V_H$ of OKT-3 comprises at least one of the substitutions in the YYDDHY-motif as disclosed herein. Therefore, it is envisaged that the polypeptide construct of the invention comprises at least one CDR-3 region with the modified YYDDHY-motif as described, wherein said CDR-3 region is derived from the $V_H$ region of OKT-3. It is most preferred that said modified CDR-3 region of OKT-3, is combined with CDR-1 and CDR-2 regions of OKT-3, but it is also envisaged that said modified CDR-3 region is combined with CDR-1 and/or CDR-2 regions derived from other antibody molecules, like further antibodies directed against. CD3 of T-cells, preferably of human T-cells. These "further antibodies" comprise, inter alia, antibodies as described in Parren (1991), Res. 1 mm. 142, 749-763 or Cole (1999), Transplantation 68, 563-571, UCHT-1 (Ceuppens, Cell. Immunol. 1986, 102(1), 144-51; Yeh, Placenta 1990, 11(3), 253-61), Leu4 (Yeh, Placenta 1990, 11(3), 253-61), SPV-T3b (Parsey J Immunol 1993, 151(4), 1881-93) or WT31 and WT32 (Tax, Nature 1983, 304(5925), 445-447).

Most preferably, the polypeptide construct of the invention also comprises a $V_L$-region (with the corresponding CDR-1, CDR-2, CDR-3 regions) and comprises besides the modified CDR-3 region of the $V_H$-part the CDR-1 and CDR-2 region said $V_H$-part of said antibody. In a most preferred embodiment, as shown herein below, the polypeptide construct of the invention specifically binds to/interacts with the "third cluster of differentiation (CD3)-protein" of a T-cell. Said interaction/binding may be an in vitro as well as an in vivo binding/interaction. Furthermore, said binding/interaction may occur when CD3 is bound to the surface of a T-cell but it is also envisaged that the polypeptide construct of the invention is capable of interacting with isolated and/or recombinant CD3.

Accordingly, the present invention relates to polypeptide constructs wherein the CDR3 region of, preferably, the anti-CD3 heavy chain sequence of an antibody is modified in accordance with the stipulations of the present invention, i.e. wherein the CDR-3 region, preferably of $V_H$, comprises at least one substitution as defined herein above.

Amino acids, in accordance with the invention are mostly described in the "one-letter code". Accordingly,

| | |
|---|---|
| Y | represents tyrosine (Tyr), |
| D | represents aspartic acid (Asp), |
| H | represents histidine (His), |
| S | represents serine (Ser), |
| N | represents asparagine (Asn), |
| E | represents glutamic acid (Glu), |
| Q | represents glutamine (Gln), and |
| R | represents arginine (Arg). |

Furthermore, said "one-letter code", as well as the "three-letter code" used herein and in the appended sequence listing follows IUPAC.

As pointed out above and illustrated in the examples, the polypeptide construct of the invention is preferably a construct, wherein said polypeptide construct is (a) capable of specifically binding to/interacting with the CD3 of a T-cell and/or (b) of activating a T-cell.

It is preferred that said activation of a T-cell comprises the upregulation of expression of cell surface proteins CD69, CD2, LFA-1, VLA-4 and/or CD25, the upregulation of expression of interferon gamma, the, upregulation of expression of IL-2, IL-12, IL-15 or IL-18, an increased cytotoxicity and/or an increased mitotic activity as compared to a non-activated T-cell. It is of note that a naïve immune lymphocyte is not able to mount an immune response until it has been activated to become an effector cell. Antigen presentation to the naïve lymphocyte results in its activation, as illustrated in Kuby, Immunology, 4$^{th}$ edition, p. 377.

One of skill in the art will, however, recognize that there are many indicators of an increased T-cell activity and that, accordingly, the above illustrative examples do not represent a complete list of modes by which T-cell activation can be measured. Thus, it is possible that the measurement of other factors than those noted above will also suffice as an indication of T-cell activation within the meaning of the invention.

Ultimately, T-cell activation will preferably manifest itself in an increased cytotoxicity against other target cells, the lysis of which might contribute to or even constitute a successful therapeutic regimen. One of skill in the art will appreciate that there exist numerous methods of determining whether and to what extent a target cell population has been depleted. Such methods include, but are not limited to measurement of bioactivity (in general all assays based on release of a loaded substance or on reduction of cell proliferation) like measurement of $^{51}$Cr-release (as described, inter alia, in Mack (1995) PNAs 92, 7021-7025), monitoring a heterogeneous cell population containing the target cells to be depleted by Fluorescence Activated Cell Sorting (FACS) with and without calcein labeling of the target cell, monitoring of fluorochrome release based assay, measurement of LDH release, measurement of WST-1 cell viability according to the manufacturer's protocol (Roche Diagnostics), measurements of proliferation assays p.e. MTT assay, XTT assay, measurement of $^{3}$H thymidine uptake or bromine deoxyuridine (BrdU) uptake. $EC_{50}$ values were measured according to the methods known in the art and were determined as follows:

| | |
|---|---|
| high activity: | $\leq$/–10 ng/ml, preferably 1 ng/ml, most preferably 0.1 ng/ml |
| low activity: | >10 ng/ml. |

In context of this invention, it is noted that $EC_{50}$ values may be determined according to the methods known in the art: a standard dose-response curve is defined by four parameters: the baseline response (Bottom), the maximum response (Top), the slope, and the drug concentration that provokes a response halfway between baseline and maximum ($EC_{50}$). $EC_{50}$ is defined as the concentration of a drug or molecule that provokes a response half way between the baseline (Bottom) and maximum response (Top).

The percentage of cell lysis could be determined by, inter alia, release assays disclosed herein above, for example, $^{51}$Cr release assays, LDH-release assays, and fluorochrome release assays, and the like. Accordingly, in this invention, a cell lysis of >/–30% (greater or equal 30%), preferably 50-60%, and most preferably 80-90% represents strong cytotoxic activity, whereas a cell lysis of <30% (less than 30%) represents weak cytotoxic activity.

Accordingly, in context of this invention high activity in T-cell activation relates to a molecule comprising EC values </–10 ng/ml and/or a percentage of cell lysis of >/–30%. Yet, T-cell activity may also be determined by measuring the induction of specific activation markers, like CD69, CD25 or IFN-γ and the like. As shown in the appended examples, the induction of CD69, IFN-γ and/or CD25 upregulation may be measured by FACS analysis. In accordance with this experimental setting a high activation of T-cells (+++ or ++) corresponds to an upregulation of CD69, CD25 and/or IFN-γ expression, whereby $\geq$25%, most preferably $\geq$35% of cells express these molecules at a 1/100 dilution of the polypeptide constructs of the invention, more preferably of bispecific polypeptide constructs, even more preferably of a bispecific antibody as described herein. A low activation (0 or +) corresponds to less then (<)25% of cells expressing CD69, CD25 and/or IFNγ of a 1/100 dilution of the polypeptide constructs of the invention, more preferably of bispecific polypeptide constructs, even more preferably of a bispecific antibody as described herein. Therefore, the term "highly efficacious in activating a T-cell" as employed herein relates to the capability of polypeptide constructs of the present invention to elucidate a T-cell activation of high activity in bioactivity-assay as defined herein above (EC values <1-10 ng/ml), of high cytotox-activity (>/–30% cell lysis), the capability to induce an upregulation of specific markers like CD69, IFN-γ, CD2, LFA-1, VLA-4, IL-2, IL-12, IL-15, IL-18 and/or CD25 and/or an increased mitotic activity as compared to a non-activated T-cell.

(Binding) affinity of the polypeptide constructs for their corresponding target may be determined as follows:

| | |
|---|---|
| >10$^{-7}$ | low affinity |
| 10$^{-8}$ | medium |
| <10$^{-9}$ | high |

As used herein, the term "binding affinity" refers to the thermodynamic affinity constants $K_A$ and $K_D$, which, related to one another through an inverse relationship, describe the binding event between either the polypeptide construct of the invention and a CD3 protein on the surface of a T-cell. One of ordinary in the art will appreciate that numerous ways exist of measuring the binding affinity of a binding interaction. Examples of methods which one of skill in the art will recognize as suitable for measuring the binding affinity of the polypeptide construct of the invention to a CD3 protein on the surface of a T-cell include, but are not limited to BIAcore™, Scatchard analysis, microcalorimetry, measurement of soluble T-cell receptor (soluble TCR assay), saturation binding analysis, cell-based competition assays and assays involving labeling with radioactive substances.

As pointed out above, it is envisaged in context of this invention that the CDR-3 region which is modified in accordance with this invention comprises at least one substitution in the YYDDHY-motif. Yet, it is also envisaged and shown herein that said CDR-3 region comprises more than one substitution, i.e. two or even three substitutions in the amino acid sequence YYDDHY (SEQ ID NO.1) and wherein said substitutions are defined herein. Preferred multiple substitutions are disclosed herein below and illustrated in the appended examples.

In a preferred embodiment, the invention relates to the polypeptide construct of the invention, wherein said at least one CDR-3 region comprising a substitution in the amino acid sequence YYDDHY (SEQ ID NO:1) is located in the CDR-3 region of a heavy chain variable region ($V_H$). Preferably, said heavy chain variable region is a $V_H$-region of an antibody capable of binding to and/or interacting with CD3. Most preferably, said antibody is OKT-3 or an antibody derived therefrom.

The invention, accordingly, relates to a polypeptide construct as defined above, wherein said heavy chain variable region ($V_H$) is selected from (a) a $V_H$-region comprising an amino acid sequence as shown in SEQ ID NO: 40, 42 or 57;
(b) a $V_H$-region encoded by a nucleic acid molecule as shown in SEQ ID NO: 41, 43 or 58;
(c) a $V_H$-region which is encoded by a polynucleotide which is at least 80% identical to the nucleic acid molecule as defined in (c) and which comprises a YYDDHY-motif as defined in claim 1; and
(d) a $V_H$-region which is encoded by a polynucleotide which hybridizes under stringent conditions with a polynucleotide/nucleic acid molecule defined in (b) or (c) and which comprises a substitution in the amino acid sequence YYDDHY (SEQ ID NO: 1) as defined above.

The term "hybridizing" as used in accordance with the present invention relates to stringent or nonstringent hybridization conditions. Preferably, it relates to stringent conditions. Said hybridization conditions may be established according to conventional protocols described, for example, in Sambrook, "Molecular Cloning, A Laboratory Manual", Cold Spring Harbor Laboratory (1989) N.Y., Ausubel, "Current Protocols in Molecular Biology", Green Publishing Associates and Wiley Interscience, N.Y. (1989), or Higgins and Hames (eds) "Nucleic acid hybridization, a practical approach" IRL Press Oxford, Washington D.C., (1985). The person skilled in the art considers, inter alia, as stringent hybridization conditions like 60° C., 2×SSC and 0.1% SDS or, as even higher stringent, 65° C., 0.1×SSC and 0.1% SDS.

In a even more preferred embodiment of the invention, the polypeptide construct comprises a CDR3 region, preferably in a $V_H$-part of an antibody or antibody fragment or a single chain construct, wherein said CDR-3 region comprises at least one substitution and is selected from the group consisting of HYDDHY (M1; SEQ ID NO: 2), YSDDHY (M4; SEQ ID NO. 3), YYDAHY (M7; SEQ ID NO. 4), YYDDQY (M9; SEQ ID NO. 5), YYDDPY (M10; SEQ ID NO. 6), YFNDHY (M11; SEQ ID NO. 7), YYNDQY (M13, SEQ ID NO. 8), YYDAHN (M14, SEQ ID NO: 9), YHDDPY (M20, SEQ ID NO. 10), YYEGRY (M31, SEQ ID NO.11), YSDVYY (M58, SEQ ID NO. 12), YSDDRY (M65, SEQ ID NO. 13), YNDEHY (M69, SEQ ID NO. 14) and YYDDNY (M76, SEQ ID NO. 15).

Most preferably, and as explained herein, said polypeptide construct of the invention is a construct which comprises at least two functional domains, i.e. the first domain (relating to the above identified, modified CDR-3 region) capable of interacting with or binding to (human) CD3 of a T-cell, and a second domain which may also be a binding molecule (like the $V_H/V_L$-regions of another antibody). Most preferably, as defined below, the polypeptide of the invention is a bispecific antibody molecule, e.g. a bispecific single chain construct, or a bispecific single chain Fv. Even more preferred in this context is a bispecific single chain Fv construct in the format that comprise $V_H$ and/or $V_L$ domains of antibodies or immunoglobulin chains. Preferably said construct comprises least one $V_H$ domain (region), wherein at least one CDR-3 region comprises a modified YYDDHY-motif as disclosed herein. It is of note that in particular the second binding site of a bispecific construct which does not comprise a CDR-3 region as defined herein may also be a binding molecule on (a) part(s) of a binding molecule which is distinct from an antibody/antibody molecule. Such a binding molecule, distinct from an antibody, may, inter alia, be a naturally occurring surface receptor or ligand (as will be detailed hereinbelow).

The most preferred polypeptide construct of the invention is, however, a construct comprising two domains as defined herein, wherein one domain comprises at least the $V_H$-region of an antibody directed against (human) CD3 of (a) T-cell(s) and wherein in said $V_H$-region the CDR-3 region is modified in the YYDDHY-motif as described herein.

The variable domains of the heavy and light antibody chains each contain three complementarity determining regions (CDRs), loci of hypervariable mutation which together are largely responsible for the binding specificity of the antibody or fragment thereof. These CDRs are surrounded by largely non-variant polypeptide stretches known as framework regions (FRs). Together, the FR regions and three CDRs make up one variable domain for each of the heavy and the light chain. The modifications, preferably substitutions described above, are preferably performed within at least one of these variable domains, more preferably within a CDR region, even more preferably within the third CDR of the heavy chain. For example, in the OKT-3 antibody, said third CDR of the $V_H$-region spans, according to the Kabat numbering system, between amino acid positions 99 to 108 of SEQ ID NO: 42 or as shown in SEQ ID NO: 36. One of skill in the art will however readily recognize that modifications within the definition of the invention are not restricted to any particular CDR region of either chain, and that alterations in CDR or even other regions of an antibody can manifest the differential affinity and activity profile required to be classified as a modification within the definition of the invention and therefore lead to the biosynthetic polypeptide of the invention. Binding to the TCR-receptor associated CD3 protein, which is expressed on the surface of the T-cell, may take the form of binding to either single or multiple sub-chains of the CD3 protein, for instance the γ, δ, ε, ζ or/and η chains of the CD3 protein.

As shown in the appended examples, the inventive polypeptide construct may be derived from the antibody or antibody fragment of OKT-3. OKT-3 is a murine antibody exhibiting binding of high specificity and affinity to the CD3 protein. In an especially preferred aspect of the invention, the polypeptide construct of the invention comprises the sequences as shown in any one of SEQ ID NOs: 2 to 15. The antibody OKT-3 may be subjected to modification in its full, meaning non-truncated form. Alternatively, OKT-3 may also be subjected to modification in a truncated form, meaning that at least one fragment of OKT-3 may serve as the antibody subjected to modification. Such fragments of OKT-3 may be provided as outlined above, namely as an Fab, as an F(ab')$_2$, as a Fv, a single chain Fv, as a bispecific single chain Fv, as an antibody fusion protein, as a humanized antibody or as a chimeric antibody. Preferred is the use of an OKT-3 antibody fragment, including but not limited to an OKT-3 Fv, an OKT-3 single chain Fv, an OKT-3 single chain Fv which makes up one binding domain of a bispecific single chain Fv, an OKT-3 fragment which makes up one domain of a multi-domain fusion protein, or an OKT-3 fragment which makes up at least one domain of a humanized antibody or a chimeric antibody. The alteration contained in the OKT-3 antibody or antibody fragment may be in any region of the OKT-3 antibody or antibody fragment, as long as this alteration endows the resulting inventive polypeptide construct of the invention with the binding and activity profile described above as being requisite for the alteration being classified as a "modification" within the definition of the invention. As for example illustrated herein, said $V_H$-region of OKT-3 may be further modified. The $V_H$-region of OKT-3 comprising the YYDDHY-motif to be modified in accordance with this invention is illustrated in SEQ ID NO: 42. Yet, the invention also illustrates that said $V_H$-region of OKT-3 may be further modified. For example SEQ ID NO: 57 relates to a $V_H$-region which is derived from the $V_H$-region of OKT-3 but comprises four additional substitutions and two additions at the N-terminus. This "mutated OKT-3 $V_H$-region" may also be modified in accordance with this invention, i.e. it may comprise a substituted YYDDHY-motif as defined herein. Accordingly, the present invention also provides for polypeptide constructs comprising a $V_H$-region derived from OKT-3 and comprising in said $V_H$-region a modified YYDDHY-motif as disclosed herein, wherein the $V_H$-region of said polypeptide construct is at least 80%, more preferably at least 85%, more preferably at least 90% and most preferably at least 95% homologous to the $V_H$-region of OKT-3 as depicted in SEQ ID NO: 42 and wherein said $V_H$-region comprises a YYDDHY-motif as defined herein.

As documented herein below and in the appended examples, it is also envisaged that existing constructs, like anti-EpCAM×anti-CD3 constructs, as inter glia described in Mack, J. Immunol. (1997), 158, 3965-3970, Mack, PNAS, (1995), 92, 7021-7025, Kufer, Cancer Immunol. Immunother., (1997), 45, 193-197, are modified in the YYDDHY-motif as described herein. In this context, the existing polypeptide constructs are specifically modified by replacing the YYDDHY-motif in the CDR-3 region of the $V_H$CD3-part with an substitution as defined herein, i.e. wherein said YYDDHY-motif is preferably replaced by a sequence depicted in any one of SEQ ID NOs 2 to 15.

As used herein and explained above, a "polypeptide construct" of the invention refers, preferably, to a polypeptide which comprises multiple binding domains within its structure. A polypeptide construct therefore represents the result of modifying an antibody or a fragment thereof, or an antibody construct, like scFv comprising two or more binding domains, at least one of which binds specifically to the CD3 protein on the surface of the T-cell and activates T-cells by virtue of this binding. In one aspect of the invention, the antibody or fragment thereof contains two domains, the first of which specifically binds to the CD3 protein on the surface of T-cells and activates T-cells and a second which has an entirely different binding specificity for some other target which is different than the CD3 protein, as detailed herein below. Modification within the T-cell binding domain of the antibody or fragment thereof or antibody construct but not in the domain of different binding specificity results in a polypeptide construct now bearing, a) the biosynthetic polypeptide in or as the first domain which specifically binds and activates T-cells and b) the (unaltered and unmodified) domain of different binding specificity in or as the second domain.

The invention provides for a polypeptide construct, inter alia, in the form of a bispecific single chain Fv comprising, as the first of its specific binding domains, a biosynthetic polypeptide comprising in its sequence as shown in SEQ ID NOs: 2 to 15 in the CDR3 region of the heavy chain, wherein the first of the two specific binding domains specifically binds to the CD3 protein on the surface of the T-cell and activates the T-cell and, as the other of its specifically binding domains, a polypeptide of binding specificity for a target other than the CD3 protein. This target other than CD3 may, inter alia, be located on a tumor target cell. Those targets may be, but are not limited to EpCAM, CD19 or CCR5 and others defined below.

In a most preferred embodiment of the invention, the polypeptide construct as defined herein is highly efficacious in activating a T-cell.

The term "highly efficacious" in activating a T-cell was explained above and is also illustrated in the appended examples.

Examples of an inventive polypeptide construct which are highly efficacious in activating a T-cell are constructs which comprise a CDR-3 of a heavy chain part of an antibody, in particular of an antibody directed against (human) CD3 of (a) T-cell(s), wherein the YYDDHY-motif is modified to YYDAHY (M7; SEQ ID NO. 4), YYDDQY (M9; SEQ ID NO. 5), YYDDPY (M10; SEQ ID NO. 6), YYNDQY (M13, SEQ ID NO. 8), YYDAHN (M14, SEQ ID NO. 9), YSDVYY (M58, SEQ ID NO. 12) or YNDEHY (M69, SEQ ID NO. 14).

In accordance with this invention, it is possible to obtain polypeptide constructs, in particular bispecific constructs which comprise a low affinity for its target, in particular CD3 of a T-cell, but are still capable of eliciting a strong or high T-cell activation. "Low affinity" relates to the capacity of the construct of the invention to bind to its target, most preferably to CD3. (Binding) affinities have been defined herein above and "low affinity" may be considered as $K_D$ values $>10^{-7}$, "medium affinity" as $K_D$-values of $\sim 10^{-8}$ and "high affinity" as $K_D$ values of $<10^{-9}$. "Low affinity" constructs preferably comprise a substitution in the YYDDHY-motif of the CDR-3 part of the heavy chain (for example of an antibody directed against CD3 of T-cells) and, preferably comprise the sequence motif YYNDQY (M13, SEQ ID NO: 8), YSDVYY (M58, SEQ ID NO: 12) or YNDEHY (M69, SEQ ID NO: 4).

Constructs according to this invention with strong capacity for T-cell activation are capable of inducing a general antigen specific activation of T-cells, independent of their clonogenic origin. This potent activation provides for, inter alia, strong release of cytokines. However, it may also be envisaged in medical settings to obtain only a moderate to low antigen-specific activation of T-cells. Should this be desired (for example in order to reduce side effects due to strong cytokine release), the polypeptide construct of the invention may comprise a CDR-3 region of $V_H$, (for example of an anti-CD3 antibody or antibody construct) wherein the YYDDHY-motif is modified (substituted) by HYDDHY (M1), YSDDHY (M4), YFNDHY (M11), YHDDPY (M20), YYEGRY (M31), YSDDRY (M65) or YYDDNY (M76).

For a "highly efficacious" (+++) to "moderate" (++) activation of T-cells, said CDR-3 region of the polypeptide construct of the invention may comprise a modified YYDDHY-motif in the format of YYDDQY (M9), YYDDPY (M10), YYNDQY (M13), YYDAHN (M14), YSDVYY (M58) or YNDEHY (M69).

A "fine-tuned" activation of T-cells is, inter alia, desired in the treatment of immunogenic tumors or in chronic virus infections, like hepatitis C infections. Similarly, in patients suffering from autoimmune disorders a "fine-tuned T-cell activation" with the construct of the invention is desired. For example, if tumor therapy has to be performed in such patients, it is desired to induce a fine-tuned T-cell activation, since a high level of immune activation already exists in these patients.

In contrast, polypeptide constructs of the invention which are capable of strong T-cell activation are useful for elimination of target cells in cancer, autoimmune and inflammatory disease. Accordingly, the use of multifunctional polypeptides inducing low/moderate T-cell activation represents an optimized approach for certain disease entities as described above, like tumor patients, suffering also from an autoimmune disorder or patients suffering from severe chronic viral infections.

The invention also provides for polypeptide constructs which have a low T-cell activating capacity, but are capable of interacting with/binding to CD3. Such constructs comprise a modified YYDDHY-motif, preferably in the $V_H$-region and even more preferably in the CDR-3 part, wherein said modified YYDDHY-motif is selected from the group consisting of HYDDHY (M1), YSDDHY (M4), YFNDHY (M11), YHDDPY (M20), YYEGRY (M31), YSDDRY (M65) and YYDDNY (M76).

Also provided are polypeptide constructs which have a low (binding) affinity for CD3 but are highly efficacious in activating a T-cell. Such constructs comprise a modified YYDDHY-motif in accordance with this invention, preferably in the $V_H$-region and most preferably in the CDR-3 part, whereby the modified YYDDHY-motif is selected from the group consisting of YYNDQY (M13), YSDVYY (M58) and YNDEHY (M69).

As pointed out above and preferably, the inventive polypeptide construct is in the format of an Fab, an F(ab')$_2$, a single chain Fv (scFv), a bispecific scFV, an antibody fusion protein or an antibody-antigen-construct or a heterominibody.

As shown in the appended examples, particular preferred formats of the polypeptide construct of the present invention comprise bispecific constructs in form of scFv, like an anti-EpCAM×anti-CD3 construct, i.e. a polypeptide construct comprises two functional domains, wherein one domain interacts/binds to a target cell/marker on a target cell, like EpCAM and the second functional domain comprises the CDR-3 region with a modified YYDDHY-motif as defined herein and which is capable of interacting with CD3 of a T-cell.

Therefore, the present invention also provides for specific anti-EpCAM×anti-CD3 constructs which comprise a modified YYDDHY-motif in the $V_H$-region of the anti-CD3 part. These constructs comprise, bispecific single chain constructs selected from the group consisting of (a) bispecific single chain constructs encoded by a nucleic acid molecule as shown in any one of SEQ ID NOs: 62, 64, 66, 68, 70, 72, 74, 76, 78, 80, 82, 84, 86 or 88;

(b) a bispecific single chain construct that has an amino acid sequence as shown in any one of SEQ ID NOs: 61, 63, 65, 67 69, 71, 73, 75, 77, 79, 81, 83, 85 or 87;

(c) a bispecific single chain construct which comprises a modified YYDDHY-motif as defined above, which is encoded by a polynucleotide/nucleic acid molecule and which is at least 80%, more preferably at least 15%, more preferably at least 90%, more preferably at least 95% and most preferably at least 99% identical to the nucleic acid molecule as shown in any one of SEQ ID NOs: 62, 64, 66, 68, 70, 72, 74, 76, 78, 80, 82, 84, 86 or 88;

(d) a bispecific single chain construct which is encoded by a polynucleotide/nucleic acid molecule which hybridizes under stringent conditions to the complementary strand of a polynucleotide/nucleic acid molecule as defined in (a) or (c) and which comprises a substitution in the amino acid sequence of the YYDDHY-motif as defined herein above.

The term "stringent condition" has been defined herein above and said hybridization conditions apply here, mutates mutantis.

In a most preferred embodiment, the polypeptide construct of the invention is in the format of a bispecific scFv comprising one domain derived from an anti-CD3 antibody (e.g. $V_H$ and $V_L$-region of OKT-3), wherein the CDR-3 region of $V_H$ is modified in the YYDDHY-motif and a second domain relating to the $V_H$ and $V_L$ region of another antibody, is directed against another target molecule, like EpCAM, CD19, CCR5 or the targets defined below. Accordingly, the invention, in a preferred embodiment, relates to a polypeptide construct comprising the format $V_L$-$V_H$-$V_H$-$V_L$, whereby at least one CDR-3 region comprises a modified YYDDHY-motif as described herein. Accordingly, in a most preferred embodiment the invention relates to a bispecific construct of the format $V_{L[Target]}$-$V_{H[Target]}$-$V_{HCD3}$-$V_{LCD3}$, whereby the $V_H$ and $V_L$ region relating to the "target" means in accordance with this invention a minimum antibody fragment which comprises a complete antigen-recognition and -binding site directed against a target as defined herein below, for example EpCAM, CCR5, CD19 and the like. The $V_{HCD3}$- and $V_{LCD3}$-region relates, accordingly, to the variable region of the antibody directed against CD3 of (a) T-cell(s), whereby the CDR-3 region of at least $V_{HCD3}$ comprises a YYDDHY-motif which is substituted in accordance with the invention.

Antibody-antigen constructs are also envisaged and be of a format wherein the first domain comprises an antigen (for example autoreactive antigens or fragments thereof) and the second domain is an antibody or an antibody part or fragment comprising a CDR-3 region (preferably in the $V_H$-part) which is modified in the YYDDHY-motif as defined herein.

As employed in accordance with this invention, the term "autoreactive antigen or (a) fragment(s) thereof" means antigens or (a) fragment(s) thereof which are capable of elucidating and/or mediating an autoimmune response. Said fragment(s) thereof is/are preferably an epitope of said antigen. Preferably, said antigens and/or its fragment(s) comprise proteinaceous structures, yet, said autoreactive antigen or (a) fragment(s) may also comprise, either alone or in addition to said proteinaceous structures, inter alia, carbohydrate moieties or lipids. The term "autoreactive antigen or (a) fragment(s) thereof" is not limited to antigens occurring in and/or deriving from the subjects own body (autologous and/or endogenous antigens) but furthermore comprises foreign molecules which are capable of eliciting an autoimmune-response by binding and/or interacting with molecules peculiar to one's own body (for example via hapten-carrier complexes). In addition, said term also comprises antigens, like microbial antigens/epitopes, that share properties, e.g. amino acid sequences, with mammalian molecules, e.g. proteins, and are capable of provoking an autoimmune-response. Examples of such antigenic mimicry are known in the art (see, inter alia, Paul, "Fundamental Immunology", Raven Press, 1989) and comprise exogenous antigens like, Streptococcal M protein, *Klebsiella* nitrogenase, Measels virus P3, retroviral p30 protein. It is preferred that the composition of the present invention comprises a (poly)peptide construct comprising a domain with at least one autoreactive antigen or at least one fragment thereof. However, it is also envisaged that said (poly)peptide construct comprises a domain comprising more than one autoreactive antigen and/or fragments and/or epitopes thereof. Said domain comprising said autoreactive antigen or (a) fragment thereof may therefore comprise several autoantigens and/or fragment(s) thereof. In a preferred embodiment said domain comprises at least one, more preferred at least two, more preferred at least three, more preferred at least four and most preferred at least five autoreactive antigen(s) or (a) fragment(s).

Antibody-antigen constructs are known in the art and, inter alia, described in WO 02/16414. Accordingly, the polypeptide construct of the invention comprises in this embodiment a construct comprising the $V_H$ (and preferably the $V_L$-region) of an antibody directed against CD3 (for example the $V_H$ and, optionally, the $V_L$ region of OKT-3) wherein at least in the $V_H$ part of the anti-CD3 antibody the YYDDHY-motif is modified/substituted in accordance with the invention. The other domain of the antibody-antigen construct described herein comprises, accordingly, one antigen as defined herein above. A specific example of such an inventive construct is an anti-EpCAM×anti-CD3 construct as disclosed herein.

Also "heterominibodies" may comprise at least one CDR-3 region (preferably of the $V_H$-part of an antibody) as defined herein. The format and the generation of, heterominibodies is known in the art and illustrated in WO 00/06605. Accordingly, the polypeptide construct of the present invention may, in one embodiment be a full antibody in form of an IgG, IgA, IgE, IgM or IgD or a fragment of such an antibody which comprises at least one $V_H$-region with a YYDDHY-motif to be modified in accordance with this invention.

In accordance with the description herein above, in a most preferred embodiment of the invention, a polypeptide construct is provided, wherein said polypeptide construct is capable of specifically binding to/interacting with the CD3 of a T-cell and comprises a modified CDR-3 region of the present invention and, with another domain, is capable of binding to/interacting with a second target molecule. Preferably, said second target molecule is selected from the group consisting of EpCAM, CCR5, CD19, HER-2, HER-2 neu, HER-3, HER-4, EGFR, PSMA, CEA, MUC-1 (mucin), MUC2, MUC3, MUC4, $MUC5_{AC}$, $MUC5_B$, MUC7, βhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen (see WO 01/47953), (membrane-bound) IgE, Melanoma Chondroitin Sulfate Proteoglycan (MCSP), CCR8, TNF-alpha precursor, STEAP, mesothelin, A33 Antigen, Prostate Stem Cell Antigen (PSCA), Ly-6, desmoglein 4, E-cadherin neo-epitope, Fetal Acetylcholine Receptor, CD25, CA19-9 marker, CA-125 marker and Muellerian Inhibitory Substance (MIS) Receptor type II, sTn (sialylated Tn antigen, TAG72), FAP (fibroblast activation antigen), endosialin, EGFRvIII, L6, SAS, CD63, TF-antigen, Cora antigen, CD7, CD22, Iga, gp100, MT-MMPs, F19-antigen, CO-29 and EphA2.

The second domain of the polypeptide construct directed against any of the target molecules described herein may also be a part of an antibody, an antibody fragment and is, in a most preferred embodiment, a scFv, preferably comprising the $V_L$ and $V_H$-region of an antibody directed against said second target molecule.

However, a most preferred polypeptide construct of the invention is capable of specifically binding to/interacting with the CD3 of a T-cell (and comprising a modified CDR-3 region in the $V_H$ part as described herein, i.e. a substitutive YYDDHY-motif in accordance with the invention) and is capable binding to/interacting with a second domain, preferably with EpCAM.

Such polypeptide constructs are detailed in the appended examples and are in a most preferred embodiment in form of a bispecific construct, namely in form of a bispecific scFv, whereby a first domain binds to/interacts with EpCAM and the second domain is derived from an antibody directed against CD3 of a T-cell, preferably derived from OKT-3, and comprises a CDR-3 (preferably of the $V_H$-region) wherein the YYDDHY-motif is modified in accordance with this invention by (a) substitution(s) described herein.

The invention also provides for a polynucleotide encoding a polypeptide construct as described herein.

Said polynucleotide may be a DNA or a RNA. Preferably, said polynucleotides are recombinant nucleic acid molecules.

This invention also provides for a vector comprising the polynucleotide described above and encoding an inventive polypeptide construct.

Said vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions. Particularly preferred vectors are vectors as, inter alia, described in the appended examples and comprise, e.g. the expression vector pEF-DHFR (Mack, 1997, J. Immun. 158, 3965-3970), pEF-neo or CD19×CD3 pEF-dhfr.

Furthermore, the vector of the composition of the present invention, may in addition to the polynucleotides/nucleic acid sequences described herein above, comprise expression control elements, allowing proper expression of the coding regions in suitable hosts. Such control elements are known to the artisan and may include a promoter, a splice cassette, translation initiation codon, translation and insertion site for introducing an insert into the vector. Preferably, the nucleic acid molecule of the invention is operatively linked to said expression control sequences allowing expression in eukaryotic or prokaryotic cells.

Control elements ensuring expression in eukaryotic and prokaryotic cells are well known to those skilled in the art. As mentioned herein above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous sarcoma virus), human elongation factor 1α-promoter, enhancers, like CMV enhancer or SV40-enhancer. For the expression in prokaryotic cells, a multitude of promoters including, for example, the tac-lac-promoter or the trp promoter, has been described. Besides elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (Invitrogene), pSPORT1, pEF-dhfr or prokaryotic expression vectors, such as lambda gt11, pDS or pET. Beside the nucleic acid described herein, the vector may further comprise nucleic acid sequences encoding for secretion signals. Such sequences are well known to the person skilled in the art. Furthermore, depending on the expression system used leader sequences capable of directing the peptides of the invention to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a protein thereof, into the periplasmic space or extracellular medium. Optionally, the heterologous sequence can encode a fusion protein including an C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the polypeptide constructs of the invention may follow.

As mentioned herein above, the vector of the composition of the present invention may also be an expression vector. Gene therapy, which is based on introducing therapeutic genes into cells by ex-vivo or in-vivo techniques is one of the most important applications of gene transfer. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Onodua, Blood 91 (1998), 30-36; Verzeletti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO 94/29469; WO 97/00957; U.S. Pat. No. 5,580,859; U.S. Pat. No. 5,589,466; U.S. Pat. No. 4,394,448 or Schaper, Current Opinion in Biotechnology 7 (1996), 635-640, and references cited therein. In particular, vectors and/or gene delivery systems are also described in gene therapy approaches in oncology, immunology, virology or in neurology, for example Linden, Proc. Natl. Acad. Sci. U.S.A. 93 (1996), 11288-11294; Maass, Hum. Gene Ther. 9 (1998), 1049-1059; Hallek, Cytokines Mol. Ther. 2 (1996), 69-79; Peel, Neurosci. Methods 98 (2000), 95-104; Chen, J. Neurosci. Res. 55 (1999), 504-513, Mack, Clin. Pharmaco. 41 (2002), 901-911. The nucleic acid molecules and vectors described herein may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the nucleic acid molecules of the invention.

The invention also provides for a host cell comprising the polynucleotide of the invention.

In a still further embodiment, the present invention relates to a (host) cell containing the polynucleotide or vector described above. Preferably, said cell is a eukaryotic, most preferably a mammalian cell if therapeutic uses of the polypeptide are envisaged. Of course, yeast and less preferred prokaryotic, e.g., bacterial cells may serve as well, in particular if the produced polypeptide is used as a diagnostic means.

The polynucleotide or vector of the invention which is present in the host cell may either be integrated into the genome of the host cell or it may be maintained extrachromosomally.

The term "prokaryotic" is meant to include all bacteria which can be transformed or transfected with a DNA or RNA molecules for the expression of a polypeptide of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect, animal and preferably mammalian cells. Depending upon the host employed in a recombinant production procedure, the polypeptide construct of the present invention may be glycosylated or may be non-glycosylated. Polypeptide construct of the invention may also include an initial methionine amino acid residue. A polynucleotide coding for a polypeptide construct of the invention can be used to transform or transfect the host using any of the techniques commonly known to those of ordinary skill in the art. Especially preferred is the use of a plasmid or a virus containing the coding sequence of the polypeptide of the invention and genetically fused thereto an N-terminal FLAG-tag and/or C-terminal His-tag. Preferably, the length of said FLAG-tag is about 4 to 8 amino acids, most preferably 8 amino acids. Methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, N.Y., 1989). The genetic constructs and methods described therein can be utilized for expression of the polypeptide of the invention in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Furthermore, transgenic animals, preferably mammals, comprising cells of the invention may be used for the large scale production of the polypeptide of the invention.

In a most preferred embodiment of the invention, a method for the preparation of a polypeptide as described herein above is provided which process comprises cultivating a (host) cell of the invention and isolating said polypeptide from said culture.

A specific preparation protocol for a polypeptide construct of the invention is provided in the appended examples.

Most preferably, the present invention provides for a method of producing a polypeptide construct which is, preferably, highly efficacious in activating a T-cell by specifically binding to the third cluster of differentiation protein (CD3) on the surface of a T-cell, comprising the steps:

(a) providing an antibody or a fragment thereof known to specifically bind to said CD3 protein;
(b) modifying said antibody or fragment thereof by modifying the CDR-3 region in accordance with this invention; and
(c) isolating said modified antibody or fragment thereof to obtain said polypeptide construct of the invention.

Said modification in step (b) comprises the substitution of at least one amino acid in the YYDDHY-motif of the CDR-3 region of, preferably, a $V_H$-region.

In another aspect the invention relates to a composition comprising a polypeptide construct described above or as produced by the method disclosed herein, a polynucleotide of the invention, a vector or a host cell of the invention.

Most preferably, said composition is a pharmaceutical composition further, comprising, optionally, suitable formulations of carrier, stabilizers and/or excipients or said composition is a diagnostic composition further comprising, optionally, means and methods for detection.

The pharmaceutical composition of the present invention may be particularly useful in preventing, ameliorating and/or treating cancer, B-cell malignancies, AML, CML, leukemias, arthritis, asthma, allergies, or other autoimmune disorders/diseases. It is most preferred that the polypeptide construct of the invention is a construct comprising at least two target domains, wherein the first domain interacts with the CD3 of (a) T-cell(s) and comprises a CDR-3 modified in accordance with this invention (i.e. a modified YYDDHY-motif in, preferably, the $V_H$-part) and wherein said second domain is capable of interacting with another target molecule, like EpCAM, CCR5, CD19 and the like. Such second target molecules are described and exemplified herein.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in a brain artery or directly into brain tissue. The compositions of the invention may also be administered directly to the target site, e.g., by biolistic delivery to an external or internal target site, like the brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg per dose; however, doses below or above this exemplary range are envisioned, especially considering the aforementioned factors. If the regimen is a continuous infusion, it should also be in the range of 1 µg to 10 mg units per kilogram of body weight per minute, respectively. In context of the present invention, it is preferred that that the peptides of the present invention are employed in concentrations of less than 500 µg/ml, more preferred at less than 100 µg/ml, more preferred of less than 10 µg/ml and most preferred of less than 1 µg/ml. Generally, the regimen as a regular administration of the pharmaceutical composition should be in the range of 1 µg to 5 g units per day. A preferred dosage for continuous infusion is in the range of 0.01 µg to 2 mg, preferably 0.01 µg to 1 mg, more preferably 0.01 µg to 100 µg, even more preferably 0.01 µg to 50 µg and most preferably 0.01 µg to 10 µg units per kilogram of body weight per hour.

Progress can be monitored by periodic assessment. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringers dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. Said agents may be drugs acting on the immune system, like FK506 (Tacrolimus), cyclosporin, IFNbeta, azathioprine, cyclophosphamide, prednisone, corticosteroids, cyclosporin-A, -B, -C, -D, -G, calcineurin and rapamycin.

In a further embodiment, the invention relates to the use of a polypeptide construct described herein or as produced by the method of the invention, a polynucleotide, a vector or a host cell of the invention for the preparation of a pharmaceutical composition for the prevention, treatment or amelioration of a proliferative disease, a tumorous disease, an inflammatory disease, an immunological disorder, an autoimmune disease or an infectious disease.

As discussed above, in the most preferred embodiment of the polypeptide construct of the invention, said polypeptide construct comprises at least two domains, where a first of said at least two domains is capable of binding to/interacting with CD3 of (a) T-cell(s), preferably with human CD3, and comprises a CDR-3 region as defined herein, i.e. a CDR-3 region comprising a modified YYDDHY-motif as disclosed in this invention. The second of said at least two domains is capable of binding to/interacting with another target, in particular with cell surface molecules as described herein. Accordingly, these inventive constructs are particular useful in the treatment of disorder as disclosed herein.

Examples of these disorders are given herein below, whereby the corresponding preferred second "target" molecule is also provided.

Therefore, in a most preferred embodiment, the invention provides for a polypeptide construct having at least two specificities (domains), wherein the first domain comprises at least a modified CDR-3 region as defined herein and wherein said first domain is capable of binding to/interacting with CD3 of (a) T-cell(s), preferably with human CD3 of human T-cell(s). Examples of potential and desired second domains are given herein and listed below.

| Preferred second target domains | Disorders/Malignancies to be treated |
|---|---|
| CD19 (Kvalheim, Bone Marrow Transplant 1988, 3(1): 31-41; Dorken, Lancet 1974 Dec 14; 2(7894): 1463) Igα (CD79a) (Mason, Blood, 1995, 86: 1453-9), Igβ (CD79b) (Cragg, Blood, 2002, 100: 3069-76) | Various B cell malignancies: |
| CD20 (Montserrat, Semin. Oncol, 2003, 30 (1 suppl2): 34-39) | B cell lymphoma |
| CD22 (Miller, 1991, Am J Clin Pathol, 96: 100-8) | Hairy cell leukemia |
| CD7 (Preijers, Br. J Haematol, 1989, 71: 195-201) | T cell malignancies |
| CD30 (Wahl, Cancer Res 2002, 62(13): 3736-42) | Hodgkin lymphoma |
| CD33 (Maslak, Expert Opin Investig Drugs 2000, 9(6): 1197-205; Stadtmauer, Curr Oncol Rep 2002, 4(5): 375-80) | AML (acute myeloic leukemia) |
| CD33 (Lopez-Karpovitch, Rev Invest Clin 1997, 49(1): 31-6) | CML (chronic myeloic leukemia) |
| CD25 (Dahmoush, Cancer 2002, 96(2): 110-6; Savoie, Curr Treat Options Oncol 2001, 2(3): 217-24) | Certain T-cell and B-cell leukemias |
| CD19 (Issacs, Arthritis Rheum 2001, 44(9): 1998-2008), CCR5 (Bruhl, J Immunol 2001, 166(4): 2420-6), TNF-alpha precursor (Wollheim, Expert Opin Investig Drugs 2002, 11(7): 947-53) | Rheumatoid arthritis |
| CD19 (Sato, J Immunol 2000, 165(11): 6635-43, CCR5 (Zapico, Genes Immun 2000; 1(4): 288-9), CD30 (Okumura, J Clin Endocrinol Metab 1997, 82(6): 1757-60) | Autoimmune diseases |
| CCR8 (Owen, Pulm Pharmacol Ther 2001; 14(3): 193-202) | Asthma |
| IgE (membrane bound) (Lustgarten, Eur J Immunol 1995, 25(10): 2985-91) | Allergy |
| EpCAM (Naundorf, Int J Cancer 2002, 100(1): 101-10), EGFR (Liu, Br J Cancer 2000, 82(12): 1991-9), CEA (Stewart, Cancer Immunol Immunother 1999, 47(6): 299-306; Durbin, Proc Natl Acad Sci USA 1994, 91(10): 4313-7), TAG-72 (tumor associated glycoprotein =>sTn | Pan-carcinoma |

-continued

| Preferred second target domains | Disorders/Malignancies to be treated |
|---|---|
| antigen) (Kashmiri, Crit Rev Oncol Hematol 2001, 38(1): 3-16), Sonic Hedgehog (Shh) (Lacour, Br J Dermatol 2002, 146 Suppl 61: 17-9; Tojo, Br J Dermatol 2002, 146(1): 69-73), fibroblast activation antigen (FAP) (Scanlan, Proc Natl Acad Sci, 1994: 91: 5657-61), endosialin (Rettig, Proc Natl Acad Sci, 1992, 89: 10832-6), L6 (Hellstrom I, 1986, Proc Natl Acad Sci 83: 7059-63), MT-MMPs (Yana, Clin Exp Metastasis, 2002, 19: 209-15) | |
| Her-2 (Arteaga, Semin Oncol 2002, 29(3 Suppl 11): 4-10; Wester, Acta Oncol 2002; 41(3): 282-8) | Mamma carcinoma and other carcinomas |
| EGFR (Bonner, Semin Radiat Oncol 2002, 12: 11-20; Kiyota, Oncology 2002; 63 (1): 92-8), CD44v6 related to stage of carcinoma (Rodrigo, Am J Clin Pathol 2002, 118(1): 67-72; Fonseca, J Surg Oncol 2001, 76(2): 115-20) | Squamous cell carcinoma |
| PSMA (Fracasso, Prostate 2002, 53(1): 9-23), STEAP (Hubert, Proc Natl Acad Sci USA 1999, 96(25): 14523-8), PSCA (prostate stem cell antigen) (Jalkut, Curr Opin Urol 2002, 12(5): 401-6), MUC-2 (Zhang, Clin Canc Res 1998, 4: 2669-2676), TF antigen (Zhang, Int J Canc, 1997, 73: 50-56), EGFRvIII (Olapade-Olaopa, Br J Cancer 2000 82: 186-94) | Prostate cancer |
| CEA (Stewart, Cancer Immunol Immunother 1999, 47(6): 299-306; Durbin, Proc Natl Acad Sci USA 1994, 91(10): 4313-7), TAG-72 (tumor associated glycoprotein => sTn antigen) (Kashmiri, Crit Rev Oncol Hematol 2001, 38(1): 3-16), | Adenocarcinoma |
| MUC-1 (mucin) (Couto, Adv Exp Med Biol 1994; 353: 55-9) | Breast cancer |
| SCLC (small cell lung cancer): ganglioside GD3 (Brezicka, Lung Cancer 2000, 28(1): 29-36; Sheperd, Semin Oncol 2001, 28(2 Suppl 4): 30-7), Her-2/neu (Ross, Oncologist, 2003; 8: 307-325, Bacus, Am J Clin Pathol, 1994, 102(4Suppl 1): S13-24), HER-3 (Bacus, Am J Clin Pathol, 1994, 102(4Suppl 1): S13-24), HER-4 (Bacus, Am J Clin Pathol, 1994, 102(4Suppl 1): S13-24), Globo H (Int J Canc 1997, 73: 42-49), HER-2/neu (Slamon, Science, 1987 235: 177-82) | |
| mesothelin (Scholler, Proc Natl Acad Sci USA 1999, 96(20): 11531-6; Brinkmann, Int J Cancer 1997, 71(4): 638-44), CA-125 (Hogdall, Anticancer Res 2002, 22(3): 1765-8), Muellerian Inhibitory Substance (MIS) Receptor Type II (Stephen, Clin Cancer Res 2002, 8(8): 2640-6), MUC-3 (Zhang, Clin Canc Res 1998, 4: 2669-2676), TF antigen (Zhang, Int J Canc, 1997, 73: 50-56), HER-2/neu (Salomon, Science, 1989, 244: 707-712) | Ovarian cancer |
| Ly-6 (Eshel, Int J Cancer 2002, 98(6): 803-10), desmoglein 4 (Tomson, Clin Exp Metastasis 1996, 14(6): 501-11) | Head and Neck cancer |
| Lewis-Y (Power, Cancer Immunol Immunother 2001, 50(5): 241-50) | Epithelial cancers |
| E-cadherin neoepitope (Becker, Surg Oncol 2000, 9(1): 5-11), HER-3, HER-4, MUC-3 (Zhang, Clin Canc Res 1998, 4: 2669-2676), MUC-5$_{AC}$ (Zhang, Clin Canc Res 1998, 4: 2669-2676), Cora | Gastric cancers |
| antigen (Gottlinger, Cancer Res 1988, 15: 2198-203) | |
| MUC-1 (mucin) (Hanski, Cancer Res 1993, 53(17): 4082-8), Lewis-Y (Flieger, Clin Exp Immunol 2001, 123(1): 9-14; Power, Cancer Immunol Immunother 2001, 50(5): 241-50), A33 antigen (Heath, Proc Natl Acad Sci USA 1997, 94(2): 469-74), MUC-2 (Zhang, Clin Canc Res 1998, 4: 2669-2676), MUC-4 (Zhang, Clin Canc Res 1998, 4: 2669-2676), MUC-7 (Zhang, Clin Canc Res 1998, 4: 2669-2676), TF antigen (Zhang, Int J Canc, 1997, 73: 50-56), CO-29 | Colon carcinoma |
| Carbonic anhydrase IX (MN/CA IX) (Uemura, Br J Cancer 1999, 81(4): 741-6 | Renal cell carcinoma |
| Carbonic anhydrase IX (MN/CA IX) (Longcaster, Cancer Res 2001, 61(17): 6394-9) | Cervix carcinoma |
| Carbonic anhydrase IX (MN/CA IX) (Chia, J Clin Oncol 2001, 19(16): 3660-8), MUC-5$_{Ac}$ (Zhang, Clin Canc Res 1998, 4: 2669-2676), MUC-5$_B$ (Zhang, Clin Canc Res 1998, 4: 2669-2676), EphA2 (Zelinski, Cancer Res., 2001, 61: 2301-6) | Breast carcinoma |
| Carbonic anhydrase IX (MN/CA IX) (Beasley, Cancer Res 2001, 61(13): 5262-7) | Head and neck squamous cell carcinoma |
| MUC-4 (Zhang, Clin Canc Res 1998, 4: 2669-2676), βhCG (Zhang, Clin Canc Res 1998, 4: 2669-2676), L6 (Hellstrom, Cancer Res, 1986, 46: 3917-23) | Lung cancer |
| CA19-9 marker (Brockmann, Anticancer Res 2000, 20(6D): 4941-7) MUC-4 (Zhang, Clin Canc Res 1998, 4: 2669-2676), βhCG (Zhang, Clin Canc Res 1998, 4: 2669-2676), Globo H (Int J Canc 1997, 73: 42-49) | Pancreas carcinoma |
| GM2 (Int J Canc 1997, 73: 42-49), fucosyl GM1 (Int J Canc 1997, 73: 42-49), poly sialic acid (SA) (Int J Canc 1997, 73: 42-49) | Small cell lung cancer |
| GM2 (Int J Canc 1997, 73: 42-49), GD2 (Int J Canc 1997, 73: 42-49), SAS (Jankowski, Oncogene, 1994, 9: 1205-11) | Sarcoma |
| Fetal AchR (acetylcholin receptor) (Gattenloehner, Am J Pathol 1998, 152(2): 437-44) | Rhabdomyosarcoma |
| EGFR (Kuan, Brain Tumor Pathol 2000; 17(2): 71-8), EGFRvIII (Wikstrand, Cancer Res., 1995: 55: 3140-8) | Glioma |
| Wue-1 Plasma cell antigen (Greiner, Virchows Arch 2000, 437(4): 372-9) | Multiple Myeloma |
| ganglioside GD3 (Dippold, Cancer Res 1984, 44(2): 806-10; Scott, J Clin Oncol 2001, 19(19): 3976-87), MCSP (melanoma chondroitin sulfate proteoglycan) (Pluschke, Proc Natl Acad Sci USA 1996, 93(18): 9710-5; Geiser, Cancer Res 1999, 59(4): 905-10), 9-O-acetyl-GD3 (Int J Canc 1997, 73: 42-49), GM2 (Int J Canc 1997, 73: 42-49), GD2 (Int J Canc 1997, 73: 42-49), CD63 (Azorsa, Blood, 1991 78: 280-4), gp100 (de Vries, Cancer Res, 1997, 57: 3223-9) | Melanoma |
| CD44v6 (Rodrigo, Am J Clin Pathol 2002, 118(1): 67-72; Fonseca, J Surg Oncol 2001, 76(2): 115-20) | Metastatic disease |

Accordingly, the present invention also provides for a method for the prevention, treatment or amelioration of a proliferative disease, a tumorous disease, an inflammatory disease, an immunological disorder, an autoimmune disease or an infectious disease comprising the step of administering to a subject in need of such a prevention, treatment or amelioration a polypeptide construct of the invention or as produced by the method described above, a polynucleotide, a vector or a host cell of the invention. Most preferably, the subject to be treated is a human.

The compositions, in particular the pharmaceutical compositions, uses and methods of the invention can be used for all kinds of diseases hitherto unknown as being related to or dependent on auto-antigens and/or the production of auto-antibodies. Said compositions, uses and methods of the invention may be desirably employed in humans, although animal treatment is also encompassed by the uses and methods described herein.

In accordance with this invention, the terms "treatment", "treating" and the like are used herein to generally mean obtaining a desired pharmacological and/or physiological effect. Said effect may be prophylactic in terms of completely or partially preventing a disease, in particular, an autoimmune disease, or a symptom thereof and/or may be therapeutic in terms of completely or partially curing a disease, in particular, an autoimmune disease, and/or (an) adverse effect(s) attributed to said disease. The term "treatment" as used herein includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

The invention also provides for a kit comprising a polypeptide construct or as produced by the method of the invention, a polynucleotide, a vector or a host cell of the invention.

The Examples illustrate the invention

Example 1

Description of Relevant Sequences of OKT3 scFv constructs anti human EpCAM×anti human CD3 were used for generation of mutants in the VH part of anti-CD3 antibody OKT3. Amino acid and nucleotide sequences of VH of OKT3 were derived from NCBI database. The OKT3 heavy chain is available under accession number A22261 and the variable region is deposited under D82081.

The wildtype amino acid sequence of CDR3 of VH part of anti CD3 monoclonal antibody OKT3 used herein: Tyr-TyrAspAspHisTyrCysLeuAspTyr (SEQ ID NO: 36) The wildtype nucleotide sequence of CDR3 of VH part of anti CD3 monoclonal antibody OKT3 used herein: TATTATGATGATCATTACTGCCTTGACTAC (SEQ ID NO: 37)

In the following the corresponding sequences are depicted

A22261: OKT3 Heavy Chain, Amino Acid Sequence (with Signal Peptide):

```
MERHWIFLLLLSVTAGVHSQVQLQQSGAELARPGASVKMSCKASGYTFTRYTM    (SEQ ID NO: 38)

HWVKQRPGQGLEWIGYINPSRGYTNYNQKFKDKATLTTDKSSSTAYMQLSSLT

SEDSAVYYCARYYDDHYCLDYWGQGTTLTVSSAKTTAPSVYPLAPVCGDTTGS

SVTLGCLVKGYFPEPVTLTWNSGSLSSGVHTFPAVLQSDLYTLSSSVTVTSSTW

PSQSITCNVAHPASSTKVDKKIEPRGPTIKPCPPCKCPAPNLLGGPSVFIFPPKIK

DVLMISLSPIVTCVVVDVSEDDPDVQISWFVNNVEVHTAQTQTHREDYNSTLRVV

SALPIQHQDWMSGKEFKCKVNNKDLPAPIERTISKPKGSVRAPQVYVLPPPEEE

MTKKQVTLTCMVTDFMPEDIYVEWTNNGKTELNYKNTEPVLDSDGSYFMYSKL

RVEKKNWVERNSYSCSVVHEGLHNHHTTKSFSRTPGK
```

A22261: OKT3 Heavy Chain, Nucleotide Sequence (with Signal Peptide):

```
gaattcccctctccacagacactgaaaactctgactcaacatggaaaggcactggatctttctactcctgttgtcagt    (SEQ ID NO: 39)

aactgcaggtgtccactcccaggtccagctgcagcagtctggggctgaactggcaagacctggggcctcagtga agatgtcctgcaaggcttctggctacacctttactaggtacacgatgcactgggtaaaacagaggcctggacagg gtctggaatggattggatacattaatcctagccgtggttatactaattacaatcagaagttcaaggacaaggccac attgactacagacaaatcctccagcacagcctacatgcaactgagcagcctgacatctgaggactctgcagtcta ttactgtgcaagatattatgatgatcattactgccttgacta ctggggccaaggcaccactctcacagtctcctcagccaaaacaacagcccatcggtctatccactggcccctgt gtgtggagatacaactggctcctcggtgactctaggatgcctggtcaagggttatttccctgagccagtgaccttga cctggaactctggatccctgtccagtggtgtgcacaccttcccagctgtcctgcagtctgacctctacaccctcagca gctcagtgactgtaacctcgagcacctggcccagccagtccatcacctgcaatgtggccaccggcaagcag caccaaggtggacaagaaaattgagcccagagggcccacaatcaagcctgtcctccatgcaaatgcccagc
```

```
acctaacctcttgggtggaccatccgtcttcatcttccctccaaa
gatcaaggatgtactcatgatctccctgagccccatagtcacatgtgtggtggtggatgtgagcgaggatgaccca
gatgtccagatcagctggtttgtgaacaacgtggaagtacacacagctcagacacaaacccatagagaggatta
caacagtactctccgggtggtcagtgcccctcccatccagcaccaggactggatgagtggcaaggagttcaaat
gcaaggtcaacaacaaagacctcccagcgcccatcgagagaaccatctcaaaacccaaagggtcagtaaga
gctccacaggtatatgtcttgcctccaccagaagaagagatgactaagaaacaggtcactctgacctgcatggtc
acagacttcatgcctgaagacatttacgtggagtggaccaacaacgggaaaacagagctaaactacaagaac
actgaaccagtcctggactctgatggttcttacttcatgtacagcaagctgagagtggaaaagaagaactgggtg
gaaagaaatagctactcctgttcagtggtccacgagggtctgcacaatcaccacacgactaagagcttctcccgg
actccgggtaaatgagctcagcacccacaaaactctcaggtccaaagagacacccacactcatctcca
tgcttcccttgtataaataaagcacccagcaatgcctgggaccatgtaaaaaaaaaaaaaaaggaattc
```

D82081, OKT3 Heavy Chain Variable Region, Amino Acid Sequence (with Signal Peptide):

```
MDWVWTLLFLLSVTAGVHSQVQLQQSGAELARPGASVKMSCKASGYTFTRYT         (SEQ ID NO: 40)
MHWVKQRPGQGLEWIGYINPSRGYTNYNQKFKDKATLTTDKSSTAYMQLSSL
TSEDSAVYYCARYYDDHYCLDYWGQGTTLTVSS
```

D82081, OKT3 Heavy Chain Variable Region, Nucleotide Sequence (with Signal Peptide):

```
Tccatggattgggtgtggaccttgctattcctgttgtcagtaactgcaggtgtccactcccaggtccagctgcagcag    (SEQ ID NO: 41)
tctggggctgaactggcaagacctggggcctcagtgaagatgtcctgcaaggcttctggctacacctttactaggt
acacgatgcactgggtaaaacagaggcctggacagggtctggaatggattggatacattaatcctagccgtggtt
atactaattacaatcagaagttcaaggacaaggccacattgactacagacaaatcctccagcacagcctacatg
caactgagcagcctgacatctgaggactctgcagtctattactgtgcaagatattatgatgatcattactgccttgact
actggggccaaggcaccactctcacagtctcctca
```

D82081 Contains a Signal Peptide which is Different from the Signal Peptide in A22261:

Variable Region (V$_H$) of Okt3 without Signal Peptide:

Amino Acid Sequence:

```
QVQLQQSGAELARPGASVKMSCKASGYTFTRYTMHWVKQRPGQGLEWIGYIN        (SEQ ID NO: 42)
PSRGYTNYNQKFKDKATLTTDKSSTAYMQLSSLTSEDSAVYYCARYYDDHYCL
DYWGQGTTLTVSS
```

Nucleotide Sequence of Variable V$_H$-Region of OKT-3:

```
caggtccagctgcagcagtctggggctgaactggcaagacctggggcctcagtgaagatgtcctgcaaggcttc    (SEQ ID NO: 43)
tggctacacctttactaggtacacgatgcactgggtaaaacagaggcctggacagggtctggaatggattggata
cattaatcctagccgtggttatactaattacaatcagaagttcaaggacaaggccacattgactacagacaaatcc
```

-continued

```
tccagcacagcctacatgcaactgagcagcctgacatctgaggactctgcagtctattactgtgcaagatattatg atgatcattactgccttgactactggggccaaggcaccactctcacagtctcctca
```

Example 2

Generation of Mutated Anti-CD3 Expression Vectors

Expression vectors containing random mutations in the CDR3 of the anti-CD3 heavy chain sequence, 5'-TATTAT-GATGATCATTAC-3' (SEQ ID NO:89), were generated by using the QuikChange Site-Directed Mutagenesis Kit (Stratagene). A pEF-DHFR plasmid coding for a bispecific antibody anti-EpCAM/anti-CD3, (Mack 1997, J. Immunol. 158, 3965-3970) was used as a template for extension with Pfu-Turbo DNA polymerase. Randomly mutated oligonucleotide primer batches specific for the heavy chain of CDR3 were synthesized. Control primers were used to generate 0% (wildtype) and 100% of mutations in the target sequence (M0). Plasmids were purified from individual transformed XL1 colonies and subsequently sequenced (ABI Prism 310, Perkin Elmer).

Wildtype Sequence of VH CDR3 of OKT3 Used for Generation of Mutants:

```
WT                TyrTyrAspAspHisTyr[SEQ ID NO: 1]

WT nucleotide     TATTATGATGATCATTAC[SEQ ID NO 27]
sequence

Mutants:

Mutant M13        TyrTyrAsnAspGlnTyr[SEQ ID NO 8]

M13 nucleotide    TATTATAATGATCAATAC[SEQ ID NO 28]
sequence

Mutant M58        TyrSerAspValTyrTyr[SEQ ID NO 12]

M58 nucleotide    TATTCTGATGTTTACTAC[SEQ ID NO 29]
sequence

Mutant M69        TyrAsnAspGluHisTyr[SEQ ID NO 14]

M69 nucleotide    TATTATGATGATCATTAC[SEQ ID NO 30]
sequence

Controls:

Mutant M0         ValValSerSerGlnVal[SEQ ID NO 26]

M0 nucleotide     GTTGTCTCCTCCCAAGTT[SEQ ID NO 31]
sequence

Mutant M12        TyrTyrHisHisHisTyr[SEQ ID NO 20]

M12 nucleotide    TATTATCATCATCATTAC[SEQ ID NO 32]
sequence

Mutant M16        TyrAspAspGluHisCys[SEQ ID NO 21]

M16 nucleotide    TATGATGATGAACATTGC[SEQ ID NO 33]
sequence

Mutant M65        TyrSerAspAspArgTyr[SEQ ID NO 13]

M65 nucleotide    TATTCCGATGATAGATAT[SEQ ID NO 34]
sequence

Mutant M76        TyrTyrAspAspAsnTyr[SEQ ID NO 15]

M76 nucleotide    TATTATGATGATAACTAT[SEQ ID NO 35]
sequence
```

In accordance with this invention, it is of note that amino acid sequence as shown in any one of SEQ ID NOs: 1, 8, 12, 14, 26, 20, 21, 13 or 15 may also be encoded by further nucleic acid sequences than the sequences depicted herein above, due to the degeneracy of the genetic code.

Example 3

Binding of Wildtype and CD3 Mutant Bispecific Antibodies to Human T Cells

Figure 1:
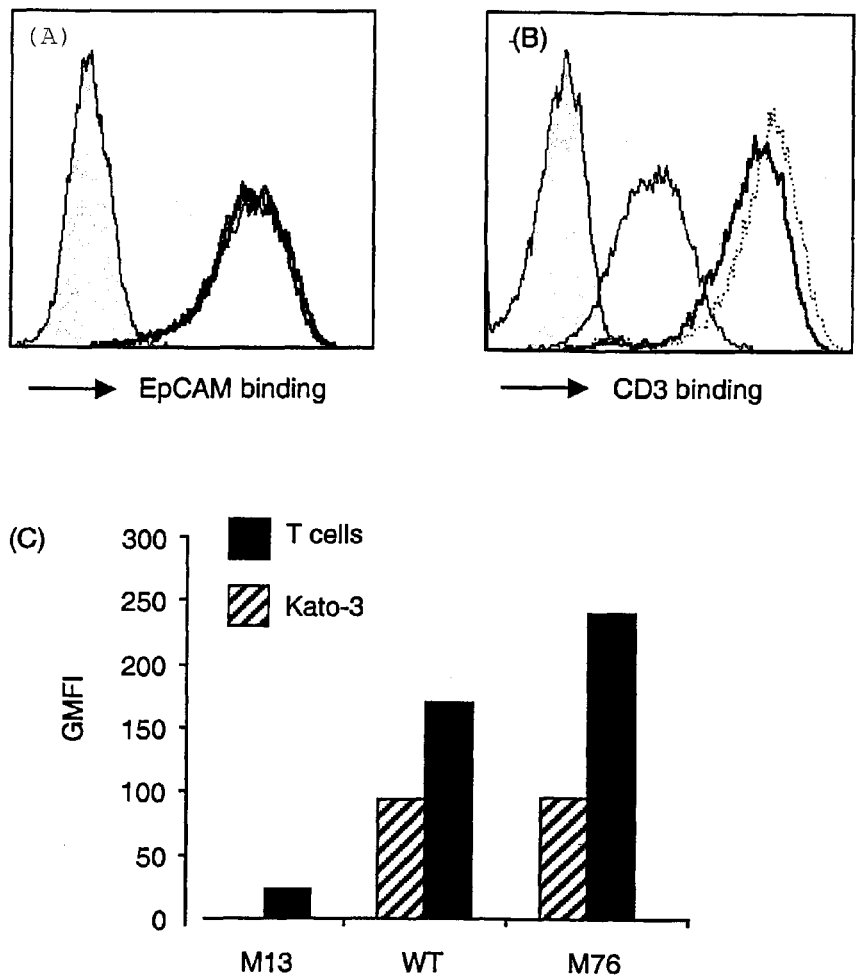
FIG. 1. Binding of wildtype and CD3 mutant bispecific antibodies to human T cells.

The mutants generated in Example 1 were sequenced and bispecific antibodies were expressed in dhFr-CHO cells (ATCC) as described (Mack 1995, PNAS 92, 7021-7025; Mack 1997, Immunity 4, 565-571). Bispecific antibodies were tested for their capacity to bind to CD3 and activate human T cells in the presence of EpCAM$^+$Kato-3 cells by FACS analysis (FIG. 1).

T cell blasts (Valitutti 1996, J. Exp. Med. 183, 1917-1921) were grown in RPMI 1640 supplemented with 5% human serum, 2 mM glutamine, pyruvate, non essential aminoacids, antibiotics and $5\times10^{-5}$ M 2-mercaptoethanol. The EpCAM positive cell line Kato-3 cells (ATCC) was grown in DMEM 10% FCS.

To detect the amount of mutant CD3 bispecific antibodies binding to the cell surface FACS analysis were performed. Kato-3 (FIG. 1A) and peripheral blood T cells (FIG. 1B) were incubated with wildtype (WT) or mutant CD3 bispecific antibody (M13, M76). Binding of bispecific antibodies was detected with an anti-6×HIS monoclonal antibody (Pharmacia) and PE-conjugated goat anti-mouse IgG2a (Southern Biotechnologies). Kato-3 cells were considered loaded with equal amounts of bispecific antibody if the geometric mean fluorescence intensity (GMFI) differed by a maximum of ±3% from the average value. Geometric mean fluorescence intensity (GMFI) data were measured (FIG. 1C).

Table 1. Mutations generated in the anti-CD3 VH CDR3 sequence of the anti-EpCAM×anti-CD3 bispecific antibodies. Amino acid sequence of the wildtype (WT) and PCR derived bispecific antibodies CD3 mutants (M). CD3 binding capacity was evaluated by staining peripheral blood T cells. The T cell stimulatory capacity was evaluated by measuring CD69 up-regulation in cultures of peripheral blood T cells and Kato-3 cells. M0 represents a mutant with a completely substituted CDR3 which was generated as a negative control. The position of amino acids as shown in table 1 correspond to position 99 to 104, whereby position 1 corresponds to the first amino acid in the VH-CDR3 region of OKT-3 as shown in SEQ ID NO: 42.

| Position: | 99 | 100 | 101 | 102 | 103 | 104 | VH CDR3 sequence: | CD3 binding | Activity |
|---|---|---|---|---|---|---|---|---|---|
| WT | Y | Y | D | D | H | Y | (SEQ ID NO: 1) | +++ | +++ |
| M0 | V | V | S | S | Q | V | (SEQ ID NO: 26) | – | 0 |
| M1 | H | Y | D | D | H | Y | (SEQ ID NO: 2) | –/+ | + |
| M2 | D | Y | D | D | H | Y | (SEQ ID NO: 16) | – | 0 |
| M3 | F | Y | D | D | H | Y | (SEQ ID NO: 17) | – | 0 |
| M4 | Y | S | D | D | H | Y | (SEQ ID NO: 3) | ++ | + |
| M5 | Y | Y | V | D | H | Y | (SEQ ID NO: 18) | – | 0 |
| M6 | Y | Y | A | D | H | Y | (SEQ ID NO: 19) | – | 0 |
| M7 | Y | Y | D | A | H | Y | (SEQ ID NO: 4) | +++ | +++ |
| M9 | Y | Y | D | D | Q | Y | (SEQ ID NO: 5) | +++ | ++ |
| M10 | Y | Y | D | D | P | Y | (SEQ ID NO: 6) | +++ | ++ |
| M11 | Y | F | N | D | H | Y | (SEQ ID NO: 7) | –/+ | + |
| M12 | Y | Y | H | H | H | Y | (SEQ ID NO: 20) | – | 0 |
| M13 | Y | Y | N | D | Q | Y | (SEQ ID NO: 8) | + | ++ |
| M14 | Y | Y | D | A | H | N | (SEQ ID NO: 9) | +++ | ++ |
| M16 | Y | D | D | E | H | C | (SEQ ID NO: 21) | – | 0 |
| M20 | Y | H | D | D | P | Y | (SEQ ID NO: 10) | –/+ | + |
| M21 | Y | Y | D | D | H | H | (SEQ ID NO: 22) | – | 0 |
| M24 | D | L | G | D | H | Y | (SEQ ID NO: 23) | – | 0 |
| M31 | Y | Y | E | G | R | Y | (SEQ ID NO: 11) | –/+ | + |
| M58 | Y | S | D | V | Y | Y | (SEQ ID NO: 12) | + | ++ |
| M64 | Y | Y | G | D | P | Y | (SEQ ID NO: 24) | – | 0 |
| M65 | Y | S | D | D | R | Y | (SEQ ID NO: 13) | +++ | + |
| M69 | Y | N | D | E | H | Y | (SEQ ID NO: 14) | + | ++ |
| M76 | Y | Y | D | D | N | Y | (SEQ ID NO: 15) | ++++ | + |
| M82 | N | Y | D | D | H | Y | (SEQ ID NO: 25) | – | 0 |

Accordingly, the present invention provides for specific mutants of antibodies, antibody constructs and in particular bispecific single chain molecules capable of interacting with/binding to CD3 and comprising a modified VH-CDR3 region.

Example 4

Dissociation of Mutant CD3 Bispecific Antibodies from CD3

To evaluate the stability of binding to CD3, T cells were stained with wildtype and CD3 mutant bispecific antibodies and dissociation was measured (FIG. 2).

T cells were stained with wildtype and CD3 mutant bispecific antibodies (M13 and M76 data showed decreased and increased binding, respectively) and measured for the dissociation of fluorescent complexes at 37° C. or at 18° C., in the presence of azide to prevent endocytosis (FIG. 2). Cells were resuspended in staining buffer containing 50 µg/ml anti-CD3 monoclonal antibody to avoid rebinding of CD3 mutant bispecific antibodies after dissociation. Dissociation of the mutant CD3 bispecific antibodies from T cells was measured using a thermostatic cuvette by FACS analysis as decrease of GMFI at progressive time points.

Dissociation was faster at 37° C. than at 18° C. and the two mutants showed opposite behaviour. When compared to the wild type, M76 dissociated more slowly while M13 was faster.

Example 5

Mutant CD3 Bispecific Antibodies with Less Stable Binding to CD3 are More Efficient in T Cell Activation To investigate how the binding affinity for the TCR/CD3 complex may affect T cell stimulatory capacity, expression vectors for mutant CD3 bispecific antibodies were constructed (Example 1). After sequencing, mutants were expressed in DHFR deficient CHO cells as described (Mack et al. 1995, PNAS 92, 7021-7025; Mack et al. 1997, Immunity 4, 565-571) and tested for their capacity to bind to CD3 and activate human T cells in the presence of EpCAM+ Kato-3 tumor cell line (Example 1, Table 1 and FIG. 1).

EpCAM+ Kato-3 tumor cells were incubated with different dilutions of WT and mutant CD3 bispecific antibodies starting from a concentration that gives identical levels of staining. Due to an identical EpCAM binding site in all mutants, the number of bispecific molecules per tumor cell should be constant and differences in T cell stimulatory capacity should be attributed only to differences in TCR triggering capacity of the individual mutant CD3 bispecific antibodies. As readout for T cell activation upregulation of CD69 and CD25 in naïve T cells or induction of IFN-γ secretion in T cell blasts were measured. For this reason Kato-3 cells were incubated for 2 hours at 4° C. with different dilutions of supernatants from mutant CD3 bispecific antibodies and washed twice with cold PBS. To evaluate the capacity to induce CD69 and CD25 upregulation in naïve T cells, pulsed Kato-3 cells were cultured for 20 hours at 37° C. with peripheral blood naïve CD4+ T cells. Cells were stained with monoclonal antibodies against CD69 and CD25 (Pharmingen) followed by PE-conjugated anti-mouse Ig (Southern Biotechnologies). FACS analysis was performed excluding Kato-3 cells via forward and side scattering. Results are shown in FIG. 3A.

To evaluate the induction of IFN-γ production pulsed Kato-3 cells were cultured for 6 hours at 37° C. with T cell blasts in the presence of Brefeldin A, fixed and permeabilized and stained with antibodies to CD69 and IFN-γ (Pharmingen) (FIG. 3B).

Three mutants (M13, M58 and M69) showed a markedly decreased binding to T cells, but were still efficient in triggering CD69 upregulation. Furthermore one mutant (M76) showed increased binding, but a reduced capacity to induce CD69 upregulation (Tab. 1). The slopes of WT and mutant CD3 bispecific antibodies were consistently different in FIG. 3. The low affinity mutant M13 showed a rather, flat slope similar to that of the wild type. In contrast the high affinity mutant M76 rapidly lost T cell stimulatory capacity as a function of dilution.

Example 6

Mutated CD3 Bispecific Antibodies with Less Stable Binding of CD3 are more efficient in T Cell Activation, Especially when Present at Low Copy Number on Target Cells Cells from an influenza virus-specific CTL clone were cultured with EpCAM+ tumor cells coated with serial dilutions of wild type or mutant CD3 bispecific antibodies as above. Killing of tumor cells was measured by FACS analysis after 5 hours at 37° C. by staining with annexin V and propidium iodide to visualise apoptotic and necrotic cells. As shown in FIG. 4, the high affinity M76 mutant induced cytotoxicity only at the highest doses and rapidly lost efficacy upon dilution. In contrast, the low affinity M13 mutant, although slightly less potent than the wild type, remained effective even at highest dilution.

In summary, particular mutated CD3 bispecific antibodies with less stable binding to CD3 are more efficient in T cell activation, especially when present at low copy number on target cells. These specific bispecific antibody molecules comprise a modified YYDDHY-motif as shown in mutant M13, M58 or M69.

Example 7

Exemplified Construction of a Bispecific Single Chain Antibody Anti-EpCAM×Anti-CD3

The Flag-less version of scFV EpCAM×CD3 was prepared from the original construct described by Mack, 1995, PNAS, 92, 7021-7025 by PCR based deletion of the Flag-specific nucleotides. This construct is based on the VL and VH domains of an anti-EpCAM antibody from the M79 hybridoma (anti-17-1A, Göttlinger, 1986, Int. J. Cancer, 38, 47-53) which were cloned according to the standard PCR methods as described by Orlandi, 1989, PNAS, 86, 3833-3837. cDNA synthesis was carried out with random hexamers (Boehringer Mannheim) and SuperScript reverse transcriptase (Gibco). For amplification of the V domains via PCR with Pfu polymerase, two primers 5'light Eco5 and 3'light Bgl2 were used, flanking the light chain and 5'heavy Eco5 and 3'heavy BspE1, flanking the heavy chain. Two independent clones of each V domain were sequenced and compared for identity.

Construction of the anti CD3 part had also been disclosed in PCT/EP99/02693 (Kufer).

VL and VH cDNA isolated from M79 hybridoma were joined to a single chain fragment using standard $(Gly_4\text{-}Ser_1)_3$ linker. For this purpose, a two-step fusion PCR (Pfu polymerase) was performed. The first PCR step introduced a 3'-terminal $(Gly_4\text{-}Ser_1)_2$ coding sequence into VL with the two primers 5' light-Eco5 and 3' lightLinker and a 5'-terminal $(Gly_4\text{-}Ser_1)_2$ coding sequence into VH with the primers 5' heavyLinker and 3' heavyBspE1. The purified amplification products of VL and VH were used for the second step fusion PCR (8 cycles) with the primers 5' lightEco5 and 3' heavyBspE1. The resulting PCR fragment of the single chain molecule was subcloned (EcoRV and BspE1) into a bacterial expression vector and sequenced. The vector for periplasmic expression in bacteria, provided by A. Plückthun (Zürich), consists of an isopropyl-β-D-thiogalactopyranoside-inducible lac promoter, the periplasmic signal sequence OmpA and a 5'-terminal Flag epitope for detection. The periplasmic expression in *E. coli* strain JM83 was performed according to the procedure described by Pluckthun et al. (Pluckthun, 1989, Methods Enzymol. 178, 497-515).

List of Primers:

```
5'light Eco5:
5'aagatatccagctgacccagtctcca 3'                                    (SEQ ID NO: 44)

3'lightBgl2:
5'gttagatctcgagcttggtccc 3'                                        (SEQ ID NO: 45)

5'heavy Eco5:
5'aagatatcaggtsmarctgcagsagtcwgg 3'                                (SEQ ID NO: 46)

s = c or g; m = a or c; r = a or g; w = a or t

3'heavy BspE1:
5'aatccggaggagacggtgaccgtggtccttggccccag 3'                        (SEQ ID NO: 47)

3'light linker:
5'ggagccgccgccgccagaaccaccaccacctttgatctcgagcttggtccc 3'           (SEQ ID NO: 48)

5'heavy linker:
5'ggcggcggcggctccggtggtggtggttctcaggtgaaactgcaggagtc 3'            (SEQ ID NO: 49)
```

```
5'heavy CD3 linker 5:
5'taatccggaggtggtggatccgatatcaaactgcagcagtcagg 3'                                       (SEQ ID NO: 50)

5'heavy CD3 linker 15:
5'taatccggaggtggtggttccggggtggtggttccggggtggtggatccgatatcaaactgcagcagtcag              (SEQ ID NO: 51)
g 3'

3'light CD3His:
5'tttaagcttgtcgactaatgatgatggtgatgatgtttcagctccagcttggtcccagc 3'                        (SEQ ID NO: 52)
```

Construction of the bispecific single chain antibody was performed in three steps.

1. To introduce the $Gly_4$-$Ser_1$ or $(Gly_4$-$Ser_1)_3$ linker sequences between the VH regions of the anti-EpCAM scFv fragment and the anti-CD3 scFv fragment and in order to add a 3'-terminal histidine tail, a PCR fragment of the anti-CD3 scFv fragment DNA was generated with the two primers 5'heavyCD3linker5 and 5'heavyCD3linker15 and with 3'lightCD3His (Taq polymerase) and subcloned with the BspE1 and HindIII restrictions enzymes into the vector already containing the anti-EpCAM scFv fragment.
2. A synthetic DNA oligodimer (5'leader Flag and 3'leader Flag) coding for a eucaryotic secretory signal sequence together with the Flag epitope was subcloned into the same vector with the XbaI and EcoRV enzymes.
3. Finally the scFv antibody fragment was subcloned into a eucaryotic expression vector. This vector contained the promoter of human elongation factor 1a, kindly provided by S. Nagata (Mizushima, 1990, Nucleic Acid Res, 18, 5322-5323), followed by a multiple cloning site and an internal ribosomal binding site (Pelletier, 1988, Nature (London), 334, 320-325), which allows bicistronic expression of the construct and dihydrofolate reductase (DHFR) used as a selection marker. The expression was performed in DHFR-deficient CHO cells as described by Kaufman (1990, Methods Enzymol., 185, 537-566). The cells were transfected by electroporation and grown for selection in nucleotide free α-MEM supplemented with dialyzed 10% fetal calf serum (Gibco) and 2 mM L-glutamine. To increase the expression rate by gene amplification, the transfectants were subsequently exposed to 20 nm methotrexate.

ScFv anti-EpCAM×anti-CD3 was purified as described by Mack (PNAS, 1995, 92, 7021-7025). For this purpose CHO DHFR-cells stably transfected with the scFv EpCAM×CD3 construct were grown for 6 days in roller bottles in αMEM medium with 10% FCS. 200 ml cell culture supernatant containing scFv anti-EpCAM×anti-CD3 was collected, clarified by centrifugation for 30 min. at 4000 rpm (Rotina 46R) and sterile filtered (Vacucap 90). A 5 ml HisTrap column (Pharmacia) was performed according to the manufacturer's protocol and cell culture supernatant was applied. The column was washed with 20 mM sodium phosphate containing 400 mM sodium chloride pH 7.2. Protein bound unspecifically was removed with 100 mM imidazole in 20 mM sodium phosphate and 400 mM sodium chloride pH 6. scFv anti-EpCAM×anti-CD3 was eluted with 200 mM Imidazole in 20 mM sodium phosphate and 400 mM sodium chloride pH.

The elution peak had a volume of 9 ml and was concentrated 18fold with a 10 kD MicroSep concentration unit (Pall). 250 µl of the concentrate were separated by analytical gelfiltration on a 2× Superdex 200 HR 10/30 (Pharmacia) equilibrated with PBS. Separation was performed with PBS at a flow rate of 0.7 ml/min.

Amino Acid Sequence of Anti EpCAM VH:

```
GlnValLysLeuGlnGluSerGlyProGlyLeuValGlnProSerGlnSerLeuSerIleThrCysThrVa      (SEQ ID NO: 53)

lSerGlyPheSerLeuThrSerTyrGlyValHisTrpValArgGlnSerProGlyLysGlyLeuGluTrpL euGlyValIleTrpSerGlyGlySerThrAspTyrAsnAlaAlaPheIleSerArgLeuSerIleSerLysAs pAsnSerLysSerGlnValPhePheLysMetAsnSerLeuGlnAlaAsnAspThrAlaIleTyrTyrCy sAlaArgMetGluAsnTrpSerPheAlaTyrTrpGlyGlnGlyThrThrValThrValSerSer
```

Nucleotide Sequence of Anti EpCAM VH:

```
CAGGTGAAACTGCAGGAGTCAGGACCTGGCCTAGTGCAGCCCTCACAGAGC          (SEQ ID NO: 54)

CTGTCCATCACCTGCACAGTCTCTGGTTTCTCATTAACTAGCTATGGTGTACAC

TGGGTTCGCCAGTCTCCAGGAAAGGGTCTGGAGTGGCTGGGAGTGATATGG

AGTGGTGGAAGCACAGACTATAATGCAGCTTTCATATCCAGACTGAGCATCAG

CAAGGACAATTCCAAGAGCCAAGTTTTCTTTAAAATGAACAGTCTGCAAGCTA

ATGACACAGCCATATATTACTGTGCCAGAATGGAGAACTGGTCGTTTGCTTACT

GGGGCCAAGGGACCACGGTCACCGTCTCCTCC
```

Amino Acid Sequence of Anti EpCAM VL:

AspIleGlnLeuThrGlnSerGlnLysPheMetSerThrSerValGlyAspArgValSerValThrCysL    (SEQ ID NO: 55)
ysAlaSerGlnAsnValGlyThrAsnValAlaTrpTyrGlnGlnLysProGlyGlnSerProLysAlaLeuI
leTyrSerAlaSerTyrArgTyrSerGlyValProAspArgPheThrGlySerGlySerGlyThrAspPhe
ThrLeuThrIleSerAsnValGlnSerGluAspLeuAlaGluTyrPheCysGlnGlnTyrAsnSerTyrP
roLeuThrPheGlyAlaGlyThrLysLeuGluIleLys

Nucleotide Sequence of Anti EpCAM VL:

GATATCCAGCTGACCCAGTCTCAAAAATTCATGTCCACATCAGTAGGAGACAG    (SEQ ID NO: 56)
GGTCAGCGTCACCTGCAAGGCCAGTCAGAATGTGGGTACTAATGTAGCCTGG
TATCAACAGAAACCAGGGCAATCTCCTAAAGCACTGATTTACTCGGCATCCTA
CCGGTACAGTGGAGTCCCTGATCGCTTCACAGGCAGTGGATCTGGGACAGAT
TTCACTCTCACCATCAGCAATGTGCAGTCTGAAGACTTGGCAGAGTATTTCTG
TCAGCAATATAACAGCTATCCGCTCACGTTCGGTGCTGGGACCAAGCTCGAG
ATCAAA

Amino Acid Sequence Anti-CD3 VH (Modified Anti-CD3 $V_H$-Region Derived from OKT-3):

AspIleLysLeuGlnGlnSerGlyAlaGluLeuAlaArgProGlyAlaSerValLysMetSerCysLysTh    (SEQ ID NO: 57)
rSerGlyTyrThrPheThrArgTyrThrMetHisTrpValLysGlnArgProGlyGlnGlyLeuGluTrpIl
eGlyTyrIleAsnProSerArgGlyTyrThrAsnTyrAsnGlnLysPheLysAspLysAlaThrLeuThr
ThrAspLysSerSerSerThrAlaTyrMetGlnLeuSerSerLeuThrSerGluAspSerAlaValTyrT
yrCysAlaArg<u>TyrTyrAspAspHisTyr</u>CysLeuAspTyrTrpGlyGlnGlyThrThrLeuThrValSer
SerValGlu
Motif (SEQ ID NO: 1) of claim 1 is underlined.

Nucleotide Sequence Anti-CD3 VH (Modified Anti-CD3 $V_H$-Region Derived from OKT-3):

GATATCAAACTGCAGCAGTCAGGGGCTGAACTGGCAAGACCTGGGGCCTCG    (SEQ ID NO: 58)
TGAAGATGTCCTGCAAGACTTCTGGCTACACCTTTACTAGGTACACGATGCAC
TGGGTAAAACAGAGGCCTGGACAGGGTCTGGAATGGATTGGATACATTAATCC
TAGCCGTGGTTATACTAATTACAATCAGAAGTTCAAGGACAAGGCCACATTGA
CTACAGACAAATCCTCCAGCACAGCCTACATGCAACTGAGCAGCCTGACATCT
GAGGACTCTGCAGTCTATTACTGTGCAAGATATTATGATGATCATTACTGCCTT
GACTACTGGGGCCAAGGCACCACTCTCACAGTCTCCTCAGTCGAA

Accordingly, and as illustrated herein, further modifications in anti-CD3 region, in particular in the $V_H$-region may be carried out. As shown here, the $V_H$-anti-CD3-region of OKT-3 may be modified by introducing an substituted YYD-DHY-motif as documented herein and additional modifications like the addition of VE the substitution of QVQ by DIK, or the substitution of A by T.

Amino Acid Sequence of scFv EpCAM×CD3 (Modified Anti-CD3 V$_H$-Region Derived from OKT-3):

```
AspIleGlnLeuThrGlnSerGlnLysPheMetSerThrSerValGlyAspArgValSerValThrCysLysAla     (SEQ ID NO: 59)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArgTyrTyrAspAspHisTyrCysLeuAspTyrTrpG
lyGlnGlyThrThrLeuThrValSerSerValGluGlyGlySerGlyGlySerGlyGlySerGlyGlySerGlyGly
ValAspAspIleGlnLeuThrGlnSerProAlaIleMetSerAlaSerProGlyGluLysValThrMetThrCysA
rgAlaSerSerSerValSerTyrMetAsnTrpTyrGlnGlnLysSerGlyThrSerProLysArgTrpIleTyrAsp
ThrSerLysValAlaSerGlyValProTyrArgPheSerGlySerGlySerGlyThrSerTyrSerLeuThrIleSe
rSerMetGluAlaGluAspAlaAlaThrTyrTyrCysGlnGlnTrpSerSerAsnProLeuThrPheGlyAlaGl
yThrLysLeuGluLeuLysHisHisHisHisHisHis
```

Nucleotide Sequence of scFv EpCAM×CD3 (Modified Anti-CD3 V$_H$-Region Derived from OKT-3):

```
GATATCCAGCTGACCCAGTCTCAAAAATTCATGTCCACATCAGTAGGAGACA     (SEQ ID NO: 60)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
GTTCTCAGGTGAAACTGCAGGAGTCAGGACCTGGCCTAGTGCAGCCCTCAC
AGAGCCTGTCCATCACCTGCACAGTCTCTGGTTTCTCATTAACTAGCTATGGT
GTACACTGGGTTCGCCAGTCTCCAGGAAAGGGTCTGGAGTGGCTGGGAGTG
ATATGGAGTGGTGGAAGCACAGACTATAATGCAGCTTTCATATCCAGACTGA
GCATCAGCAAGGACAATTCCAAGAGCCAAGTTTTCTTTAAAATGAACAGTCTG
CAAGCTAATGACACAGCCATATATTACTGTGCCAGAATGGAGAACTGGTCGT
TTGCTTACTGGGGCCAAGGGACCACGGTCACCGTCTCCTCCGGAGGTGGTG
GATCCGATATCAAACTGCAGCAGTCAGGGGCTGAACTGGCAAGACCTGGGG
```

```
CCTCAGTGAAGATGTCCTGCAAGACTTCTGGCTACACCTTTACTAGGTACAC

GATGCACTGGGTAAAACAGAGGCCTGGACAGGGTCTGGAATGGATTGGATA

CATTAATCCTAGCCGTGGTTATACTAATTACAATCAGAAGTTCAAGGACAAGG

CCACATTGACTACAGACAAATCCTCCAGCACAGCCTACATGCAACTGAGCAG

CCTGACATCTGAGGACTCTGCAGTCTATTACTGTGCAAGATATTATGATGATC

ATTACTGCCTTGACTACTGGGGCCAAGGCACCACTCTCACAGTCTCCTCAGT

CGAAGGTGGAAGTGGAGGTTCTGGTGGAAGTGGAGGTTCAGGTGGAGTCGA

CGACATTCAGCTGACCCAGTCTCCAGCAATCATGTCTGCATCTCCAGGGGAG

AAGGTCACCATGACCTGCAGAGCCAGTTCAAGTGTAAGTTACATGAACTGGT

ACCAGCAGAAGTCAGGCACCTCCCCCAAAAGATGGATTTATGACACATCCAA

AGTGGCTTCTGGAGTCCCTTATCGCTTCAGTGGCAGTGGGTCTGGGACCTC

ATACTCTCTCACAATCAGCAGCATGGAGGCTGAAGATGCTGCCACTTATTAC

TGCCAACAGTGGAGTAGTAACCCGCTCACGTTCGGTGCTGGGACCAAGCTG

GAGCTGAAACATCATCACCATCATCATTAG
```

In accordance with the example provided herein above, the person skilled in the art is readily in a position to modify constructs as, inter alia, shown in SEQ ID NO: 59 by replacing the underlined sequence (SEQ ID NO: 1) by any of the sequences as defined herein and in particular the sequences shown in SEQ ID NOs: 2, 3, 4, 5, 6, 7, 8, 9, 10, 11, 12, 13, 14 or 15.

As particular example, the following constructs are provided:

Amino Acid Sequence of an scFv Anti EpCAM×Anti CD3 with M1 Mutant in Anti CD3 Part:

```
AspIleGlnLeuThrGlnSerGlnLysPheMetSerThrSerValGlyAspArgValSerValThrCysLysAla       (SEQ ID NO: 61)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArgHisTyrAspAspHisTyrCysLeuAspTyrTrpG
lyGlnGlyThrThrLeuThrValSerSerValGluGlyGlySerGlyGlySerGlyGlySerGlyGlySerGlyGly
ValAspAspIleGlnLeuThrGlnSerProAlaIleMetSerAlaSerProGlyGluLysValThrMetThrCysA
rgAlaSerSerSerValSerTyrMetAsnTrpTyrGlnGlnLysSerGlyThrSerProLysArgTrpIleTyrAsp
ThrSerLysValAlaSerGlyValProTyrArgPheSerGlySerGlySerGlyThrSerTyrSerLeuThrIleSe
rSerMetGluAlaGluAspAlaAlaThrTyrTyrCysGlnGlnTrpSerSerAsnProLeuThrPheGlyAlaGl
yThrLysLeuGluLeuLysHisHisHisHisHisHis
```

Nucleotide Sequence Coding for scFv EpCAM×CD3 with M1 Mutant:

```
GATATCCAGCTGACCCAGTCTCAAAAATTCATGTCCACATCAGTAGGAGACA    (SEQ ID NO: 62)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
GTTCTCAGGTGAAACTGCAGGAGTCAGGACCTGGCCTAGTGCAGCCCTCAC
AGAGCCTGTCCATCACCTGCACAGTCTCTGGTTTCTCATTAACTAGCTATGGT
GTACACTGGGTTCGCCAGTCTCCAGGAAAGGGTCTGGAGTGGCTGGGAGTG
ATATGGAGTGGTGGAAGCACAGACTATAATGCAGCTTTCATATCCAGACTGA
GCATCAGCAAGGACAATTCCAAGAGCCAAGTTTTCTTTAAAATGAACAGTCTG
CAAGCTAATGACACAGCCATATATTACTGTGCCAGAATGGAGAACTGGTCGT
TTGCTTACTGGGGCCAAGGGACCACGGTCACCGTCTCCTCCGGAGGTGGTG
GATCCGATATCAAACTGCAGCAGTCAGGGGCTGAACTGGCAAGACCTGGGG
CCTCAGTGAAGATGTCCTGCAAGACTTCTGGCTACACCTTTACTAGGTACAC
GATGCACTGGGTAAAACAGAGGCCTGGACAGGGTCTGGAATGGATTGGATA
CATTAATCCTAGCCGTGGTTATACTAATTACAATCAGAAGTTCAAGGACAAGG
CCACATTGACTACAGACAAATCCTCCAGCACAGCCTACATGCAACTGAGCAG
CCTGACATCTGAGGACTCTGCAGTCTATTACTGTGCAAGACATTATGATGATC
ATTACTGCCTTGACTACTGGGGCCAAGGCACCACTCTCACAGTCTCCTCAGT
CGAAGGTGGAAGTGGAGGTTCTGGTGGAAGTGGAGGTTCAGGTGGAGTCGA
CGACATTCAGCTGACCCAGTCTCCAGCAATCATGTCTGCATCTCCAGGGGAG
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

Amino Acid Sequence of scFv Anti EpCAM×Anti CD3 with M4 Mutant in Anti CD3 Part:

```
AspIleGlnLeuThrGlnSerGlnLysPheMetSerThrSerValGlyAspArgValSerValThrCysLysAla    (SEQ ID NO: 63)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
```

-continued uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArg<u>TyrSerAspAspHisTyr</u>CysLeuAspTyrTrp
GlyGlnGlyThrThrLeuThrValSerSerValGluGlyGlySerGlyGlySerGlyGlySerGlyGlySerGlyGl
yValAspAspIleGlnLeuThrGlnSerProAlaIleMetSerAlaSerProGlyGluLysValThrMetThrCys
ArgAlaSerSerSerValSerTyrMetAsnTrpTyrGlnGlnLysSerGlyThrSerProLysArgTrpIleTyrA
spThrSerLysValAlaSerGlyValProTyrArgPheSerGlySerGlySerGlyThrSerTyrSerLeuThrIle
SerSerMetGluAlaGluAspAlaAlaThrTyrTyrCysGlnGlnTrpSerSerAsnProLeuThrPheGlyAla
GlyThrLysLeuGluLeuLysHisHisHisHisHisHis Nucleotide Sequence Coding for scFv EpCAM×CD3 with M4 Mutant:

```
GATATCCAGCTGACCCAGTCTCAAAAATTCATGTCCACATCAGTAGGAGACA    (SEQ ID NO: 64)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
GTTCTCAGGTGAAACTGCAGGAGTCAGGACCTGGCCTAGTGCAGCCCTCAC
AGAGCCTGTCCATCACCTGCACAGTCTCTGGTTTCTCATTAACTAGCTATGGT
GTACACTGGGTTCGCCAGTCTCCAGGAAAGGGTCTGGAGTGGCTGGGAGTG
ATATGGAGTGGTGGAAGCACAGACTATAATGCAGCTTTCATATCCAGACTGA
GCATCAGCAAGGACAATTCCAAGAGCCAAGTTTTCTTTAAAATGAACAGTCTG
CAAGCTAATGACACAGCCATATATTACTGTGCCAGAATGGAGAACTGGTCGT
TTGCTTACTGGGGCCAAGGGACCACGGTCACCGTCTCCTCCGGAGGTGGTG
GATCCGATATCAAACTGCAGCAGTCAGGGGCTGAACTGGCAAGACCTGGGG
CCTCAGTGAAGATGTCCTGCAAGACTTCTGGCTACACCTTTACTAGGTACAC
GATGCACTGGGTAAAACAGAGGCCTGGACAGGGTCTGGAATGGATTGGATA
CATTAATCCTAGCCGTGGTTATACTAATTACAATCAGAAGTTCAAGGACAAGG
CCACATTGACTACAGACAAATCCTCCAGCACAGCCTACATGCAACTGAGCAG
CCTGACATCTGAGGACTCTGCAGTCTATTACTGTGCAAGA<u>TATAGTGATGATC
ATTAC</u>TGCCTTGACTACTGGGGCCAAGGCACCACTCTCACAGTCTCCTCAGT
CGAAGGTGGAAGTGGAGGTTCTGGTGGAAGTGGAGGTTCAGGTGGAGTCGA
CGACATTCAGCTGACCCAGTCTCCAGCAATCATGTCTGCATCTCCAGGGGAG
```

-continued

```
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

Amino Acid Sequence of scFv Anti EpCAM×Anti CD3 with M7 Mutant in Anti CD3 Part:

AspIleGlnLeuThrGlnSerGlnLysPheMetSerThrSerValGlyAspArgValSerValThrCysLysAla (SEQ ID NO: 65)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArg<u>TyrTyrAspAlaHisTyr</u>CysLeuAspTyrTrpGl
yGlnGlyThrThrLeuThrValSerSerValGluGlyGlySerGlyGlySerGlyGlySerGlyGlySerGlyGly
ValAspAspIleGlnLeuThrGlnSerProAlaIleMetSerAlaSerProGlyGluLysValThrMetThrCysA
rgAlaSerSerSerValSerTyrMetAsnTrpTyrGlnGlnLysSerGlyThrSerProLysArgTrpIleTyrAsp
ThrSerLysValAlaSerGlyValProTyrArgPheSerGlySerGlySerGlyThrSerTyrSerLeuThrIleSe
rSerMetGluAlaGluAspAlaAlaThrTyrTyrCysGlnGlnTrpSerSerAsnProLeuThrPheGlyAlaGl
yThrLysLeuGluLeuLysHisHisHisHisHisHis

50

Nucleotide Sequence Coding for scFv EpCAM×CD3 with M7 Mutant:

```
GATATCCAGCTGACCCAGTCTCAAAAATTCATGTCCACATCAGTAGGAGACA    (SEQ ID NO. 66)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
```

```
GTTCTCAGGTGAAACTGCAGGAGTCAGGACCTGGCCTAGTGCAGCCCTCAC

AGAGCCTGTCCATCACCTGCACAGTCTCTGGTTTCTCATTAACTAGCTATGGT

GTACACTGGGTTCGCCAGTCTCCAGGAAAGGGTCTGGAGTGGCTGGGAGTG

ATATGGAGTGGTGGAAGCACAGACTATAATGCAGCTTTCATATCCAGACTGA

GCATCAGCAAGGACAATTCCAAGAGCCAAGTTTTCTTTAAAATGAACAGTCTG

CAAGCTAATGACACAGCCATATATTACTGTGCCAGAATGGAGAACTGGTCGT

TTGCTTACTGGGGCCAAGGGACCACGGTCACCGTCTCCTCCGGAGGTGGTG

GATCCGATATCAAACTGCAGCAGTCAGGGGCTGAACTGGCAAGACCTGGGG

CCTCAGTGAAGATGTCCTGCAAGACTTCTGGCTACACCTTTACTAGGTACAC

GATGCACTGGGTAAAACAGAGGCCTGGACAGGGTCTGGAATGGATTGGATA

CATTAATCCTAGCCGTGGTTATACTAATTACAATCAGAAGTTCAAGGACAAGG

CCACATTGACTACAGACAAATCCTCCAGCACAGCCTACATGCAACTGAGCAG

CCTGACATCTGAGGACTCTGCAGTCTATTACTGTGCAAGATATTATGATGCTC

ATTACTGCCTTGACTACTGGGGCCAAGGCACCACTCTCACAGTCTCCTCAGT

CGAAGGTGGAAGTGGAGGTTCTGGTGGAAGTGGAGGTTCAGGTGGAGTCGA

CGACATTCAGCTGACCCAGTCTCCAGCAATCATGTCTGCATCTCCAGGGGAG

AAGGTCACCATGACCTGCAGAGCCAGTTCAAGTGTAAGTTACATGAACTGGT

ACCAGCAGAAGTCAGGCACCTCCCCCAAAAGATGGATTTATGACACATCCAA

AGTGGCTTCTGGAGTCCCTTATCGCTTCAGTGGCAGTGGGTCTGGGACCTC

ATACTCTCTCACAATCAGCAGCATGGAGGCTGAAGATGCTGCCACTTATTAC

TGCCAACAGTGGAGTAGTAACCCGCTCACGTTCGGTGCTGGGACCAAGCTG

GAGCTGAAACATCATCACCATCATCATTAG
```

Amino Acid Sequence of scFv Anti EpCAM×Anti CD3 with M9 Mutant in Anti CD3 Part:

```
AspIleGlnLeuThrGlnSerGlnLysPheMetSerThrSerValGlyAspArgValSerValThrCys   (SEQ ID NO: 67)

LysAlaSerGlnAsnValGlyThrAsnValAlaTrpTyrGlnGlnLysProGlyGlnSerProLysAla

LeuIleTyrSerAlaSerTyrArgTyrSerGlyValProAspArgPheThrGlySerGlySerGlyThr

AspPheThrLeuThrIleSerAsnValGlnSerGluAspLeuAlaGluTyrPheCysGlnGlnTyrAsn

SerTyrProLeuThrPheGlyAlaGlyThrLysLeuGluIleLysGlyGlyGlyGlySerGlyGlyGly

GlySerGlyGlyGlyGlySerGlnValLysLeuGlnGluSerGlyProGlyLeuValGlnProSerGln

SerLeuSerIleThrCysThrValSerGlyPheSerLeuThrSerTyrGlyValHisTrpValArgGln

SerProGlyLysGlyLeuGluTrpLeuGlyValIleTrpSerGlyGlySerThrAspTyrAsnAlaAla

PheIleSerArgLeuSerIleSerLysAspAsnSerLysSerGlnValPhePheLysMetAsnSerLeu

GlnAlaAsnAspThrAlaIleTyrTyrCysAlaArgMetGluAsnTrpSerPheAlaTyrTrpGlyGln

GlyThrThrValThrValSerSerGlyGlyGlyGlySerAspIleLysLeuGlnGlnSerGlyAlaGlu

LeuAlaArgProGlyAlaSerValLysMetSerCysLysThrSerGlyTyrThrPheThrArgTyrThr

MetHisTrpValLysGlnArgProGlyGlnGlyLeuGluTrpIleGlyTyrIleAsnProSerArgGly

TyrThrAsnTyrAsnGlnLysPheLysAspLysAlaThrLeuThrThrAspLysSerSerSerThrAla

TyrMetGlnLeuSerSerLeuThrSerGluAspSerAlaValTyrTyrCysAlaArg
```

-continued

<u>TyrTyrAspAspGlnTyr</u>CysLeuAspTyrTrpGlyGlnGlyThrThrLeuThrValSerSerValGlu
GlyGlySerGlyGlySerGlyGlySerGlyGlySerGlyGlyValAspAspIleGlnLeuThrGlnSer
ProAlaIleMetSerAlaSerProGlyGluLysValThrMetThrCysArgAlaSerSerSerValSer
TyrMetAsnTrpTyrGlnGlnLysSerGlyThrSerProLysArgTrpIleTyrAspThrSerLysVal
AlaSerGlyValProTyrArgPheSerGlySerGlySerGlyThrSerTyrSerLeuThrIleSerSer
MetGluAlaGluAspAlaAlaThrTyrTyrCysGlnGlnTrpSerSerAsnProLeuThrPheGlyAla
GlyThrLysLeuGluLeuLysHisHisHisHisHisHis

Nucleotide Sequence Coding for scFv Anti EpCAM×anti CD3 with M9 Mutant in Anti CD3 Part: [15]

```
GATATCCAGCTGACCCAGTCTCAAAAATTCATGTCCACATCAGTAGGAGACA    (SEQ ID NO. 68)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
GTTCTCAGGTGAAACTGCAGGAGTCAGGACCTGGCCTAGTGCAGCCCTCAC
AGAGCCTGTCCATCACCTGCACAGTCTCTGGTTTCTCATTAACTAGCTATGGT
GTACACTGGGTTCGCCAGTCTCCAGGAAAGGGTCTGGAGTGGCTGGGAGTG
ATATGGAGTGGTGGAAGCACAGACTATAATGCAGCTTTCATATCCAGACTGA
GCATCAGCAAGGACAATTCCAAGAGCCAAGTTTTCTTTAAAATGAACAGTCTG
CAAGCTAATGACACAGCCATATATTACTGTGCCAGAATGGAGAACTGGTCGT
TTGCTTACTGGGGCCAAGGGACCACGGTCACCGTCTCCTCCGGAGGTGGTG
GATCCGATATCAAACTGCAGCAGTCAGGGGCTGAACTGGCAAGACCTGGGG
CCTCAGTGAAGATGTCCTGCAAGACTTCTGGCTACACCTTTACTAGGTACAC
GATGCACTGGGTAAAACAGAGGCCTGGACAGGGTCTGGAATGGATTGGATA
CATTAATCCTAGCCGTGGTTATACTAATTACAATCAGAAGTTCAAGGACAAGG
CCACATTGACTACAGACAAATCCTCCAGCACAGCCTACATGCAACTGAGCAG
CCTGACATCTGAGGACTCTGCAGTCTATTACTGTGCAAGA<u>TATTATGATGATC
AATAC</u>TGCCTTGACTACTGGGGCCAAGGCACCACTCTCACAGTCTCCTCAGT
CGAAGGTGGAAGTGGAGGTTCTGGTGGAAGTGGAGGTTCAGGTGGAGTCGA
CGACATTCAGCTGACCCAGTCTCCAGCAATCATGTCTGCATCTCCAGGGGAG
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

Amino Acid Sequence of scFv Anti EpCAM×Anti CD3 with
M10 Mutant in Anti CD3 Part:

AspIleGlnLeuThrGlnSerGlnLysPheMetSerThrSerValGlyAspArgValSerValThrCysLysAla    (SEQ ID NO: 69)

SerGlnAsnValGlyThrAsnValAlaTrpTyrGlnGlnLysProGlyGlnSerProLysAlaLeuIleTyrSerAl aSerTyrArgTyrSerGlyValProAspArgPheThrGlySerGlySerGlyThrAspPheThrLeuThrIleSe rAsnValGlnSerGluAspLeuAlaGluTyrPheCysGlnGlnTyrAsnSerTyrProLeuThrPheGlyAla

GlyThrLysLeuGluIleLysGlyGlyGlyGlySerGlyGlyGlyGlySerGlyGlyGlyGlySerGlnValLysLe uGlnGluSerGlyProGlyLeuValGlnProSerGlnSerLeuSerIleThrCysThrValSerGlyPheSerLe uThrSerTyrGlyValHisTrpValArgGlnSerProGlyLysGlyLeuGluTrpLeuGlyValIleTrpSerGlyG lySerThrAspTyrAsnAlaAlaPheIleSerArgLeuSerIleSerLysAspAsnSerLysSerGlnValPheP heLysMetAsnSerLeuGlnAlaAsnAspThrAlaIleTyrTyrCysAlaArgMetGluAsnTrpSerPheAla

TyrTrpGlyGlnGlyThrThrValThrValSerSerGlyGlyGlyGlySerAspIleLysLeuGlnGlnSerGlyAl aGluLeuAlaArgProGlyAlaSerValLysMetSerCysLysThrSerGlyTyrThrPheThrArgTyrThrMe tHisTrpValLysGlnArgProGlyGlnGlyLeuGluTrpIleGlyTyrIleAsnProSerArgGlyTyrThrAsnTy rAsnGlnLysPheLysAspLysAlaThrLeuThrThrAspLysSerSerSerThrAlaTyrMetGlnLeuSerS erLeuThrSerGluAspSerAlaValTyrTyrCysAlaArg<u>TyrTyrAspAspProTyr</u>CysLeuAspTyrTrp

GlyGlnGlyThrThrLeuThrValSerSerValGluGlyGlySerGlyGlySerGlyGlySerGlyGlySerGlyGl yValAspAspIleGlnLeuThrGlnSerProAlaIleMetSerAlaSerProGlyGluLysValThrMetThrCys

ArgAlaSerSerSerValSerTyrMetAsnTrpTyrGlnGlnLysSerGlyThrSerProLysArgTrpIleTyrA spThrSerLysValAlaSerGlyValProTyrArgPheSerGlySerGlySerGlyThrSerTyrSerLeuThrIle

SerSerMetGluAlaGluAspAlaAlaThrTyrTyrCysGlnGlnTrpSerSerAsnProLeuThrPheGlyAla

GlyThrLysLeuGluLeuLysHisHisHisHisHisHis

Nucleotide Sequence Coding for scFv Anti EpCAM×Anti
CD3 with M10 Mutant in Anti CD3 Part:

GATATCCAGCTGACCCAGTCTCAAAAATTCATGTCCACATCAGTAGGAGACA    (SEQ ID NO: 70)

GGGTCAGCGTCACCTGCAAGGCCAGTCAGAATGTGGGTACTAATGTAGCCT

GGTATCAACAGAAACCAGGGCAATCTCCTAAAGCACTGATTTACTCGGCATC

CTACCGGTACAGTGGAGTCCCTGATCGCTTCACAGGCAGTGGATCTGGGAC

AGATTTCACTCTCACCATCAGCAATGTGCAGTCTGAAGACTTGGCAGAGTATT

TCTGTCAGCAATATAACAGCTATCCGCTCACGTTCGGTGCTGGGACCAAGCT

CGAGATCAAAGGTGGTGGTGGTTCTGGCGGCGGCGGCTCCGGTGGTGGTG

GTTCTCAGGTGAAACTGCAGGAGTCAGGACCTGGCCTAGTGCAGCCCTCAC

AGAGCCTGTCCATCACCTGCACAGTCTCTGGTTTCTCATTAACTAGCTATGGT

GTACACTGGGTTCGCCAGTCTCCAGGAAAGGGTCTGGAGTGGCTGGGAGTG

ATATGGAGTGGTGGAAGCACAGACTATAATGCAGCTTTCATATCCAGACTGA

GCATCAGCAAGGACAATTCCAAGAGCCAAGTTTTCTTTAAAATGAACAGTCTG

CAAGCTAATGACACAGCCATATATTACTGTGCCAGAATGGAGAACTGGTCGT

TTGCTTACTGGGGCCAAGGGACCACGGTCACCGTCTCCTCCGGAGGTGGTG

GATCCGATATCAAACTGCAGCAGTCAGGGGCTGAACTGGCAAGACCTGGGG

-continued

```
CCTCAGTGAAGATGTCCTGCAAGACTTCTGGCTACACCTTTACTAGGTACAC
GATGCACTGGGTAAAACAGAGGCCTGGACAGGGTCTGGAATGGATTGGATA
CATTAATCCTAGCCGTGGTTATACTAATTACAATCAGAAGTTCAAGGACAAGG
CCACATTGACTACAGACAAATCCTCCAGCACAGCCTACATGCAACTGAGCAG
CCTGACATCTGAGGACTCTGCAGTCTATTACTGTGCAAGATATTATGATGATC
CTTACTGCCTTGACTACTGGGGCCAAGGCACCACTCTCACAGTCTCCTCAGT
CGAAGGTGGAAGTGGAGGTTCTGGTGGAAGTGGAGGTTCAGGTGGAGTCGA
CGACATTCAGCTGACCCAGTCTCCAGCAATCATGTCTGCATCTCCAGGGGAG
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

Amino Acid Sequence of scFv Anti EpCAM×Anti CD3 with
M11 Mutant in Anti CD3 Part:

AspIleGlnLeuThrGlnSerGlnLysPheMetSerThrSerValGlyAspArgValSerValThrCysLysAla    (SEQ ID NO: 71)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArgTyrPheAsnAspHisTyrCysLeuAspTyrTrp
GlyGlnGlyThrThrLeuThrValSerSerValGluGlyGlySerGlyGlySerGlyGlySerGlyGlySerGlyGl
yValAspAspIleGlnLeuThrGlnSerProAlaIleMetSerAlaSerProGlyGluLysValThrMetThrCys
ArgAlaSerSerSerValSerTyrMetAsnTrpTyrGlnGlnLysSerGlyThrSerProLysArgTrpIleTyrA
spThrSerLysValAlaSerGlyValProTyrArgPheSerGlySerGlySerGlyThrSerTyrSerLeuThrIle
SerSerMetGluAlaGluAspAlaAlaThrTyrTyrCysGlnGlnTrpSerSerAsnProLeuThrPheGlyAla
GlyThrLysLeuGluLeuLysHisHisHisHisHisHis

Nucleotide Sequence Coding for scFv Anti EpCAM×anti CD3 with M11 Mutant in Anti CD3 Part:

```
GATATCCAGCTGACCCAGTCTCAAAAATTCATGTCCACATCAGTAGGAGACA    (SEQ ID NO. 72)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
GTTCTCAGGTGAAACTGCAGGAGTCAGGACCTGGCCTAGTGCAGCCCTCAC
AGAGCCTGTCCATCACCTGCACAGTCTCTGGTTTCTCATTAACTAGCTATGGT
GTACACTGGGTTCGCCAGTCTCCAGGAAAGGGTCTGGAGTGGCTGGGAGTG
ATATGGAGTGGTGGAAGCACAGACTATAATGCAGCTTTCATATCCAGACTGA
GCATCAGCAAGGACAATTCCAAGAGCCAAGTTTTCTTTAAAATGAACAGTCTG
CAAGCTAATGACACAGCCATATATTACTGTGCCAGAATGGAGAACTGGTCGT
TTGCTTACTGGGGCCAAGGGACCACGGTCACCGTCTCCTCCGGAGGTGGTG
GATCCGATATCAAACTGCAGCAGTCAGGGGCTGAACTGGCAAGACCTGGGG
CCTCAGTGAAGATGTCCTGCAAGACTTCTGGCTACACCTTTACTAGGTACAC
GATGCACTGGGTAAAACAGAGGCCTGGACAGGGTCTGGAATGGATTGGATA
CATTAATCCTAGCCGTGGTTATACTAATTACAATCAGAAGTTCAAGGACAAGG
CCACATTGACTACAGACAAATCCTCCAGCACAGCCTACATGCAACTGAGCAG
CCTGACATCTGAGGACTCTGCAGTCTATTACTGTGCAAGATATTTTAATGATC
ATTACTGCCTTGACTACTGGGGCCAAGGCACCACTCTCACAGTCTCCTCAGT
CGAAGGTGGAAGTGGAGGTTCTGGTGGAAGTGGAGGTTCAGGTGGAGTCGA
CGACATTCAGCTGACCCAGTCTCCAGCAATCATGTCTGCATCTCCAGGGGAG
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

Amino Acid Sequence of scFv Anti EpCAM×Anti CD3 with M13 Mutant in Anti CD3 part:

```
AspIleGlnLeuThrGlnSerGlnLysPheMetSerThrSerValGlyAspArgValSerValThrCysLysAla    (SEQ ID NO: 73)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
```

-continued uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArg<u>TyrTyrAsnAspGlnTyr</u>CysLeuAspTyrTrp
Gl -continued

```
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

Amino Acid Sequence of scFv Anti EpCAM×Anti CD3 with M14 Mutant in Anti CD3 Part:

AspIleGlnLeuThrGlnSerGlnLysPheMetSerThrSerValGlyAspArgValSerValThrCysLysAla  (SEQ ID NO: 75)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArg<u>TyrTyrAspAlaHisAsn</u>CysLeuAspTyrTrpG
lyGlnGlyThrThrLeuThrValSerSerValGluGlyGlySerGlyGlyGlySerGlyGlySerGlyGly
ValAspAspIleGlnLeuThrGlnSerProAlaIleMetSerAlaSerProGlyGluLysValThrMetThrCysA
rgAlaSerSerSerValSerTyrMetAsnTrpTyrGlnGlnLysSerGlyThrSerProLysArgTrpIleTyrAsp
ThrSerLysValAlaSerGlyValProTyrArgPheSerGlySerGlySerGlyThrSerTyrSerLeuThrIleSe
rSerMetGluAlaGluAspAlaAlaThrTyrTyrCysGlnGlnTrpSerSerAsnProLeuThrPheGlyAlaGl
yThrLysLeuGluLeuLysHisHisHisHisHisHis

50

Nucleotide Sequence Coding for scFv Anti EpCAM×Anti CD3 with M14 Mutant in Anti CD3 Part:

```
GATATCCAGCTGACCCAGTCTCAAAAATTCATGTCCACATCAGTAGGAGACA    (SEQ ID NO: 76)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
```

-continued
```
GTTCTCAGGTGAAACTGCAGGAGTCAGGACCTGGCCTAGTGCAGCCCTCAC

AGAGCCTGTCCATCACCTGCACAGTCTCTGGTTTCTCATTAACTAGCTATGGT

GTACACTGGGTTCGCCAGTCTCCAGGAAAGGGTCTGGAGTGGCTGGGAGTG

ATATGGAGTGGTGGAAGCACAGACTATAATGCAGCTTTCATATCCAGACTGA

GCATCAGCAAGGACAATTCCAAGAGCCAAGTTTTCTTTAAAATGAACAGTCTG

CAAGCTAATGACACAGCCATATATTACTGTGCCAGAATGGAGAACTGGTCGT

TTGCTTACTGGGGCCAAGGGACCACGGTCACCGTCTCCTCCGGAGGTGGTG

GATCCGATATCAAACTGCAGCAGTCAGGGGCTGAACTGGCAAGACCTGGGG

CCTCAGTGAAGATGTCCTGCAAGACTTCTGGCTACACCTTTACTAGGTACAC

GATGCACTGGGTAAAACAGAGGCCTGGACAGGGTCTGGAATGGATTGGATA

CATTAATCCTAGCCGTGGTTATACTAATTACAATCAGAAGTTCAAGGACAAGG

CCACATTGACTACAGACAAATCCTCCAGCACAGCCTACATGCAACTGAGCAG

CCTGACATCTGAGGACTCTGCAGTCTATTACTGTGCAAGATATTATGATGCTC

ATAATTGCCTTGACTACTGGGGCCAAGGCACCACTCTCACAGTCTCCTCAGT

CGAAGGTGGAAGTGGAGGTTCTGGTGGAAGTGGAGGTTCAGGTGGAGTCGA

CGACATTCAGCTGACCCAGTCTCCAGCAATCATGTCTGCATCTCCAGGGGAG

AAGGTCACCATGACCTGCAGAGCCAGTTCAAGTGTAAGTTACATGAACTGGT

ACCAGCAGAAGTCAGGCACCTCCCCCAAAAGATGGATTTATGACACATCCAA

AGTGGCTTCTGGAGTCCCTTATCGCTTCAGTGGCAGTGGGTCTGGGACCTC

ATACTCTCTCACAATCAGCAGCATGGAGGCTGAAGATGCTGCCACTTATTAC

TGCCAACAGTGGAGTAGTAACCCGCTCACGTTCGGTGCTGGGACCAAGCTG

GAGCTGAAACATCATCACCATCATCATTAG
```

Amino Acid Sequence of scFv Anti EpCAM×Anti CD3 with M20 Mutant in Anti CD3 Part:

```
AspIleGlnLeuThrGlnSerGlnLysPheMetSerThrSerValGlyAspArgValSerValThrCysLysAla      (SEQ ID NO: 77)

SerGlnAsnValGlyThrAsnValAlaTrpTyrGlnGlnLysProGlyGlnSerProLysAlaLeuIleTyrSerAl aSerTyrArgTyrSerGlyValProAspArgPheThrGlySerGlySerGlyThrAspPheThrLeuThrIleSe rAsnValGlnSerGluAspLeuAlaGluTyrPheCysGlnGlnTyrAsnSerTyrProLeuThrPheGlyAla

GlyThrLysLeuGluIleLysGlyGlyGlyGlySerGlyGlyGlyGlySerGlyGlyGlyGlySerGlnValLysLe uGlnGluSerGlyProGlyLeuValGlnProSerGlnSerLeuSerIleThrCysThrValSerGlyPheSerLe uThrSerTyrGlyValHisTrpValArgGlnSerProGlyLysGlyLeuGluTrpLeuGlyValIleTrpSerGlyG lySerThrAspTyrAsnAlaAlaPheIleSerArgLeuSerIleSerLysAspAsnSerLysSerGlnValPheP heLysMetAsnSerLeuGlnAlaAsnAspThrAlaIleTyrTyrCysAlaArgMetGluAsnTrpSerPheAla

TyrTrpGlyGlnGlyThrThrValThrValSerSerGlyGlyGlyGlySerAspIleLysLeuGlnGlnSerGlyAl aGluLeuAlaArgProGlyAlaSerValLysMetSerCysLysThrSerGlyTyrThrPheThrArgTyrThrMe tHisTrpValLysGlnArgProGlyGlnGlyLeuGluTrpIleGlyTyrIleAsnProSerArgGlyTyrThrAsnTy rAsnGlnLysPheLysAspLysAlaThrLeuThrThrAspLysSerSerSerThrAlaTyrMetGlnLeuSerS erLeuThrSerGluAspSerAlaValTyrTyrCysAlaArgTyrHisAspAspProTyrCysLeuAspTyrTrp

GlyGlnGlyThrThrLeuThrValSerSerValGluGlyGlySerGlyGlySerGlyGlySerGlyGlySerGlyGl
``` yValAspAspIleGlnLeuThrGlnSerProAlaIleMetSerAlaSerProGlyGluLysValThrMetThrCys

ArgAlaSerSerSerValSerTyrMetAsnTrpTyrGlnGlnLysSerGlyThrSerProLysArgTrpIleTyrA spThrSerLysValAlaSerGlyValProTyrArgPheSerGlySerGlySerGlyThrSerTyrSerLeuThrIle

SerSerMetGluAlaGluAspAlaAlaThrTyrTyrCysGlnGlnTrpSerSerAsnProLeuThrPheGlyAla

GlyThrLysLeuGluLeuLysHisHisHisHisHisHis

Nucleotide Sequence Coding for scFv Anti EpCAM×Anti CD3 with M20 Mutant in Anti CD3 Part:

```
GATATCCAGCTGACCCAGTCTCAAAAATTCATGTCCACATCAGTAGGAGACA      (SEQ ID NO: 78)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
GTTCTCAGGTGAAACTGCAGGAGTCAGGACCTGGCCTAGTGCAGCCCTCAC
AGAGCCTGTCCATCACCTGCACAGTCTCTGGTTTCTCATTAACTAGCTATGGT
GTACACTGGGTTCGCCAGTCTCCAGGAAAGGGTCTGGAGTGGCTGGGAGTG
ATATGGAGTGGTGGAAGCACAGACTATAATGCAGCTTTCATATCCAGACTGA
GCATCAGCAAGGACAATTCCAAGAGCCAAGTTTTCTTTAAAATGAACAGTCTG
CAAGCTAATGACACAGCCATATATTACTGTGCCAGAATGGAGAACTGGTCGT
TTGCTTACTGGGGCCAAGGGACCACGGTCACCGTCTCCTCCGGAGGTGGTG
GATCCGATATCAAACTGCAGCAGTCAGGGGCTGAACTGGCAAGACCTGGGG
CCTCAGTGAAGATGTCCTGCAAGACTTCTGGCTACACCTTTACTAGGTACAC
GATGCACTGGGTAAAACAGAGGCCTGGACAGGGTCTGGAATGGATTGGATA
CATTAATCCTAGCCGTGGTTATACTAATTACAATCAGAAGTTCAAGGACAAGG
CCACATTGACTACAGACAAATCCTCCAGCACAGCCTACATGCAACTGAGCAG
CCTGACATCTGAGGACTCTGCAGTCTATTACTGTGCAAGATATCATGATGATC
CATACTGCCTTGACTACTGGGGCCAAGGCACCACTCTCACAGTCTCCTCAGT
CGAAGGTGGAAGTGGAGGTTCTGGTGGAAGTGGAGGTTCAGGTGGAGTCGA
CGACATTCAGCTGACCCAGTCTCCAGCAATCATGTCTGCATCTCCAGGGGAG
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

Amino Acid Sequence of scFv Anti EpCAM×Anti CD3 with M31 Mutant in Anti CD3 Part:

AspIleGlnLeuThrGlnSerGlnLysPheMetSerThrSerValGlyAspArgValSerValThrCysLysAla    (SEQ ID NO. 79)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArg<u>TyrTyrGluGlyArgTyr</u>CysLeuAspTyrTrpGl
yGlnGlyThrThrLeuThrValSerSerValGluGlyGlySerGlyGlySerGlyGlySerGlyGlySerGlyGly
ValAspAspIleGlnLeuThrGlnSerProAlaIleMetSerAlaSerProGlyGluLysValThrMetThrCysA
rgAlaSerSerSerValSerTyrMetAsnTrpTyrGlnGlnLysSerGlyThrSerProLysArgTrpIleTyrAsp
ThrSerLysValAlaSerGlyValProTyrArgPheSerGlySerGlySerGlyThrSerTyrSerLeuThrIleSe
rSerMetGluAlaGluAspAlaAlaThrTyrTyrCysGlnGlnTrpSerSerAsnProLeuThrPheGlyAlaGl
yThrLysLeuGluLeuLysHisHisHisHisHisHis

Nucleotide Sequence Coding for scFv Anti EpCAM×Anti CD3 with M31 Mutant in Anti CD3 Part:

GATATCCAGCTGACCCAGTCTCAAAAATTCATGTCCACATCAGTAGGAGACA    (SEQ ID NO. 80)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
GTTCTCAGGTGAAACTGCAGGAGTCAGGACCTGGCCTAGTGCAGCCCTCAC
AGAGCCTGTCCATCACCTGCACAGTCTCTGGTTTCTCATTAACTAGCTATGGT
GTACACTGGGTTCGCCAGTCTCCAGGAAAGGGTCTGGAGTGGCTGGGAGTG
ATATGGAGTGGTGGAAGCACAGACTATAATGCAGCTTTCATATCCAGACTGA
GCATCAGCAAGGACAATTCCAAGAGCCAAGTTTTCTTTAAAATGAACAGTCTG
CAAGCTAATGACACAGCCATATATTACTGTGCCAGAATGGAGAACTGGTCGT
TTGCTTACTGGGGCCAAGGGACCACGGTCACCGTCTCCTCCGGAGGTGGTG
GATCCGATATCAAACTGCAGCAGTCAGGGGCTGAACTGGCAAGACCTGGGG

```
-continued
CCTCAGTGAAGATGTCCTGCAAGACTTCTGGCTACACCTTTACTAGGTACAC
GATGCACTGGGTAAAACAGAGGCCTGGACAGGGTCTGGAATGGATTGGATA
CATTAATCCTAGCCGTGGTTATACTAATTACAATCAGAAGTTCAAGGACAAGG
CCACATTGACTACAGACAAATCCTCCAGCACAGCCTACATGCAACTGAGCAG
CCTGACATCTGAGGACTCTGCAGTCTATTACTGTGCAAGATATTATGAAGGTC
GTTACTGCCTTGACTACTGGGGCCAAGGCACCACTCTCACAGTCTCCTCAGT
CGAAGGTGGAAGTGGAGGTTCTGGTGGAAGTGGAGGTTCAGGTGGAGTCGA
CGACATTCAGCTGACCCAGTCTCCAGCAATCATGTCTGCATCTCCAGGGGAG
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

25

Amino Acid Sequence of scFv Anti EpCAM×Anti CD3 with M58 Mutant in Anti CD3 Part:

AspIleGlnLeuThrGlnSerGlnLysPheMetSerThrSerValGlyAspArgValSerValThrCysLysAla (SEQ ID NO. 81)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArgTyrSerAspValTyrTyrCysLeuAspTyrTrpG
lyGlnGlyThrThrLeuThrValSerSerValGluGlyGlySerGlyGlySerGlyGlySerGlyGlySerGlyGly
ValAspAspIleGlnLeuThrGlnSerProAlaIleMetSerAlaSerProGlyGluLysValThrMetThrCysA
rgAlaSerSerSerValSerTyrMetAsnTrpTyrGlnGlnLysSerGlyThrSerProLysArgTrpIleTyrAsp
ThrSerLysValAlaSerGlyValProTyrArgPheSerGlySerGlySerGlyThrSerTyrSerLeuThrIleSe
rSerMetGluAlaGluAspAlaAlaThrTyrTyrCysGlnGlnTrpSerSerAsnProLeuThrPheGlyAlaGl
yThrLysLeuGluLeuLysHisHisHisHisHisHis

Nucleotide Sequence Coding for scFv Anti EpCAM×Anti CD3 with M58 Mutant in, Anti CD3 Part:

```
GATATCCAGCTGACCCAGTCTCAAAAATTCATGTCCACATCAGTAGGAGACA    (SEQ ID NO. 82)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
GTTCTCAGGTGAAACTGCAGGAGTCAGGACCTGGCCTAGTGCAGCCCTCAC
AGAGCCTGTCCATCACCTGCACAGTCTCTGGTTTCTCATTAACTAGCTATGGT
GTACACTGGGTTCGCCAGTCTCCAGGAAAGGGTCTGGAGTGGCTGGGAGTG
ATATGGAGTGGTGGAAGCACAGACTATAATGCAGCTTTCATATCCAGACTGA
GCATCAGCAAGGACAATTCCAAGAGCCAAGTTTTCTTTAAAATGAACAGTCTG
CAAGCTAATGACACAGCCATATATTACTGTGCCAGAATGGAGAACTGGTCGT
TTGCTTACTGGGGCCAAGGGACCACGGTCACCGTCTCCTCCGGAGGTGGTG
GATCCGATATCAAACTGCAGCAGTCAGGGGCTGAACTGGCAAGACCTGGGG
CCTCAGTGAAGATGTCCTGCAAGACTTCTGGCTACACCTTTACTAGGTACAC
GATGCACTGGGTAAAACAGAGGCCTGGACAGGGTCTGGAATGGATTGGATA
CATTAATCCTAGCCGTGGTTATACTAATTACAATCAGAAGTTCAAGGACAAGG
CCACATTGACTACAGACAAATCCTCCAGCACAGCCTACATGCAACTGAGCAG
CCTGACATCTGAGGACTCTGCAGTCTATTACTGTGCAAGATATTCTGATGTTT
ATTACTGCCTTGACTACTGGGGCCAAGGCACCACTCTCACAGTCTCCTCAGT
CGAAGGTGGAAGTGGAGGTTCTGGTGGAAGTGGAGGTTCAGGTGGAGTCGA
CGACATTCAGCTGACCCAGTCTCCAGCAATCATGTCTGCATCTCCAGGGGAG
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

Amino Acid Sequence of scFv Anti EpCAM×Anti CD3 with M65 Mutant in Anti CD3 Part:

```
AspIleGlnLeuThrGlnSerGlnLysPheMetSerThrSerValGlyAspArgValSerValThrCysLysAla    (SEQ ID NO. 83)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
```

-continued uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArg<u>TyrSerAspAspArgTyr</u>CysLeuAspTyrTrp
GlyGlnGlyThrThrLeuThrValSerSerValGluGlyGlySerGlyGlySerGlyGlySerGlyGlySerGlyGl
yValAspAspIleGlnLeuThrGlnSerProAlaIleMetSerAlaSerProGlyGluLysValThrMetThrCys
ArgAlaSerSerSerValSerTyrMetAsnTrpTyrGlnGlnLysSerGlyThrSerProLysArgTrpIleTyrA
spThrSerLysValAlaSerGlyValProTyrArgPheSerGlySerGlySerGlyThrSerTyrSerLeuThrIle
SerSerMetGluAlaGluAspAlaAlaThrTyrTyrCysGlnGlnTrpSerSerAsnProLeuThrPheGlyAla
GlyThrLysLeuGluLeuLysHisHisHisHisHisHis

25

Nucleotide Sequence Coding for scFv Anti EpCAM×Anti CD3 with M65 Mutant in Anti CD3 Part:

GATATCCAGCTGACCCAGTCTCAAAAATTCATGTCCACATCAGTAGGAGACA     (SEQ ID NO: 84)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
GTTCTCAGGTGAAACTGCAGGAGTCAGGACCTGGCCTAGTGCAGCCCTCAC
AGAGCCTGTCCATCACCTGCACAGTCTCTGGTTTCTCATTAACTAGCTATGGT
GTACACTGGGTTCGCCAGTCTCCAGGAAAGGGTCTGGAGTGGCTGGGAGTG
ATATGGAGTGGTGGAAGCACAGACTATAATGCAGCTTTCATATCCAGACTGA
GCATCAGCAAGGACAATTCCAAGAGCCAAGTTTTCTTTAAAATGAACAGTCTG
CAAGCTAATGACACAGCCATATATTACTGTGCCAGAATGGAGAACTGGTCGT
TTGCTTACTGGGGCCAAGGGACCACGGTCACCGTCTCCTCCGGAGGTGGTG
GATCCGATATCAAACTGCAGCAGTCAGGGGCTGAACTGGCAAGACCTGGGG
CCTCAGTGAAGATGTCCTGCAAGACTTCTGGCTACACCTTTACTAGGTACAC
GATGCACTGGGTAAAACAGAGGCCTGGACAGGGTCTGGAATGGATTGGATA
CATTAATCCTAGCCGTGGTTATACTAATTACAATCAGAAGTTCAAGGACAAGG
CCACATTGACTACAGACAAATCCTCCAGCACAGCCTACATGCAACTGAGCAG
CCTGACATCTGAGGACTCTGCAGTCTATTACTGTGCAAGA<u>TATTCTGATGATC
GTTAC</u>TGCCTTGACTACTGGGGCCAAGGCACCACTCTCACAGTCTCCTCAGT
CGAAGGTGGAAGTGGAGGTTCTGGTGGAAGTGGAGGTTCAGGTGGAGTCGA
CGACATTCAGCTGACCCAGTCTCCAGCAATCATGTCTGCATCTCCAGGGGAG

-continued

```
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

Amino Acid Sequence of scFv Anti EpCAM×Anti CD3 with
M69 Mutant in Anti CD3 Part:

AspIleGlnLeuThrGlnSerGlnLysPheMetSerThrSerValGlyAspArgValSerValThrCysLysAla (SEQ ID NO. 85)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArg<u>TyrAsnAspGluHisTyr</u>CysLeuAspTyrTrp
GlyGlnGlyThrThrLeuThrValSerSerValGluGlyGlySerGlyGlySerGlyGlySerGlyGlySerGlyGl
yValAspAspIleGlnLeuThrGlnSerProAlaIleMetSerAlaSerProGlyGluLysValThrMetThrCys
ArgAlaSerSerSerValSerTyrMetAsnTrpTyrGlnGlnLysSerGlyThrSerProLysArgTrpIleTyrA
spThrSerLysValAlaSerGlyValProTyrArgPheSerGlySerGlySerGlyThrSerTyrSerLeuThrIle
SerSerMetGluAlaGluAspAlaAlaThrTyrTyrCysGlnGlnTrpSerSerAsnProLeuThrPheGlyAla
GlyThrLysLeuGluLeuLysHisHisHisHisHisHis

Nucleotide Sequence Coding for scFv Anti EpCAM×Anti
CD3 with M69 Mutant in Anti CD3 Part:

```
GATATCCAGCTGACCCAGTCTCAAAAATTCATGTCCACATCAGTAGGAGACA    (SEQ ID NO: 86)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
```

-continued
```
GTTCTCAGGTGAAACTGCAGGAGTCAGGACCTGGCCTAGTGCAGCCCTCAC
AGAGCCTGTCCATCACCTGCACAGTCTCTGGTTTCTCATTAACTAGCTATGGT
GTACACTGGGTTCGCCAGTCTCCAGGAAAGGGTCTGGAGTGGCTGGGAGTG
ATATGGAGTGGTGGAAGCACAGACTATAATGCAGCTTTCATATCCAGACTGA
GCATCAGCAAGGACAATTCCAAGAGCCAAGTTTTCTTTAAAATGAACAGTCTG
CAAGCTAATGACACAGCCATATATTACTGTGCCAGAATGGAGAACTGGTCGT
TTGCTTACTGGGGCCAAGGGACCACGGTCACCGTCTCCTCCGGAGGTGGTG
GATCCGATATCAAACTGCAGCAGTCAGGGGCTGAACTGGCAAGACCTGGGG
CCTCAGTGAAGATGTCCTGCAAGACTTCTGGCTACACCTTTACTAGGTACAC
GATGCACTGGGTAAAACAGAGGCCTGGACAGGGTCTGGAATGGATTGGATA
CATTAATCCTAGCCGTGGTTATACTAATTACAATCAGAAGTTCAAGGACAAGG
CCACATTGACTACAGACAAATCCTCCAGCACAGCCTACATGCAACTGAGCAG
CCTGACATCTGAGGACTCTGCAGTCTATTACTGTGCAAGATATAATGATGAAC
ATTACTGCCTTGACTACTGGGGCCAAGGCACCACTCTCACAGTCTCCTCAGT
CGAAGGTGGAAGTGGAGGTTCTGGTGGAAGTGGAGGTTCAGGTGGAGTCGA
CGACATTCAGCTGACCCAGTCTCCAGCAATCATGTCTGCATCTCCAGGGGAG
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

Amino Acid Sequence of scFv Anti EpCAM×Anti CD3 with M76 Mutant in Anti CD3 Part:

```
AspIleGlnLeuThrGlnSerGlnLysPheMetSerThrSerValGlyAspArgValSerValThrCysLysAla      (SEQ ID NO: 87)
SerGlnAsnValGlyThrAsnValAlaTrpTyrGlnGlnLysProGlyGlnSerProLysAlaLeuIleTyrSerAl
aSerTyrArgTyrSerGlyValProAspArgPheThrGlySerGlySerGlyThrAspPheThrLeuThrIleSe
rAsnValGlnSerGluAspLeuAlaGluTyrPheCysGlnGlnTyrAsnSerTyrProLeuThrPheGlyAla
GlyThrLysLeuGluIleLysGlyGlyGlyGlySerGlyGlyGlyGlySerGlyGlyGlyGlySerGlnValLysLe
uGlnGluSerGlyProGlyLeuValGlnProSerGlnSerLeuSerIleThrCysThrValSerGlyPheSerLe
uThrSerTyrGlyValHisTrpValArgGlnSerProGlyLysGlyLeuGluTrpLeuGlyValIleTrpSerGlyG
lySerThrAspTyrAsnAlaAlaPheIleSerArgLeuSerIleSerLysAspAsnSerLysSerGlnValPheP
heLysMetAsnSerLeuGlnAlaAsnAspThrAlaIleTyrTyrCysAlaArgMetGluAsnTrpSerPheAla
TyrTrpGlyGlnGlyThrThrValThrValSerSerGlyGlyGlyGlySerAspIleLysLeuGlnGlnSerGlyAl
aGluLeuAlaArgProGlyAlaSerValLysMetSerCysLysThrSerGlyTyrThrPheThrArgTyrThrMe
tHisTrpValLysGlnArgProGlyGlnGlyLeuGluTrpIleGlyTyrIleAsnProSerArgGlyTyrThrAsnTy
rAsnGlnLysPheLysAspLysAlaThrLeuThrThrAspLysSerSerSerThrAlaTyrMetGlnLeuSerS
erLeuThrSerGluAspSerAlaValTyrTyrCysAlaArgTyrTyrAspAspAsnTyrCysLeuAspTyrTrp
GlyGlnGlyThrThrLeuThrValSerSerValGluGlyGlySerGlyGlySerGlyGlySerGlyGlySerGlyGl
``` yValAspAspIleGlnLeuThrGlnSerProAlaIleMetSerAlaSerProGlyGluLysValThrMetThrCys

ArgAlaSerSerSerValSerTyrMetAsnTrpTyrGlnGlnLysSerGlyThrSerProLysArgTrpIleTyrA spThrSerLysValAlaSerGlyValProTyrArgPheSerGlySerGlySerGlyThrSerTyrSerLeuThrIle

SerSerMetGluAlaGluAspAlaAlaThrTyrTyrCysGlnGlnTrpSerSerAsnProLeuThrPheGlyAla

GlyThrLysLeuGluLeuLysHisHisHisHisHisHis

Nucleotide Sequence Coding for scFv Anti EpCAM×Anti CD3 with M76 Mutant in Anti CD3 Part:

```
GATATCCAGCTGACCCAGTCTCAAAAATTCATGTCCACATCAGTAGGAGACA    (SEQ ID NO: 88)
GGGTCAGCGTCACCTGCAAGGCCAGTCAGAATGTGGGTACTAATGTAGCCT
GGTATCAACAGAAACCAGGGCAATCTCCTAAAGCACTGATTTACTCGGCATC
CTACCGGTACAGTGGAGTCCCTGATCGCTTCACAGGCAGTGGATCTGGGAC
AGATTTCACTCTCACCATCAGCAATGTGCAGTCTGAAGACTTGGCAGAGTATT
TCTGTCAGCAATATAACAGCTATCCGCTCACGTTCGGTGCTGGGACCAAGCT
CGAGATCAAAGGTGGTGGTGGTTCTGGCGGCGGCGGCTCCGGTGGTGGTG
GTTCTCAGGTGAAACTGCAGGAGTCAGGACCTGGCCTAGTGCAGCCCTCAC
AGAGCCTGTCCATCACCTGCACAGTCTCTGGTTTCTCATTAACTAGCTATGGT
GTACACTGGGTTCGCCAGTCTCCAGGAAAGGGTCTGGAGTGGCTGGGAGTG
ATATGGAGTGGTGGAAGCACAGACTATAATGCAGCTTTCATATCCAGACTGA
GCATCAGCAAGGACAATTCCAAGAGCCAAGTTTTCTTTAAAATGAACAGTCTG
CAAGCTAATGACACAGCCCATATATTACTGTGCCAGAATGGAGAACTGGTCGT
TTGCTTACTGGGGCCAAGGGACCACGGTCACCGTCTCCTCCGGAGGTGGTG
GATCCGATATCAAACTGCAGCAGTCAGGGGCTGAACTGGCAAGACCTGGGG
CCTCAGTGAAGATGTCCTGCAAGACTTCTGGCTACACCTTTACTAGGTACAC
GATGCACTGGGTAAAACAGAGGCCTGGACAGGGTCTGGAATGGATTGGATA
CATTAATCCTAGCCGTGGTTATACTAATTACAATCAGAAGTTCAAGGACAAGG
CCACATTGACTACAGACAAATCCTCCAGCACAGCCTACATGCAACTGAGCAG
CCTGACATCTGAGGACTCTGCAGTCTATTACTGTGCAAGATATTATGATGATA
ATTACTGCCTTGACTACTGGGGCCAAGGCACCACTCTCACAGTCTCCTCAGT
CGAAGGTGGAAGTGGAGGTTCTGGTGGAAGTGGAGGTTCAGGTGGAGTCGA
CGACATTCAGCTGACCCAGTCTCCAGCAATCATGTCTGCATCTCCAGGGGAG
AAGGTCACCATGACCTGCAGAGCCAGTTCAAGTGTAAGTTACATGAACTGGT
ACCAGCAGAAGTCAGGCACCTCCCCCAAAAGATGGATTTATGACACATCCAA
AGTGGCTTCTGGAGTCCCTTATCGCTTCAGTGGCAGTGGGTCTGGGACCTC
ATACTCTCTCACAATCAGCAGCATGGAGGCTGAAGATGCTGCCACTTATTAC
TGCCAACAGTGGAGTAGTAACCCGCTCACGTTCGGTGCTGGGACCAAGCTG
GAGCTGAAACATCATCACCATCATCATTAG
```

The invention claimed is:

1. A polypeptide construct comprising the CDR-1, CDR-2, CDR-3 regions of $V_L$, as well as the CDR-1, CDR-2, CDR-3 regions of $V_H$, wherein the CDR-3 of $V_H$ is selected from the group consisting of:
Y Y N D Q Y (M13, SEQ ID NO: 8),
Y S D V Y Y (M58, SEQ ID NO: 12),
and Y N D E H Y (M69, SEQ ID NO: 14),
and wherein said polypeptide construct has a low binding affinity for CD3 and is highly efficacious in activating a T-cell; and
wherein the $V_L$ polypeptide chain comprises the CDR-1, CDR-2 and CDR-3 regions of the murine OKT3 anti-CD3 antibody $V_L$ polypeptide chain and the $V_H$ polypeptide chain comprises the CDR-1 and CDR-2 regions of the murine OKT3 anti-CD3 antibody $V_H$ polypeptide chain.

2. The polypeptide construct of claim 1, wherein said polypeptide construct is
(a) capable of specifically binding to/interacting with the CD3 of a T-cell and/or
(b) of activating a T-cell.

3. The polypeptide construct of claim 2, wherein said activation of a T-cell comprises the upregulation of expression of cell surface proteins CD69, and/or CD25, the upregulation of expression of interferon gamma, and/or an increased cytotoxicity as compared to a non-activated T-cell.

4. The polypeptide construct of claim 1, wherein said at least one CDR-3 region comprises a substitution in the amino acid sequence YYDDHY (SEQ ID NO:1) which is located in the CDR-3 region of a heavy chain variable region ($V_H$).

5. The polypeptide construct of claim 4, wherein said heavy chain variable region is a $V_H$-region of an antibody capable of binding to and/or interacting with CD3.

6. The polypeptide construct of claim 5, wherein said antibody is derived from OKT-3.

7. The polypeptide construct of claim 5, wherein said heavy chain variable region ($V_H$) is selected from the group consisting of
(a) a $V_H$-region comprising an amino acid sequence derived from the sequence as shown in SEQ ID NO: 40, 42 or 57;
(b) a $V_H$-region encoded by a nucleic acid molecule derived from the sequence as shown in SEQ ID NO: 41, 43 or 58;
(c) a $V_H$-region which is encoded by a polynucleotide which is at least 90% identical to the nucleic acid molecule as defined in (b) and which comprises a YYDDHY-motif selected from the group consisting of
Y Y N D Q Y (M13, SEQ ID NO: 8),
Y S D V Y Y (M58, SEQ ID NO: 12), and
Y N D E H Y (M69, SEQ ID NO: 14), and
(d) a $V_H$-region which is encoded by a polynucleotide which hybridizes under stringent conditions at 60° C. in 2×SSC and 0.1% SDS to the complementary strand of a polynucleotide/nucleic acid molecule defined in (b) or (c) and which comprises a YYDDHY-motif selected from the group consisting of
Y Y N D Q Y (M13, SEQ ID NO: 8),
Y S D V Y Y (M58, SEQ ID NO: 12), and
Y N D E H Y (M69, SEQ ID NO: 14).

8. The polypeptide construct of claim 1, wherein said polypeptide construct is capable of binding to and/or interacting with CD3.

9. The polypeptide construct of claim 1, wherein said polypeptide construct is highly efficacious in activating a T-cell.

10. The polypeptide construct of claim 9, wherein said polypeptide construct comprises a CDR-3 region which comprises a sequence motif selected from the group consisting of YYNDQY (M13, SEQ ID NO. 8), YSDVYY (M58, SEQ ID NO. 12) and YNDEHY (M69, SEQ ID NO. 14).

11. The polypeptide construct of claim 1, wherein said polypeptide construct is in the format of an Fab, an F(ab')$_2$, a single chain Fv (scFv), a bispecific scFV, an antibody fusion protein, an antibody-antigen-construct or a heterominibody.

12. The polypeptide construct of claim 1, wherein said polypeptide construct is capable of specifically binding to/interacting with the CD3 of a T-cell and is capable of binding to/interacting with a second target molecule.

13. The polypeptide construct of claim 12, which is a polypeptide construct capable of specifically binding to/interacting with the CD3 of a T-cell and with EpCAM.

14. The polypeptide construct of claim 13 which is a bispecific single chain construct.

15. The polypeptide construct of claim 4, wherein said heavy chain variable region ($V_H$) is derived from the $V_H$-region of OKT-3.

16. A polynucleotide encoding a polypeptide construct of claim 1.

17. The polynucleotide of claim 16 which is DNA or RNA.

18. A vector comprising the polynucleotide of claim 16.

19. A host cell comprising the polynucleotide of claim 16 or a vector comprising said polynucleotide.

20. A method for the preparation of a polypeptide construct of claim 1 which method comprises cultivating a host cell comprising a polynucleotide encoding said polypeptide construct and isolating said polypeptide construct from said culture.

21. A composition comprising a polypeptide construct of claim 1.

22. The composition of claim 21, which is a pharmaceutical composition comprising suitable formulations of carrier, stabilizers, diluents and/or excipients.

23. A kit comprising a composition comprising a polypeptide construct of claim 1.

24. The polypeptide of claim 1, wherein the VH polypeptide chain is selected from the group consisting of SEQ ID NOs: 40, SEQ ID NOs: 42, and SEQ ID NOs: 57, wherein the YYDDHY (SEQ ID NO: 1) sequence found in SEQ ID NOs: 40, SEQ ID NOs: 42, or SEQ ID NOs: 57 is modified by substitution with a sequence from the group consisting of SEQ ID NO: 8, SEQ ID NO: 12, and SEQ ID NO: 14.

25. The polypeptide construct of claim 14, wherein said bispecific single chain construct is encoded by a nucleic acid molecule comprising SEQ ID NO: 74.

26. The polypeptide construct of claim 14, wherein said bispecific single chain construct is encoded by a nucleic acid molecule comprising SEQ ID NO: 82.

27. The polypeptide construct of claim 14, wherein said bispecific single chain construct is encoded by a nucleic acid molecule comprising SEQ ID NO: 86.

28. The polypeptide construct of claim 14, wherein said bispecific single chain construct comprises SEQ ID NO: 73.

29. The polypeptide construct of claim 14, wherein said bispecific single chain construct comprises SEQ ID NO: 81.

30. The polypeptide construct of claim 14, wherein said bispecific single chain construct comprises SEQ ID NO: 85.

* * * * *

SEQUENCE LISTING

<160> NUMBER OF SEQ ID NOS: 89

<210> SEQ ID NO 1
<211> LENGTH: 6
<212> TYPE: PRT
<213> ORGANISM: artificial sequence
<220> FEATURE:
<223> OTHER INFORMATION: WT CD3 CDRH3

<400> SEQUENCE: 1

Tyr Tyr Asp Asp His Tyr
1               5

<210> SEQ ID NO 2
<211> LENGTH: 6
<212> TYPE: PRT
<213> ORGANISM: artificial sequence
<220> FEATURE:
<223> OTHER INFORMATION: M1 Mutant

<400> SEQUENCE: 2

His Tyr Asp Asp His Tyr
1               5

<210> SEQ ID NO 3
<211> LENGTH: 6
<212> TYPE: PRT
<213> ORGANISM: artificial sequence
<220> FEATURE:
<223> OTHER INFORMATION: M4 Mutant

<400> SEQUENCE: 3

Tyr Ser Asp Asp His Tyr
1               5

<210> SEQ ID NO 4
<211> LENGTH: 6
<212> TYPE: PRT
<213> ORGANISM: artificial sequence
<220> FEATURE:
<223> OTHER INFORMATION: M7 mutant

<400> SEQUENCE: 4

Tyr Tyr Asp Ala His Tyr
1               5

<210> SEQ ID NO 5
<211> LENGTH: 6
<212> TYPE: PRT
<213> ORGANISM: artificial sequence
<220> FEATURE:
<223> OTHER INFORMATION: M9 mutant

<400> SEQUENCE: 5

Tyr Tyr Asp Asp Gln Tyr
1               5

<210> SEQ ID NO 6
<211> LENGTH: 6
<212> TYPE: PRT
<213> ORGANISM: artificial sequence
<220> FEATURE:
<223> OTHER INFORMATION: M19 mutant

<400> SEQUENCE: 6

```
Tyr Tyr Asp Asp Pro Tyr
1               5

<210> SEQ ID NO 7
<211> LENGTH: 6
<212> TYPE: PRT
<213> ORGANISM: artificial sequence
<220> FEATURE:
<223> OTHER INFORMATION: M11 mutant

<400> SEQUENCE: 7

Tyr Phe Asn Asp His Tyr
1               5

<210> SEQ ID NO 8
<211> LENGTH: 6
<212> TYPE: PRT
<213> ORGANISM: artificial sequence
<220> FEATURE:
<223> OTHER INFORMATION: M13 mutant

<400> SEQUENCE: 8

Tyr Tyr Asn Asp Gln Tyr
1               5

<210> SEQ ID NO 9
<211> LENGTH: 6
<212> TYPE: PRT
<213> ORGANISM: artificial sequence
<220> FEATURE:
<223> OTHER INFORMATION: M14 mutant

<400> SEQUENCE: 9

Tyr Tyr Asp Ala His Asn
1               5

<210> SEQ ID NO 10
<211> LENGTH: 6
<212> TYPE: PRT
<213> ORGANISM: artificial sequence
<220> FEATURE:
<223> OTHER INFORMATION: M20 mutant

<400> SEQUENCE: 10

Tyr His Asp Asp Pro Tyr
1               5

<210> SEQ ID NO 11
<211> LENGTH: 6
<212> TYPE: PRT
<213> ORGANISM: artificial sequence
<220> FEATURE:
<223> OTHER INFORMATION: M31 mutant

<400> SEQUENCE: 11

Tyr Tyr Glu Gly Arg Tyr
1               5

<210> SEQ ID NO 12
<211> LENGTH: 6
<212> TYPE: PRT
<213> ORGANISM: artificial sequence
<220> FEATURE:
<223> OTHER INFORMATION: M58 mutant

<400> SEQUENCE: 12

Tyr Ser Asp Val Tyr Tyr
```

```
<210> SEQ ID NO 13
<211> LENGTH: 6
<212> TYPE: PRT
<213> ORGANISM: artificial sequence
<220> FEATURE:
<223> OTHER INFORMATION: M65 mutant

<400> SEQUENCE: 13

Tyr Ser Asp Asp Arg Tyr
1               5

<210> SEQ ID NO 14
<211> LENGTH: 6
<212> TYPE: PRT
<213> ORGANISM: artificial sequence
<220> FEATURE:
<223> OTHER INFORMATION: M69 mutant

<400> SEQUENCE: 14

Tyr Asn Asp Glu His Tyr
1               5

<210> SEQ ID NO 15
<211> LENGTH: 6
<212> TYPE: PRT
<213> ORGANISM: artificial sequence
<220> FEATURE:
<223> OTHER INFORMATION: M76 mutant

<400> SEQUENCE: 15

Tyr Tyr Asp Asp Asn Tyr
1               5

<210> SEQ ID NO 16
<211> LENGTH: 6
<212> TYPE: PRT
<213> ORGANISM: artificial sequence
<220> FEATURE:
<223> OTHER INFORMATION: M2 mutant

<400> SEQUENCE: 16

Asp Tyr Asp Asp His Tyr
1               5

<210> SEQ ID NO 17
<211> LENGTH: 6
<212> TYPE: PRT
<213> ORGANISM: artificial sequence
<220> FEATURE:
<223> OTHER INFORMATION: M3 mutant

<400> SEQUENCE: 17

Phe Tyr Asp Asp His Tyr
1               5

<210> SEQ ID NO 18
<211> LENGTH: 6
<212> TYPE: PRT
<213> ORGANISM: artificial sequence
<220> FEATURE:
<223> OTHER INFORMATION: M5 mutant

<400> SEQUENCE: 18

Tyr Tyr Val Asp His Tyr
1               5
```

```
<210> SEQ ID NO 19
<211> LENGTH: 6
<212> TYPE: PRT
<213> ORGANISM: artificial sequence
<220> FEATURE:
<223> OTHER INFORMATION: M6 mutant

<400> SEQUENCE: 19

Tyr Tyr Ala Asp His Tyr
1               5

<210> SEQ ID NO 20
<211> LENGTH: 6
<212> TYPE: PRT
<213> ORGANISM: artificial sequence
<220> FEATURE:
<223> OTHER INFORMATION: M12 mutant

<400> SEQUENCE: 20

Tyr Tyr His His His Tyr
1               5

<210> SEQ ID NO 21
<211> LENGTH: 6
<212> TYPE: PRT
<213> ORGANISM: artificial sequence
<220> FEATURE:
<223> OTHER INFORMATION: M16 mutant

<400> SEQUENCE: 21

Tyr Asp Asp Glu His Cys
1               5

<210> SEQ ID NO 22
<211> LENGTH: 6
<212> TYPE: PRT
<213> ORGANISM: artificial sequence
<220> FEATURE:
<223> OTHER INFORMATION: M21 mutant

<400> SEQUENCE: 22

Tyr Tyr Asp Asp His His
1               5

<210> SEQ ID NO 23
<211> LENGTH: 6
<212> TYPE: PRT
<213> ORGANISM: artificial sequence
<220> FEATURE:
<223> OTHER INFORMATION: M24 mutant

<400> SEQUENCE: 23

Asp Leu Gly Asp His Tyr
1               5

<210> SEQ ID NO 24
<211> LENGTH: 6
<212> TYPE: PRT
<213> ORGANISM: artificial sequence
<220> FEATURE:
<223> OTHER INFORMATION: M64 mutant

<400> SEQUENCE: 24

Tyr Tyr Gly Asp Pro Tyr
1               5
```

-continued

```
<210> SEQ ID NO 25
<211> LENGTH: 6
<212> TYPE: PRT
<213> ORGANISM: artificial sequence
<220> FEATURE:
<223> OTHER INFORMATION: M82 mutant

<400> SEQUENCE: 25

Asn Tyr Asp Asp His Tyr
1               5

<210> SEQ ID NO 26
<211> LENGTH: 6
<212> TYPE: PRT
<213> ORGANISM: artificial sequence
<220> FEATURE:
<223> OTHER INFORMATION: M0 Mutant

<400> SEQUENCE: 26

Val Val Ser Ser Gln Val
1               5

<210> SEQ ID NO 27
<211> LENGTH: 18
<212> TYPE: DNA
<213> ORGANISM: artificial sequence
<220> FEATURE:
<223> OTHER INFORMATION: WT CD3 CDRH

<400> SEQUENCE: 27
tattatgatg atcattac                                                 18

<210> SEQ ID NO 28
<211> LENGTH: 18
<212> TYPE: DNA
<213> ORGANISM: artificial sequence
<220> FEATURE:
<223> OTHER INFORMATION: M13

<400> SEQUENCE: 28
tattataatg atcaatac                                                 18

<210> SEQ ID NO 29
<211> LENGTH: 18
<212> TYPE: DNA
<213> ORGANISM: artificial sequence
<220> FEATURE:
<223> OTHER INFORMATION: M58

<400> SEQUENCE: 29
tattctgatg tttactac                                                 18

<210> SEQ ID NO 30
<211> LENGTH: 18
<212> TYPE: DNA
<213> ORGANISM: artificial sequence
<220> FEATURE:
<223> OTHER INFORMATION: M69

<400> SEQUENCE: 30
tattatgatg atcattac                                                 18

<210> SEQ ID NO 31
<211> LENGTH: 18
<212> TYPE: DNA
<213> ORGANISM: artificial sequence
```

-continued

```
<220> FEATURE:
<223> OTHER INFORMATION: M0 mutant

<400> SEQUENCE: 31
gttgtctcct cccaagtt                                                     18

<210> SEQ ID NO 32
<211> LENGTH: 18
<212> TYPE: DNA
<213> ORGANISM: artificial sequence
<220> FEATURE:
<223> OTHER INFORMATION: M12 mutant

<400> SEQUENCE: 32
tattatcatc atcattac                                                     18

<210> SEQ ID NO 33
<211> LENGTH: 18
<212> TYPE: DNA
<213> ORGANISM: artificial sequence
<220> FEATURE:
<223> OTHER INFORMATION: M16 mutant

<400> SEQUENCE: 33
tatgatgatg aacattgc                                                     18

<210> SEQ ID NO 34
<211> LENGTH: 18
<212> TYPE: DNA
<213> ORGANISM: artificial sequence
<220> FEATURE:
<223> OTHER INFORMATION: M65 mutant

<400> SEQUENCE: 34
tattccgatg atagatat                                                     18

<210> SEQ ID NO 35
<211> LENGTH: 18
<212> TYPE: DNA
<213> ORGANISM: artificial sequence
<220> FEATURE:
<223> OTHER INFORMATION: M76 mutant

<400> SEQUENCE: 35
tattatgatg ataactat                                                     18

<210> SEQ ID NO 36
<211> LENGTH: 10
<212> TYPE: PRT
<213> ORGANISM: artificial sequence
<220> FEATURE:
<223> OTHER INFORMATION: WT CDR3H of OKT3

<400> SEQUENCE: 36

Tyr Tyr Asp Asp His Tyr Cys Leu Asp Tyr
1               5                   10

<210> SEQ ID NO 37
<211> LENGTH: 30
<212> TYPE: DNA
<213> ORGANISM: artificial sequence
<220> FEATURE:
<223> OTHER INFORMATION: WT CDR3H of OKT3

<400> SEQUENCE: 37
tattatgatg atcattactg ccttgactac                                        30
```

<210> SEQ ID NO 38
<211> LENGTH: 468
<212> TYPE: PRT
<213> ORGANISM: artificial sequence
<220> FEATURE:
<223> OTHER INFORMATION: OKT3 heavy chain with signal peptide

<400> SEQUENCE: 38

```
Met Glu Arg His Trp Ile Phe Leu Leu Leu Ser Val Thr Ala Gly
 1               5                  10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Ala Lys Thr Thr Ala Pro
    130                 135                 140

Ser Val Tyr Pro Leu Ala Pro Val Cys Gly Asp Thr Thr Gly Ser Ser
145                 150                 155                 160

Val Thr Leu Gly Cys Leu Val Lys Gly Tyr Phe Pro Glu Pro Val Thr
                165                 170                 175

Leu Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Thr Ser Ser Thr Trp Pro Ser Gln Ser Ile Thr Cys Asn Val Ala His
    210                 215                 220

Pro Ala Ser Ser Thr Lys Val Asp Lys Lys Ile Glu Pro Arg Gly Pro
225                 230                 235                 240

Thr Ile Lys Pro Cys Pro Pro Cys Lys Cys Pro Ala Pro Asn Leu Leu
                245                 250                 255

Gly Gly Pro Ser Val Phe Ile Phe Pro Pro Lys Ile Lys Asp Val Leu
            260                 265                 270

Met Ile Ser Leu Ser Pro Ile Val Thr Cys Val Val Val Asp Val Ser
        275                 280                 285

Glu Asp Asp Pro Asp Val Gln Ile Ser Trp Phe Val Asn Asn Val Glu
    290                 295                 300

Val His Thr Ala Gln Thr Gln Thr His Arg Glu Asp Tyr Asn Ser Thr
305                 310                 315                 320

Leu Arg Val Val Ser Ala Leu Pro Ile Gln His Gln Asp Trp Met Ser
                325                 330                 335

Gly Lys Glu Phe Lys Cys Lys Val Asn Asn Lys Asp Leu Pro Ala Pro
            340                 345                 350

Ile Glu Arg Thr Ile Ser Lys Pro Lys Gly Ser Val Arg Ala Pro Gln
        355                 360                 365
```

```
Val Tyr Val Leu Pro Pro Glu Glu Glu Met Thr Lys Lys Gln Val
        370                 375                 380

Thr Leu Thr Cys Met Val Thr Asp Phe Met Pro Glu Asp Ile Tyr Val
385                 390                 395                 400

Glu Trp Thr Asn Asn Gly Lys Thr Glu Leu Asn Tyr Lys Asn Thr Glu
                405                 410                 415

Pro Val Leu Asp Ser Asp Gly Ser Tyr Phe Met Tyr Ser Lys Leu Arg
            420                 425                 430

Val Glu Lys Lys Asn Trp Val Glu Arg Asn Ser Tyr Ser Cys Ser Val
        435                 440                 445

Val His Glu Gly Leu His Asn His His Thr Thr Lys Ser Phe Ser Arg
    450                 455                 460

Thr Pro Gly Lys
465
```

<210> SEQ ID NO 39
<211> LENGTH: 1570
<212> TYPE: DNA
<213> ORGANISM: artificial sequence
<220> FEATURE:
<223> OTHER INFORMATION: OKT3 heavy chain with signal peptide

<400> SEQUENCE: 39

```
gaattcccct ctccacagac actgaaaact ctgactcaac atggaaaggc actggatctt    60
tctactcctg ttgtcagtaa ctgcaggtgt ccactcccag gtccagctgc agcagtctgg   120
ggctgaactg gcaagacctg ggcctcagt gaagatgtcc tgcaaggctt ctggctacac    180
ctttactagg tacacgatgc actgggtaaa acagaggcct ggacagggtc tggaatggat    240
tggatacatt aatcctagcc gtggttatac taattacaat cagaagttca aggacaaggc    300
cacattgact acagacaaat cctccagcac agcctacatg caactgagca gcctgacatc    360
tgaggactct gcagtctatt actgtgcaag atattatgat gatcattact gccttgacta    420
ctggggccaa ggcaccactc tcacagtctc ctcagccaaa acaacagccc catcggtcta    480
tccactggcc cctgtgtgtg agatacaac tggctcctcg gtgactctag gatgcctggt     540
caagggttat ttccctgagc cagtgacctt gacctggaac tctggatccc tgtccagtgg    600
tgtgcacacc ttcccagctg tcctgcagtc tgacctctac accctcagca gctcagtgac    660
tgtaacctcg agcacctggc ccagccagtc catcacctgc aatgtggccc acccggcaag    720
cagcaccaag gtggacaaga aaattgagcc cagagggccc acaatcaagc cctgtcctcc    780
atgcaaatgc ccagcaccta acctcttggg tggaccatcc gtcttcatct tccctccaaa    840
gatcaaggat gtactcatga tctccctgag ccccatagtc acatgtgtgg tggtggatgt    900
gagcgaggat gacccagatg tccagatcag ctggtttgtg aacaacgtgg aagtacacac    960
agctcagaca caaacccata gagaggatta acagtact ctccgggtgg tcagtgccct     1020
ccccatccag caccaggact ggatgagtgg caaggagttc aaatgcaagg tcaacaacaa   1080
agacctccca gcgcccatcg agagaaccat ctcaaaaccc aaagggtcag taagagctcc   1140
acaggtatat gtcttgcctc caccagaaga agagatgact aagaaacagg tcactctgac   1200
ctgcatggtc acagacttca tgcctgaaga catttacgtg gagtggacca acaacgggaa   1260
aacagagcta aactacaaga cactgaacc agtcctggac tctgatggtt cttacttcat   1320
gtacagcaag ctgagagtgg aaaagaagaa ctgggtggaa agaaatagct actcctgttc   1380
agtggtccac gagggtctgc acaatcacca cacgactaag agcttctccc ggactccggg   1440
```

-continued

```
taaatgagct cagcacccac aaaactctca ggtccaaaga gacacccaca ctcatctcca     1500
tgcttcccTt gtataaataa agcacccagc aatgcctggg accatgtaaa aaaaaaaaa     1560 aaaggaattc                                                            1570
```

<210> SEQ ID NO 40
<211> LENGTH: 138
<212> TYPE: PRT
<213> ORGANISM: artificial sequence
<220> FEATURE:
<223> OTHER INFORMATION: OKT3 heavy chain variable region with signal
      peptide

<400> SEQUENCE: 40

```
Met Asp Trp Val Trp Thr Leu Leu Phe Leu Leu Ser Val Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser
    130                 135
```

<210> SEQ ID NO 41
<211> LENGTH: 417
<212> TYPE: DNA
<213> ORGANISM: artificial sequence
<220> FEATURE:
<223> OTHER INFORMATION: OKT3 heavy chain variable region with signal
      peptide

<400> SEQUENCE: 41

```
tccatggatt gggtgtggac cttgctattc ctgttgtcag taactgcagg tgtccactcc     60
caggtccagc tgcagcagtc tggggctgaa ctggcaagac ctggggcctc agtgaagatg    120
tcctgcaagg cttctggcta cacctttact aggtacacga tgcactgggt aaaacagagg    180
cctggacagg gtctggaatg gattggatac attaatccta gccgtggtta tactaattac    240
aatcagaagt tcaaggacaa ggccacattg actacagaca atcctccag cacagcctac     300 atgcaactga gcagcctgac atctgaggac tctgcagtct attactgtgc aagatattat    360
gatgatcatt actgccttga ctactggggc caaggcacca ctctcacagt ctcctca      417
```

<210> SEQ ID NO 42
<211> LENGTH: 119
<212> TYPE: PRT
<213> ORGANISM: artificial sequence
<220> FEATURE:
<223> OTHER INFORMATION: Variable region of OKT3 without signal peptide

<400> SEQUENCE: 42

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115
```

<210> SEQ ID NO 43
<211> LENGTH: 357
<212> TYPE: DNA
<213> ORGANISM: artificial sequence
<220> FEATURE:
<223> OTHER INFORMATION: Variable region of OKT3 without signal peptide

<400> SEQUENCE: 43

```
caggtccagc tgcagcagtc tggggctgaa ctggcaagac ctggggcctc agtgaagatg    60
tcctgcaagg cttctggcta cacctttact aggtacacga tgcactgggt aaaacagagg   120
cctggacagg gtctgaatg gattggatac attaatccta gccgtggtta tactaattac   180
aatcagaagt tcaaggacaa ggccacattg actacagaca atcctccag cacagcctac    240 atgcaactga gcagcctgac atctgaggac tctgcagtct attactgtgc aagatattat    300
gatgatcatt actgccttga ctactggggc caaggcacca ctctcacagt ctcctca      357
```

<210> SEQ ID NO 44
<211> LENGTH: 26
<212> TYPE: DNA
<213> ORGANISM: artificial sequence
<220> FEATURE:
<223> OTHER INFORMATION: 5' light Eco5

<400> SEQUENCE: 44

```
aagatatcca gctgacccag tctcca                                          26
```

<210> SEQ ID NO 45
<211> LENGTH: 22
<212> TYPE: DNA
<213> ORGANISM: artificial sequence
<220> FEATURE:
<223> OTHER INFORMATION: 3'light Bgl2

<400> SEQUENCE: 45

```
gttagatctc gagcttggtc cc                                              22
```

<210> SEQ ID NO 46
<211> LENGTH: 30
<212> TYPE: DNA
<213> ORGANISM: artificial sequence
<220> FEATURE:
<223> OTHER INFORMATION: 5' heavy Eco5

<400> SEQUENCE: 46
aagatatcag gtsmarctgc agsagtcwgg         30

<210> SEQ ID NO 47
<211> LENGTH: 39
<212> TYPE: DNA
<213> ORGANISM: artificial sequence
<220> FEATURE:
<223> OTHER INFORMATION: 3' heavy BspE1

<400> SEQUENCE: 47
aatccggagg agacggtgac cgtggtccct tggccccag         39

<210> SEQ ID NO 48
<211> LENGTH: 51
<212> TYPE: DNA
<213> ORGANISM: artificial sequence
<220> FEATURE:
<223> OTHER INFORMATION: 3' light linker

<400> SEQUENCE: 48
ggagccgccg ccgccagaac caccaccacc tttgatctcg agcttggtcc c         51

<210> SEQ ID NO 49
<211> LENGTH: 50
<212> TYPE: DNA
<213> ORGANISM: artificial sequence
<220> FEATURE:
<223> OTHER INFORMATION: 5' heavy linker

<400> SEQUENCE: 49
ggcggcggcg gctccggtgg tggtggttct caggtgaaac tgcaggagtc         50

<210> SEQ ID NO 50
<211> LENGTH: 44
<212> TYPE: DNA
<213> ORGANISM: artificial sequence
<220> FEATURE:
<223> OTHER INFORMATION: 5' heavy CD3 linker 5

<400> SEQUENCE: 50
taatccggag gtggtggatc cgatatcaaa ctgcagcagt cagg         44

<210> SEQ ID NO 51
<211> LENGTH: 74
<212> TYPE: DNA
<213> ORGANISM: artificial sequence
<220> FEATURE:
<223> OTHER INFORMATION: 5' heavy CD3 linker 15

<400> SEQUENCE: 51
taatccggag gtggtggttc cggggtggt ggttccgggg gtggtggatc cgatatcaaa         60
ctgcagcagt cagg         74

<210> SEQ ID NO 52
<211> LENGTH: 59
<212> TYPE: DNA
<213> ORGANISM: artificial sequence
<220> FEATURE:
<223> OTHER INFORMATION: 3' light CD3 His

<400> SEQUENCE: 52
tttaagcttg tcgactaatg atgatggtga tgatgtttca gctccagctt ggtcccagc         59

<210> SEQ ID NO 53
<211> LENGTH: 116
<212> TYPE: PRT
<213> ORGANISM: artificial sequence
<220> FEATURE:
<223> OTHER INFORMATION: anti-EpCAM VH

<400> SEQUENCE: 53

```
Gln Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Met Glu Asn Trp Ser Phe Ala Tyr Trp Gly Gln Gly Thr Thr Val
            100                 105                 110

Thr Val Ser Ser
        115
```

<210> SEQ ID NO 54
<211> LENGTH: 348
<212> TYPE: DNA
<213> ORGANISM: artificial sequence
<220> FEATURE:
<223> OTHER INFORMATION: anti-EpCAM VH

<400> SEQUENCE: 54

```
caggtgaaac tgcaggagtc aggacctggc ctagtgcagc cctcacagag cctgtccatc        60
acctgcacag tctctggttt ctcattaact agctatggtg tacactgggt tcgccagtct       120
ccaggaaagg gtctggagtg gctgggagtg atatggagtg gtggaagcac agactataat       180
gcagctttca tatccagact gagcatcagc aaggacaatt ccaagagcca agttttcttt       240
aaaatgaaca gtctgcaagc taatgacaca gccatatatt actgtgccag aatggagaac       300
tggtcgtttg cttactgggg ccaagggacc acggtcaccg tctcctcc                    348
```

<210> SEQ ID NO 55
<211> LENGTH: 107
<212> TYPE: PRT
<213> ORGANISM: artificial sequence
<220> FEATURE:
<223> OTHER INFORMATION: anti-EpCAM VL

<400> SEQUENCE: 55

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80
```

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys
            100                 105

<210> SEQ ID NO 56
<211> LENGTH: 321
<212> TYPE: DNA
<213> ORGANISM: artificial sequence
<220> FEATURE:
<223> OTHER INFORMATION: anti-EpCAM VL

<400> SEQUENCE: 56
gatatccagc tgacccagtc tcaaaaattc atgtccacat cagtaggaga cagggtcagc    60
gtcacctgca aggccagtca gaatgtgggt actaatgtag cctggtatca acagaaacca   120
gggcaatctc ctaaagcact gatttactcg gcatcctacc ggtacagtgg agtccctgat   180
cgcttcacag gcagtggatc tgggacagat ttcactctca ccatcagcaa tgtgcagtct   240
gaagacttgg cagagtattt ctgtcagcaa tataacagct atccgctcac gttcggtgct   300
gggaccaagc tcgagatcaa a                                             321

<210> SEQ ID NO 57
<211> LENGTH: 121
<212> TYPE: PRT
<213> ORGANISM: artificial sequence
<220> FEATURE:
<223> OTHER INFORMATION: anti-CD3 VH (modified antiCD3 VH-region
      derived from OKT-3)

<400> SEQUENCE: 57

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu
        115                 120

<210> SEQ ID NO 58
<211> LENGTH: 362
<212> TYPE: DNA
<213> ORGANISM: artificial sequence
<220> FEATURE:
<223> OTHER INFORMATION: anti-CD3 VH (modified antiCD3 VH-region
      derived from OKT-3)

<400> SEQUENCE: 58
gatatcaaac tgcagcagtc aggggctgaa ctggcaagac ctggggcctc gtgaagatgt    60
cctgcaagac ttctggctac acctttacta ggtacacgat gcactgggta aaacagaggc   120

```
ctggacaggg tctggaatgg attggataca ttaatcctag ccgtggttat actaattaca    180
atcagaagtt caaggacaag gccacattga ctacagacaa atcctccagc acagcctaca    240
tgcaactgag cagcctgaca tctgaggact ctgcagtcta ttactgtgca agatattatg    300
atgatcatta ctgccttgac tactggggcc aaggcaccac tctcacagtc tcctcagtcg    360
aa                                                                   362
```

<210> SEQ ID NO 59
<211> LENGTH: 492
<212> TYPE: PRT
<213> ORGANISM: artificial sequence
<220> FEATURE:
<223> OTHER INFORMATION: scFv EpCAMxCD3 (modified antiCD3 VH-region derived from OKT-3)

<400> SEQUENCE: 59

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Gly Gly Gly Gly Ser
            100                 105                 110

Gly Gly Gly Gly Ser Gly Gly Gly Ser Gln Val Lys Leu Gln Glu
        115                 120                 125

Ser Gly Pro Gly Leu Val Gln Pro Ser Gln Ser Leu Ser Ile Thr Cys
    130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
        195                 200                 205

Ala Asn Asp Thr Ala Ile Tyr Tyr Cys Ala Arg Met Glu Asn Trp Ser
    210                 215                 220

Phe Ala Tyr Trp Gly Gln Gly Thr Thr Val Thr Val Ser Ser Gly Gly
225                 230                 235                 240

Gly Gly Ser Asp Ile Lys Leu Gln Gln Ser Gly Ala Glu Leu Ala Arg
                245                 250                 255

Pro Gly Ala Ser Val Lys Met Ser Cys Lys Thr Ser Gly Tyr Thr Phe
            260                 265                 270

Thr Arg Tyr Thr Met His Trp Val Lys Gln Arg Pro Gly Gln Gly Leu
        275                 280                 285

Glu Trp Ile Gly Tyr Ile Asn Pro Ser Arg Gly Tyr Thr Asn Tyr Asn
    290                 295                 300

Gln Lys Phe Lys Asp Lys Ala Thr Leu Thr Thr Asp Lys Ser Ser Ser
```

-continued

```
            305                 310                 315                 320
Thr Ala Tyr Met Gln Leu Ser Ser Leu Thr Ser Glu Asp Ser Ala Val
                    325                 330                 335
Tyr Tyr Cys Ala Arg Tyr Tyr Asp Asp His Tyr Cys Leu Asp Tyr Trp
                340                 345                 350
Gly Gln Gly Thr Thr Leu Thr Val Ser Ser Val Glu Gly Gly Ser Gly
            355                 360                 365
Gly Ser Gly Gly Ser Gly Gly Ser Gly Gly Val Asp Asp Ile Gln Leu
        370                 375                 380
Thr Gln Ser Pro Ala Ile Met Ser Ala Ser Pro Gly Glu Lys Val Thr
385                 390                 395                 400
Met Thr Cys Arg Ala Ser Ser Ser Val Ser Tyr Met Asn Trp Tyr Gln
                405                 410                 415
Gln Lys Ser Gly Thr Ser Pro Lys Arg Trp Ile Tyr Asp Thr Ser Lys
            420                 425                 430
Val Ala Ser Gly Val Pro Tyr Arg Phe Ser Gly Ser Gly Ser Gly Thr
            435                 440                 445
Ser Tyr Ser Leu Thr Ile Ser Ser Met Glu Ala Glu Asp Ala Ala Thr
        450                 455                 460
Tyr Tyr Cys Gln Gln Trp Ser Ser Asn Pro Leu Thr Phe Gly Ala Gly
465                 470                 475                 480
Thr Lys Leu Glu Leu Lys His His His His His His
                485                 490

<210> SEQ ID NO 60
<211> LENGTH: 1479
<212> TYPE: DNA
<213> ORGANISM: artificial sequence
<220> FEATURE:
<223> OTHER INFORMATION: scFv EpCAMxCD3 (modified antiCD3 VH-region
      derived from OKT-3)

<400> SEQUENCE: 60
gatatccagc tgacccagtc tcaaaaattc atgtccacat cagtaggaga cagggtcagc          60
gtcacctgca aggccagtca gaatgtgggt actaatgtag cctggtatca acagaaacca         120
gggcaatctc ctaaagcact gatttactcg gcatcctacc ggtacagtgg agtccctgat         180
cgcttcacag gcagtggatc tgggacagat ttcactctca ccatcagcaa tgtgcagtct         240
gaagacttgg cagagtattt ctgtcagcaa tataacagct atccgctcac gttcggtgct         300
gggaccaagc tcgagatcaa aggtggtggt ggttctggcg gcggcggctc cggtggtggt         360
ggttctcagg tgaaactgca ggagtcagga cctggcctag tgcagccctc acagagcctg         420
tccatcacct gcacagtctc tggtttctca ttaactagct atggtgtaca ctgggttcgc         480
cagtctccag gaaagggtct ggagtggctg ggagtgatat ggagtggtgg aagcacagac         540
tataatgcag ctttcatatc cagactgagc atcagcaagg acaattccaa gagccaagtt         600
ttctttaaaa tgaacagtct gcaagctaat gacacagcca tatattactg tgccagaatg         660
gagaactggt cgtttgctta ctggggccaa gggaccacgg tcaccgtctc ctccggaggt         720
ggtggatccg atatcaaact gcagcagtca ggggctgaac tggcaagacc tggggcctca         780
gtgaagatgt cctgcaagac ttctggctac acctttacta ggtacacgat gcactgggta         840
aaacagagag ctggacaggg tctggaatgg attggataca ttaatcctag ccgtggttat         900
actaattaca atcagaagtt caaggacaag gccacattga ctacagacaa atcctccagc         960
acagcctaca tgcaactgag cagcctgaca tctgaggact ctgcagtcta ttactgtgca        1020
```

```
agatattatg atgatcatta ctgccttgac tactggggcc aaggcaccac tctcacagtc   1080
tcctcagtcg aaggtggaag tggaggttct ggtggaagtg gaggttcagg tggagtcgac   1140
gacattcagc tgacccagtc tccagcaatc atgtctgcat ctccagggga aaggtcacc    1200
```
```
atgacctgca gagccagttc aagtgtaagt tacatgaact ggtaccagca gaagtcaggc   1260
acctccccca aaagatggat ttatgacaca tccaaagtgg cttctggagt cccttatcgc   1320
ttcagtggca gtgggtctgg gacctcatac tctctcacaa tcagcagcat ggaggctgaa   1380
gatgctgcca cttattactg ccaacagtgg agtagtaacc cgctcacgtt cggtgctggg   1440
accaagctgg agctgaaaca tcatcaccat catcattag                          1479
```

<210> SEQ ID NO 61
<211> LENGTH: 492
<212> TYPE: PRT
<213> ORGANISM: artificial sequence
<220> FEATURE:
<223> OTHER INFORMATION: scFv EpCAMxCD3 with M1 mutant in anti-CD3 part

<400> SEQUENCE: 61

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Gly Gly Gly Gly Ser
            100                 105                 110

Gly Gly Gly Gly Ser Gly Gly Gly Ser Gln Val Lys Leu Gln Glu
        115                 120                 125

Ser Gly Pro Gly Leu Val Gln Pro Ser Gln Ser Leu Ser Ile Thr Cys
    130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
        195                 200                 205

Ala Asn Asp Thr Ala Ile Tyr Tyr Cys Ala Arg Met Glu Asn Trp Ser
    210                 215                 220

Phe Ala Tyr Trp Gly Gln Gly Thr Thr Val Thr Val Ser Ser Gly Gly
225                 230                 235                 240

Gly Gly Ser Asp Ile Lys Leu Gln Gln Ser Gly Ala Glu Leu Ala Arg
                245                 250                 255

Pro Gly Ala Ser Val Lys Met Ser Cys Lys Thr Ser Gly Tyr Thr Phe
            260                 265                 270

Thr Arg Tyr Thr Met His Trp Val Lys Gln Arg Pro Gly Gln Gly Leu
```

-continued

```
                275                 280                 285
Glu Trp Ile Gly Tyr Ile Asn Pro Ser Arg Gly Tyr Thr Asn Tyr Asn
            290                 295                 300
Gln Lys Phe Lys Asp Lys Ala Thr Leu Thr Thr Asp Lys Ser Ser Ser
305                 310                 315                 320
Thr Ala Tyr Met Gln Leu Ser Ser Leu Thr Ser Glu Asp Ser Ala Val
                325                 330                 335
Tyr Tyr Cys Ala Arg His Tyr Asp Asp His Tyr Cys Leu Asp Tyr Trp
            340                 345                 350
Gly Gln Gly Thr Thr Leu Thr Val Ser Ser Val Glu Gly Gly Ser Gly
            355                 360                 365
Gly Ser Gly Gly Ser Gly Gly Ser Gly Gly Val Asp Asp Ile Gln Leu
        370                 375                 380
Thr Gln Ser Pro Ala Ile Met Ser Ala Ser Pro Gly Glu Lys Val Thr
385                 390                 395                 400
Met Thr Cys Arg Ala Ser Ser Ser Val Ser Tyr Met Asn Trp Tyr Gln
                405                 410                 415
Gln Lys Ser Gly Thr Ser Pro Lys Arg Trp Ile Tyr Asp Thr Ser Lys
            420                 425                 430
Val Ala Ser Gly Val Pro Tyr Arg Phe Ser Gly Ser Gly Ser Gly Thr
        435                 440                 445
Ser Tyr Ser Leu Thr Ile Ser Ser Met Glu Ala Glu Asp Ala Ala Thr
    450                 455                 460
Tyr Tyr Cys Gln Gln Trp Ser Ser Asn Pro Leu Thr Phe Gly Ala Gly
465                 470                 475                 480
Thr Lys Leu Glu Leu Lys His His His His His His
                485                 490

<210> SEQ ID NO 62
<211> LENGTH: 1479
<212> TYPE: DNA
<213> ORGANISM: artificial sequence
<220> FEATURE:
<223> OTHER INFORMATION: scFv EpCAMxCD3 with M1 mutant in anti-CD3 part

<400> SEQUENCE: 62
gatatccagc tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgctcac gttcggtgct     300
gggaccaagc tcgagatcaa aggtggtggt ggttctggcg gcggcggctc cggtggtggt     360
ggttctcagg tgaaactgca ggagtcagga cctggcctag tgcagccctc acagagcctg     420
tccatcacct gcacagtctc tggtttctca ttaactagct atggtgtaca ctgggttcgc     480
cagtctccag gaaagggtct ggagtggctg gagtgatat ggagtggtgg aagcacagac     540
tataatgcag ctttcatatc cagactgagc atcagcaagg acaattccaa gagccaagtt     600
ttctttaaaa tgaacagtct gcaagctaat gacacagcca tatattactg tgccagaatg     660
gagaactggt cgtttgctta ctggggccaa gggaccacgg tcaccgtctc ctccggaggt     720
ggtggatccg atatcaaact gcagcagtca ggggctgaac tggcaagacc tgggggcctca     780
gtgaagatgt cctgcaagac ttctggctac acctttacta ggtacacgat gcactgggta     840
```

```
aaacagaggc ctggacaggg tctggaatgg attggataca ttaatcctag ccgtggttat    900
actaattaca atcagaagtt caaggacaag gccacattga ctacagacaa atcctccagc    960
acagcctaca tgcaactgag cagcctgaca tctgaggact ctgcagtcta ttactgtgca   1020
agacattatg atgatcatta ctgccttgac tactggggcc aaggcaccac tctcacagtc   1080
tcctcagtcg aaggtggaag tggaggttct ggtggaagtg gaggttcagg tggagtcgac   1140
gacattcagc tgacccagtc tccagcaatc atgtctgcat ctccagggga aaggtcacc    1200
atgacctgca gagccagttc aagtgtaagt tacatgaact ggtaccagca gaagtcaggc   1260
acctccccca aaagatggat ttatgacaca tccaaagtgg cttctggagt cccttatcgc   1320
ttcagtggca gtgggtctgg gacctcatac tctctcacaa tcagcagcat ggaggctgaa   1380
gatgctgcca cttattactg ccaacagtgg agtagtaacc cgctcacgtt cggtgctggg   1440
accaagctgg agctgaaaca tcatcaccat catcattag                          1479
```

<210> SEQ ID NO 63
<211> LENGTH: 492
<212> TYPE: PRT
<213> ORGANISM: artificial sequence
<220> FEATURE:
<223> OTHER INFORMATION: scFv EpCAMxCD3 with M4 mutant in anti-CD3 part

<400> SEQUENCE: 63

Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Gly Gly Gly Gly Ser
            100                 105                 110

Gly Gly Gly Gly Ser Gly Gly Gly Ser Gln Val Lys Leu Gln Glu
        115                 120                 125

Ser Gly Pro Gly Leu Val Gln Pro Ser Gln Ser Leu Ser Ile Thr Cys
    130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
        195                 200                 205

Ala Asn Asp Thr Ala Ile Tyr Tyr Cys Ala Arg Met Glu Asn Trp Ser
    210                 215                 220

Phe Ala Tyr Trp Gly Gln Gly Thr Thr Val Thr Val Ser Ser Gly Gly
225                 230                 235                 240

Gly Gly Ser Asp Ile Lys Leu Gln Gln Ser Gly Ala Glu Leu Ala Arg
                245                 250                 255

-continued

```
Pro Gly Ala Ser Val Lys Met Ser Cys Lys Thr Ser Gly Tyr Thr Phe
            260                 265                 270
Thr Arg Tyr Thr Met His Trp Val Lys Gln Arg Pro Gly Gln Gly Leu
        275                 280                 285
Glu Trp Ile Gly Tyr Ile Asn Pro Ser Arg Gly Tyr Thr Asn Tyr Asn
    290                 295                 300
Gln Lys Phe Lys Asp Lys Ala Thr Leu Thr Thr Asp Lys Ser Ser Ser
305                 310                 315                 320
Thr Ala Tyr Met Gln Leu Ser Ser Leu Thr Ser Glu Asp Ser Ala Val
                325                 330                 335
Tyr Tyr Cys Ala Arg Tyr Ser Asp Asp His Tyr Cys Leu Asp Tyr Trp
            340                 345                 350
Gly Gln Gly Thr Thr Leu Thr Val Ser Ser Val Glu Gly Gly Ser Gly
        355                 360                 365
Gly Ser Gly Gly Ser Gly Gly Ser Gly Gly Val Asp Asp Ile Gln Leu
    370                 375                 380
Thr Gln Ser Pro Ala Ile Met Ser Ala Ser Pro Gly Glu Lys Val Thr
385                 390                 395                 400
Met Thr Cys Arg Ala Ser Ser Ser Val Ser Tyr Met Asn Trp Tyr Gln
                405                 410                 415
Gln Lys Ser Gly Thr Ser Pro Lys Arg Trp Ile Tyr Asp Thr Ser Lys
            420                 425                 430
Val Ala Ser Gly Val Pro Tyr Arg Phe Ser Gly Ser Gly Ser Gly Thr
        435                 440                 445
Ser Tyr Ser Leu Thr Ile Ser Ser Met Glu Ala Glu Asp Ala Ala Thr
    450                 455                 460
Tyr Tyr Cys Gln Gln Trp Ser Ser Asn Pro Leu Thr Phe Gly Ala Gly
465                 470                 475                 480
Thr Lys Leu Glu Leu Lys His His His His His
                485                 490
```

<210> SEQ ID NO 64
<211> LENGTH: 1479
<212> TYPE: DNA
<213> ORGANISM: artificial sequence
<220> FEATURE:
<223> OTHER INFORMATION: scFv EpCAMxCD3 with M4 mutant in anti-CD3 part

<400> SEQUENCE: 64

```
gatatccagc tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgctcac gttcggtgct     300
gggaccaagc tcgagatcaa aggtggtggt ggttctggcg gcggcggctc cggtggtggt     360
ggttctcagg tgaaactgca ggagtcagga cctggcctag tgcagccctc acagagcctg     420
tccatcacct gcacagtctc tggtttctca ttaactagct atggtgtaca ctgggttcgc     480
cagtctccag gaaagggtct ggagtggctg ggagtgatat ggagtggtgg aagcacagac     540
tataatgcag ctttcatatc cagactgagc atcagcaagg acaattccaa gagccaagtt     600
ttctttaaaa tgaacagtct gcaagctaat gacacagcca tatattactg tgccagaatg     660
gagaactggt cgtttgctta ctggggccaa gggaccacgg tcaccgtctc ctccggaggt     720
```

```
ggtggatccg atatcaaact gcagcagtca ggggctgaac tggcaagacc tggggcctca    780
gtgaagatgt cctgcaagac ttctggctac acctttacta ggtacacgat gcactgggta    840
aaacagaggc ctggacaggg tctggaatgg attggataca ttaatcctag ccgtggttat    900
actaattaca atcagaagtt caaggacaag gccacattga ctacagacaa atcctccagc    960
acagcctaca tgcaactgag cagcctgaca tctgaggact ctgcagtcta ttactgtgca   1020
agatatagtg atgatcatta ctgccttgac tactggggcc aaggcaccac tctcacagtc   1080
tcctcagtcg aaggtggaag tggaggttct ggtggaagtg gaggttcagg tggagtcgac   1140
gacattcagc tgacccagtc tccagcaatc atgtctgcat ctccagggga aaggtcacc    1200 atgacctgca gagccagttc aagtgtaagt tacatgaact ggtaccagca gaagtcaggc   1260
acctccccca aaagatggat ttatgacaca tccaaagtgg cttctggagt cccttatcgc   1320
ttcagtggca gtgggtctgg gacctcatac tctctcacaa tcagcagcat ggaggctgaa   1380
gatgctgcca cttattactg ccaacagtgg agtagtaacc cgctcacgtt cggtgctggg   1440
accaagctgg agctgaaaca tcatcaccat catcattag                          1479
```

<210> SEQ ID NO 65
<211> LENGTH: 492
<212> TYPE: PRT
<213> ORGANISM: artificial sequence
<220> FEATURE:
<223> OTHER INFORMATION: scFv EpCAMxCD3 with M7 mutant in anti-CD3 part

<400> SEQUENCE: 65

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Gly Gly Gly Ser
            100                 105                 110

Gly Gly Gly Gly Ser Gly Gly Gly Ser Gln Val Lys Leu Gln Glu
        115                 120                 125

Ser Gly Pro Gly Leu Val Gln Pro Ser Gln Ser Leu Ser Ile Thr Cys
130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
        195                 200                 205

Ala Asn Asp Thr Ala Ile Tyr Tyr Cys Ala Arg Met Glu Asn Trp Ser
    210                 215                 220
```

Phe Ala Tyr Trp Gly Gln Gly Thr Thr Val Thr Val Ser Ser Gly Gly
225                 230                 235                 240

Gly Gly Ser Asp Ile Lys Leu Gln Gln Ser Gly Ala Glu Leu Ala Arg
            245                 250                 255

Pro Gly Ala Ser Val Lys Met Ser Cys Lys Thr Ser Gly Tyr Thr Phe
        260                 265                 270

Thr Arg Tyr Thr Met His Trp Val Lys Gln Arg Pro Gly Gln Gly Leu
    275                 280                 285

Glu Trp Ile Gly Tyr Ile Asn Pro Ser Arg Gly Tyr Thr Asn Tyr Asn
290                 295                 300

Gln Lys Phe Lys Asp Lys Ala Thr Leu Thr Thr Asp Lys Ser Ser Ser
305                 310                 315                 320

Thr Ala Tyr Met Gln Leu Ser Ser Leu Thr Ser Glu Asp Ser Ala Val
            325                 330                 335

Tyr Tyr Cys Ala Arg Tyr Tyr Asp Ala His Tyr Cys Leu Asp Tyr Trp
        340                 345                 350

Gly Gln Gly Thr Thr Leu Thr Val Ser Ser Val Glu Gly Gly Ser Gly
    355                 360                 365

Gly Ser Gly Gly Ser Gly Gly Ser Gly Gly Val Asp Asp Ile Gln Leu
        370                 375                 380

Thr Gln Ser Pro Ala Ile Met Ser Ala Ser Pro Gly Glu Lys Val Thr
385                 390                 395                 400

Met Thr Cys Arg Ala Ser Ser Val Ser Tyr Met Asn Trp Tyr Gln
            405                 410                 415

Gln Lys Ser Gly Thr Ser Pro Lys Arg Trp Ile Tyr Asp Thr Ser Lys
            420                 425                 430

Val Ala Ser Gly Val Pro Tyr Arg Phe Ser Gly Ser Gly Ser Gly Thr
        435                 440                 445

Ser Tyr Ser Leu Thr Ile Ser Ser Met Glu Ala Glu Asp Ala Ala Thr
    450                 455                 460

Tyr Tyr Cys Gln Gln Trp Ser Ser Asn Pro Leu Thr Phe Gly Ala Gly
465                 470                 475                 480

Thr Lys Leu Glu Leu Lys His His His His His His
            485                 490

<210> SEQ ID NO 66
<211> LENGTH: 1479
<212> TYPE: DNA
<213> ORGANISM: artificial sequence
<220> FEATURE:
<223> OTHER INFORMATION: scFv EpCAMxCD3 with M7 mutant in anti-CD3 part

<400> SEQUENCE: 66
gatatccagc tgacccagtc tcaaaaattc atgtccacat cagtaggaga cagggtcagc        60
gtcacctgca aggccagtca gaatgtgggt actaatgtag cctggtatca acagaaacca       120
gggcaatctc ctaaagcact gatttactcg gcatcctacc ggtacagtgg agtccctgat       180
cgcttcacag gcagtggatc tgggacagat ttcactctca ccatcagcaa tgtgcagtct       240
gaagacttgg cagagtattt ctgtcagcaa tataacagct atccgctcac gttcggtgct       300
gggaccaagc tcgagatcaa aggtggtggt ggttctggcg gcggcggctc cggtggtggt       360
ggttctcagg tgaaactgca ggagtcagga cctggcctag tgcagccctc acagagcctg       420
tccatcacct gcacagtctc tggtttctca ttaactagct atggtgtaca ctgggttcgc       480
cagtctccag gaaagggtct ggagtggctg ggagtgatat ggagtggtgg aagcacagac       540

```
tataatgcag ctttcatatc cagactgagc atcagcaagg acaattccaa gagccaagtt    600
ttctttaaaa tgaacagtct gcaagctaat gacacagcca tatattactg tgccagaatg    660
gagaactggt cgtttgctta ctggggccaa gggaccacgg tcaccgtctc ctccggaggt    720
ggtggatccg atatcaaact gcagcagtca ggggctgaac tggcaagacc tggggcctca    780
gtgaagatgt cctgcaagac ttctggctac acctttacta ggtacacgat gcactgggta    840
aaacagaggc ctggacaggg tctggaatgg attggataca ttaatcctag ccgtggttat    900
actaattaca atcagaagtt caaggacaag gccacattga ctacagacaa atcctccagc    960
acagcctaca tgcaactgag cagcctgaca tctgaggact ctgcagtcta ttactgtgca   1020
agatattatg atgctcatta ctgccttgac tactggggcc aaggcaccac tctcacagtc   1080
tcctcagtcg aaggtggaag tggaggttct ggtggaagtg gaggttcagg tggagtcgac   1140
gacattcagc tgacccagtc tccagcaatc atgtctgcat ctccagggga aaggtcacc   1200 atgacctgca gagccagttc aagtgtaagt tacatgaact ggtaccagca gaagtcaggc   1260
acctccccca aaagatggat ttatgacaca tccaaagtgg cttctggagt cccttatcgc   1320
ttcagtggca gtgggtctgg gacctcatac tctctcacaa tcagcagcat ggaggctgaa   1380
gatgctgcca cttattactg ccaacagtgg agtagtaacc cgctcacgtt cggtgctggg   1440
accaagctgg agctgaaaca tcatcaccat catcattag                          1479
```

<210> SEQ ID NO 67
<211> LENGTH: 492
<212> TYPE: PRT
<213> ORGANISM: artificial sequence
<220> FEATURE:
<223> OTHER INFORMATION: scFv EpCAMxCD3 with M9 mutant in anti-CD3 part

<400> SEQUENCE: 67

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Gly Gly Gly Gly Ser
            100                 105                 110

Gly Gly Gly Gly Ser Gly Gly Gly Ser Gln Val Lys Leu Gln Glu
        115                 120                 125

Ser Gly Pro Gly Leu Val Gln Pro Ser Gln Ser Leu Ser Ile Thr Cys
    130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
```

-continued

```
                195                 200                 205
Ala Asn Asp Thr Ala Ile Tyr Tyr Cys Ala Arg Met Glu Asn Trp Ser
    210                 215                 220
Phe Ala Tyr Trp Gly Gln Gly Thr Thr Val Thr Val Ser Ser Gly Gly
225                 230                 235                 240
Gly Gly Ser Asp Ile Lys Leu Gln Gln Ser Gly Ala Glu Leu Ala Arg
                245                 250                 255
Pro Gly Ala Ser Val Lys Met Ser Cys Lys Thr Ser Gly Tyr Thr Phe
                260                 265                 270
Thr Arg Tyr Thr Met His Trp Val Lys Gln Arg Pro Gly Gln Gly Leu
            275                 280                 285
Glu Trp Ile Gly Tyr Ile Asn Pro Ser Arg Gly Tyr Thr Asn Tyr Asn
290                 295                 300
Gln Lys Phe Lys Asp Lys Ala Thr Leu Thr Thr Asp Lys Ser Ser Ser
305                 310                 315                 320
Thr Ala Tyr Met Gln Leu Ser Ser Leu Thr Ser Glu Asp Ser Ala Val
                325                 330                 335
Tyr Tyr Cys Ala Arg Tyr Tyr Asp Asp Gln Tyr Cys Leu Asp Tyr Trp
                340                 345                 350
Gly Gln Gly Thr Thr Leu Thr Val Ser Ser Val Glu Gly Gly Ser Gly
                355                 360                 365
Gly Ser Gly Gly Ser Gly Gly Ser Gly Gly Val Asp Asp Ile Gln Leu
            370                 375                 380
Thr Gln Ser Pro Ala Ile Met Ser Ala Ser Pro Gly Glu Lys Val Thr
385                 390                 395                 400
Met Thr Cys Arg Ala Ser Ser Ser Val Ser Tyr Met Asn Trp Tyr Gln
                405                 410                 415
Gln Lys Ser Gly Thr Ser Pro Lys Arg Trp Ile Tyr Asp Thr Ser Lys
                420                 425                 430
Val Ala Ser Gly Val Pro Tyr Arg Phe Ser Gly Ser Gly Ser Gly Thr
            435                 440                 445
Ser Tyr Ser Leu Thr Ile Ser Ser Met Glu Ala Glu Asp Ala Ala Thr
        450                 455                 460
Tyr Tyr Cys Gln Gln Trp Ser Ser Asn Pro Leu Thr Phe Gly Ala Gly
465                 470                 475                 480
Thr Lys Leu Glu Leu Lys His His His His His
                485                 490
```

<210> SEQ ID NO 68
<211> LENGTH: 1479
<212> TYPE: DNA
<213> ORGANISM: artificial sequence
<220> FEATURE:
<223> OTHER INFORMATION: scFv EpCAMxCD3 with M9 mutant in anti-CD3 part

<400> SEQUENCE: 68

```
gatatccagc tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgctcac gttcggtgct     300
gggaccaagc tcgagatcaa aggtggtggt ggttctggcg gcggcggctc cggtggtggt     360
ggttctcagg tgaaactgca ggagtcagga cctggcctag tgcagccctc acagagcctg     420
```

```
tccatcacct gcacagtctc tggtttctca ttaactagct atggtgtaca ctgggttcgc      480
cagtctccag gaaagggtct ggagtggctg ggagtgatat ggagtggtgg aagcacagac      540
tataatgcag ctttcatatc cagactgagc atcagcaagg acaattccaa gagccaagtt      600
ttctttaaaa tgaacagtct gcaagctaat gacacagcca tatattactg tgccagaatg      660
gagaactggt cgtttgctta ctggggccaa gggaccacgg tcaccgtctc ctccggaggt      720
ggtggatccg atatcaaact gcagcagtca ggggctgaac tggcaagacc tggggcctca      780
gtgaagatgt cctgcaagac ttctggctac acctttacta ggtacacgat gcactgggta      840
aaacagaggc ctggacaggg tctggaatgg attggataca ttaatcctag ccgtggttat      900
actaattaca atcagaagtt caaggacaag gccacattga ctacagacaa atcctccagc      960
acagcctaca tgcaactgag cagcctgaca tctgaggact ctgcagtcta ttactgtgca     1020
agatattatg atgatcaata ctgccttgac tactggggcc aaggcaccac tctcacagtc     1080
tcctcagtcg aaggtggaag tggaggttct ggtggaagtg gaggttcagg tggagtcgac     1140
gacattcagc tgacccagtc tccagcaatc atgtctgcat ctccagggga aaggtcacc      1200 atgacctgca gagccagttc aagtgtaagt tacatgaact ggtaccagca gaagtcaggc     1260
acctccccca aaagatggat ttatgacaca tccaaagtgg cttctggagt cccttatcgc     1320
ttcagtggca gtgggtctgg gacctcatac tctctcacaa tcagcagcat ggaggctgaa     1380
gatgctgcca cttattactg ccaacagtgg agtagtaacc cgctcacgtt cggtgctggg     1440
accaagctgg agctgaaaca tcatcaccat catcattag                            1479
```

<210> SEQ ID NO 69
<211> LENGTH: 492
<212> TYPE: PRT
<213> ORGANISM: artificial sequence
<220> FEATURE:
<223> OTHER INFORMATION: scFv EpCAMxCD3 with M10 mutant in anti-CD3 part

<400> SEQUENCE: 69

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Gly Gly Gly Gly Ser
            100                 105                 110

Gly Gly Gly Gly Ser Gly Gly Gly Ser Gln Val Lys Leu Gln Glu
        115                 120                 125

Ser Gly Pro Gly Leu Val Gln Pro Ser Gln Ser Leu Ser Ile Thr Cys
    130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175
```

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
        195                 200                 205

Ala Asn Asp Thr Ala Ile Tyr Tyr Cys Ala Arg Met Glu Asn Trp Ser
    210                 215                 220

Phe Ala Tyr Trp Gly Gln Gly Thr Thr Val Thr Val Ser Ser Gly Gly
225                 230                 235                 240

Gly Gly Ser Asp Ile Lys Leu Gln Gln Ser Gly Ala Glu Leu Ala Arg
            245                 250                 255

Pro Gly Ala Ser Val Lys Met Ser Cys Lys Thr Ser Gly Tyr Thr Phe
        260                 265                 270

Thr Arg Tyr Thr Met His Trp Val Lys Gln Arg Pro Gly Gln Gly Leu
    275                 280                 285

Glu Trp Ile Gly Tyr Ile Asn Pro Ser Arg Gly Tyr Thr Asn Tyr Asn
            290                 295                 300

Gln Lys Phe Lys Asp Lys Ala Thr Leu Thr Thr Asp Lys Ser Ser Ser
305                 310                 315                 320

Thr Ala Tyr Met Gln Leu Ser Ser Leu Thr Ser Glu Asp Ser Ala Val
            325                 330                 335

Tyr Tyr Cys Ala Arg Tyr Tyr Asp Asp Pro Tyr Cys Leu Asp Tyr Trp
        340                 345                 350

Gly Gln Gly Thr Thr Leu Thr Val Ser Ser Val Glu Gly Gly Ser Gly
    355                 360                 365

Gly Ser Gly Gly Ser Gly Gly Ser Gly Gly Val Asp Asp Ile Gln Leu
            370                 375                 380

Thr Gln Ser Pro Ala Ile Met Ser Ala Ser Pro Gly Glu Lys Val Thr
385                 390                 395                 400

Met Thr Cys Arg Ala Ser Ser Ser Val Ser Tyr Met Asn Trp Tyr Gln
            405                 410                 415

Gln Lys Ser Gly Thr Ser Pro Lys Arg Trp Ile Tyr Asp Thr Ser Lys
        420                 425                 430

Val Ala Ser Gly Val Pro Tyr Arg Phe Ser Gly Ser Gly Ser Gly Thr
    435                 440                 445

Ser Tyr Ser Leu Thr Ile Ser Ser Met Glu Ala Glu Asp Ala Ala Thr
            450                 455                 460

Tyr Tyr Cys Gln Gln Trp Ser Ser Asn Pro Leu Thr Phe Gly Ala Gly
465                 470                 475                 480

Thr Lys Leu Glu Leu Lys His His His His His
            485                 490

<210> SEQ ID NO 70
<211> LENGTH: 1479
<212> TYPE: DNA
<213> ORGANISM: artificial sequence
<220> FEATURE:
<223> OTHER INFORMATION: scFv EpCAMxCD3 with M10 mutant in anti-CD3 part

<400> SEQUENCE: 70
gatatccagc tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240

```
gaagacttgg cagagtattt ctgtcagcaa tataacagct atccgctcac gttcggtgct      300
gggaccaagc tcgagatcaa aggtggtggt ggttctggcg gcggcggctc cggtggtggt      360
ggttctcagg tgaaactgca ggagtcagga cctggcctag tgcagccctc acagagcctg      420
tccatcacct gcacagtctc tggtttctca ttaactagct atggtgtaca ctgggttcgc      480
cagtctccag gaaagggtct ggagtggctg ggagtgatat ggagtggtgg aagcacagac      540
tataatgcag ctttcatatc cagactgagc atcagcaagg acaattccaa gagccaagtt      600
ttctttaaaa tgaacagtct gcaagctaat gacacagcca tatattactg tgccagaatg      660
gagaactggt cgtttgctta ctggggccaa gggaccacgg tcaccgtctc ctccggaggt      720
ggtggatccg atatcaaact gcagcagtca ggggctgaac tggcaagacc tggggcctca      780
gtgaagatgt cctgcaagac ttctggctac acctttacta ggtacacgat gcactgggta      840
aaacagaggc ctggacaggg tctggaatgg attggataca ttaatcctag ccgtggttat      900
actaattaca atcagaagtt caaggacaag gccacattga ctacagacaa atcctccagc      960
acagcctaca tgcaactgag cagcctgaca tctgaggact ctgcagtcta ttactgtgca     1020
agatattatg atgatcctta ctgccttgac tactggggcc aaggcaccac tctcacagtc     1080
tcctcagtcg aaggtggaag tggaggttct ggtggaagtg gaggttcagg tggagtcgac     1140
gacattcagc tgacccagtc tccagcaatc atgtctgcat ctccagggga aaggtcacc      1200 atgacctgca gagccagttc aagtgtaagt tacatgaact ggtaccagca gaagtcaggc     1260
acctccccca aaagatggat ttatgacaca tccaaagtgg cttctggagt cccttatcgc     1320
ttcagtggca gtgggtctgg gacctcatac tctctcacaa tcagcagcat ggaggctgaa     1380
gatgctgcca cttattactg ccaacagtgg agtagtaacc cgctcacgtt cggtgctggg     1440
accaagctgg agctgaaaca tcatcaccat catcattag                            1479
```

<210> SEQ ID NO 71
<211> LENGTH: 492
<212> TYPE: PRT
<213> ORGANISM: artificial sequence
<220> FEATURE:
<223> OTHER INFORMATION: scFv EpCAMxCD3 with M11 mutant in anti-CD3 part

<400> SEQUENCE: 71

Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Gly Gly Gly Gly Ser
            100                 105                 110

Gly Gly Gly Gly Ser Gly Gly Gly Ser Gln Val Lys Leu Gln Glu
        115                 120                 125

Ser Gly Pro Gly Leu Val Gln Pro Ser Gln Ser Leu Ser Ile Thr Cys
    130                 135                 140

| | | | | | | | | | | | |
|---|---|---|---|---|---|---|---|---|---|---|---|
|Thr|Val|Ser|Gly|Phe|Ser|Leu|Thr|Ser|Tyr|Gly|Val|His|Trp|Val|Arg|
|145| | | | |150| | | | |155| | | | |160|

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
            195                 200                 205

Ala Asn Asp Thr Ala Ile Tyr Tyr Cys Ala Arg Met Glu Asn Trp Ser
210                 215                 220

Phe Ala Tyr Trp Gly Gln Gly Thr Val Thr Val Ser Ser Gly Gly
225                 230                 235                 240

Gly Gly Ser Asp Ile Lys Leu Gln Gln Ser Gly Ala Glu Leu Ala Arg
            245                 250                 255

Pro Gly Ala Ser Val Lys Met Ser Cys Lys Thr Ser Gly Tyr Thr Phe
            260                 265                 270

Thr Arg Tyr Thr Met His Trp Val Lys Gln Arg Pro Gly Gln Gly Leu
        275                 280                 285

Glu Trp Ile Gly Tyr Ile Asn Pro Ser Arg Gly Tyr Thr Asn Tyr Asn
290                 295                 300

Gln Lys Phe Lys Asp Lys Ala Thr Leu Thr Thr Asp Lys Ser Ser Ser
305                 310                 315                 320

Thr Ala Tyr Met Gln Leu Ser Ser Leu Thr Ser Glu Asp Ser Ala Val
            325                 330                 335

Tyr Tyr Cys Ala Arg Tyr Phe Asn Asp His Tyr Cys Leu Asp Tyr Trp
            340                 345                 350

Gly Gln Gly Thr Thr Leu Thr Val Ser Ser Val Glu Gly Gly Ser Gly
        355                 360                 365

Gly Ser Gly Gly Ser Gly Gly Ser Gly Gly Val Asp Asp Ile Gln Leu
        370                 375                 380

Thr Gln Ser Pro Ala Ile Met Ser Ala Ser Pro Gly Glu Lys Val Thr
385                 390                 395                 400

Met Thr Cys Arg Ala Ser Ser Ser Val Ser Tyr Met Asn Trp Tyr Gln
            405                 410                 415

Gln Lys Ser Gly Thr Ser Pro Lys Arg Trp Ile Tyr Asp Thr Ser Lys
            420                 425                 430

Val Ala Ser Gly Val Pro Tyr Arg Phe Ser Gly Ser Gly Ser Gly Thr
            435                 440                 445

Ser Tyr Ser Leu Thr Ile Ser Ser Met Glu Ala Glu Asp Ala Ala Thr
        450                 455                 460

Tyr Tyr Cys Gln Gln Trp Ser Ser Asn Pro Leu Thr Phe Gly Ala Gly
465                 470                 475                 480

Thr Lys Leu Glu Leu Lys His His His His His
            485                 490

<210> SEQ ID NO 72
<211> LENGTH: 1479
<212> TYPE: DNA
<213> ORGANISM: artificial sequence
<220> FEATURE:
<223> OTHER INFORMATION: scFv EpCAMxCD3 with M11 mutant in anti-CD3 part

<400> SEQUENCE: 72
gatatccagc tgacccagtc tcaaaaattc atgtccacat cagtaggaga cagggtcagc      60
gtcacctgca aggccagtca gaatgtgggt actaatgtag cctggtatca acagaaacca     120

```
gggcaatctc ctaaagcact gatttactcg gcatcctacc ggtacagtgg agtccctgat      180
cgcttcacag gcagtggatc tgggacagat ttcactctca ccatcagcaa tgtgcagtct      240
gaagacttgg cagagtattt ctgtcagcaa tataacagct atccgctcac gttcggtgct      300
gggaccaagc tcgagatcaa aggtggtggt ggttctggcg gcggcggctc cggtggtggt      360
ggttctcagg tgaaactgca ggagtcagga cctggcctag tgcagccctc acagagcctg      420
tccatcacct gcacagtctc tggtttctca ttaactagct atggtgtaca ctgggttcgc      480
cagtctccag gaaagggtct ggagtggctg ggagtgatat ggagtggtgg aagcacagac      540
tataatgcag ctttcatatc cagactgagc atcagcaagg acaattccaa gagccaagtt      600
ttctttaaaa tgaacagtct gcaagctaat gacacagcca tatattactg tgccagaatg      660
gagaactggt cgtttgctta ctggggccaa gggaccacgg tcaccgtctc ctccggaggt      720
ggtggatccg atatcaaact gcagcagtca ggggctgaac tggcaagacc tggggcctca      780
gtgaagatgt cctgcaagac ttctggctac acctttacta ggtacacgat gcactgggta      840
aaacagaggc ctggacaggg tctggaatgg attggataca ttaatcctag ccgtggttat      900
actaattaca atcagaagtt caaggacaag gccacattga ctacagacaa atcctccagc      960
acagcctaca tgcaactgag cagcctgaca tctgaggact ctgcagtcta ttactgtgca     1020
agatatttta tgatcatta ctgccttgac tactggggcc aaggcaccac tctcacagtc     1080
tcctcagtcg aaggtggaag tggaggttct ggtggaagtg gaggttcagg tggagtcgac     1140
gacattcagc tgacccagtc tccagcaatc atgtctgcat ctccagggga aaggtcacc     1200 atgacctgca gagccagttc aagtgtaagt tacatgaact ggtaccagca gaagtcaggc     1260
acctccccca aaagatggat ttatgacaca tccaaagtgg cttctggagt cccttatcgc     1320
ttcagtggca gtgggtctgg gacctcatac tctctcacaa tcagcagcat ggaggctgaa     1380
gatgctgcca cttattactg ccaacagtgg agtagtaacc cgctcacgtt cggtgctggg     1440
accaagctgg agctgaaaca tcatcaccat catcattag                            1479
```

<210> SEQ ID NO 73
<211> LENGTH: 492
<212> TYPE: PRT
<213> ORGANISM: artificial sequence
<220> FEATURE:
<223> OTHER INFORMATION: scFv EpCAMxCD3 with M13 mutant in anti-CD3 part

<400> SEQUENCE: 73

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Gly Gly Gly Ser
                100                 105                 110

Gly Gly Gly Gly Ser Gly Gly Gly Gly Ser Gln Val Lys Leu Gln Glu
```

```
                115                 120                 125
Ser Gly Pro Gly Leu Val Gln Pro Ser Gln Ser Leu Ser Ile Thr Cys
    130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
                180                 185                 190

Lys Asp Asn Ser Lys Ser Gln Val Phe Phe Lys Met Asn Ser Leu Gln
                195                 200                 205

Ala Asn Asp Thr Ala Ile Tyr Tyr Cys Ala Arg Met Glu Asn Trp Ser
    210                 215                 220

Phe Ala Tyr Trp Gly Gln Gly Thr Thr Val Thr Val Ser Ser Gly Gly
225                 230                 235                 240

Gly Gly Ser Asp Ile Lys Leu Gln Gln Ser Gly Ala Glu Leu Ala Arg
                245                 250                 255

Pro Gly Ala Ser Val Lys Met Ser Cys Lys Thr Ser Gly Tyr Thr Phe
                260                 265                 270

Thr Arg Tyr Thr Met His Trp Val Lys Gln Arg Pro Gly Gln Gly Leu
                275                 280                 285

Glu Trp Ile Gly Tyr Ile Asn Pro Ser Arg Gly Tyr Thr Asn Tyr Asn
            290                 295                 300

Gln Lys Phe Lys Asp Lys Ala Thr Leu Thr Thr Asp Lys Ser Ser Ser
305                 310                 315                 320

Thr Ala Tyr Met Gln Leu Ser Ser Leu Thr Ser Glu Asp Ser Ala Val
                325                 330                 335

Tyr Tyr Cys Ala Arg Tyr Tyr Asn Asp Gln Tyr Cys Leu Asp Tyr Trp
                340                 345                 350

Gly Gln Gly Thr Thr Leu Thr Val Ser Ser Val Glu Gly Gly Ser Gly
            355                 360                 365

Gly Ser Gly Gly Ser Gly Gly Ser Gly Gly Val Asp Asp Ile Gln Leu
        370                 375                 380

Thr Gln Ser Pro Ala Ile Met Ser Ala Ser Pro Gly Glu Lys Val Thr
385                 390                 395                 400

Met Thr Cys Arg Ala Ser Ser Val Ser Tyr Met Asn Trp Tyr Gln
                405                 410                 415

Gln Lys Ser Gly Thr Ser Pro Lys Arg Trp Ile Tyr Asp Thr Ser Lys
            420                 425                 430

Val Ala Ser Gly Val Pro Tyr Arg Phe Ser Gly Ser Gly Ser Gly Thr
                435                 440                 445

Ser Tyr Ser Leu Thr Ile Ser Ser Met Glu Ala Glu Asp Ala Ala Thr
    450                 455                 460

Tyr Tyr Cys Gln Gln Trp Ser Ser Asn Pro Leu Thr Phe Gly Ala Gly
465                 470                 475                 480

Thr Lys Leu Glu Leu Lys His His His His His
                485                 490

<210> SEQ ID NO 74
<211> LENGTH: 1479
<212> TYPE: DNA
<213> ORGANISM: artificial sequence
<220> FEATURE:
<223> OTHER INFORMATION: scFv EpCAMxCD3 with M13 mutant in anti-CD3 part
```

<400> SEQUENCE: 74

```
gatatccagc tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat tcactctca ccatcagcaa tgtgcagtct      240
gaagacttgg cagagtattt ctgtcagcaa tataacagct atccgctcac gttcggtgct     300
gggaccaagc tcgagatcaa aggtggtggt ggttctggcg gcggcggctc cggtggtggt     360
ggttctcagg tgaaactgca ggagtcagga cctggcctag tgcagccctc acagagcctg     420
tccatcacct gcacagtctc tggtttctca ttaactagct atggtgtaca ctgggttcgc     480
cagtctccag gaaagggtct ggagtggctg gagtgatat ggagtggtgg aagcacagac      540
tataatgcag ctttcatatc cagactgagc atcagcaagg acaattccaa gagccaagtt     600
ttctttaaaa tgaacagtct gcaagctaat gacacagcca tatattactg tgccagaatg     660
gagaactggt cgtttgctta ctggggccaa gggaccacgg tcaccgtctc ctccggaggt     720
ggtggatccg atatcaaact gcagcagtca ggggctgaac tggcaagacc tggggcctca     780
gtgaagatgt cctgcaagac ttctggctac acctttacta ggtacacgat gcactgggta     840
aaacagaggc ctggacaggg tctggaatgg attggataca ttaatcctag ccgtggttat     900
actaattaca atcagaagtt caaggacaag gccacattga ctacagacaa atcctccagc     960
acagcctaca tgcaactgag cagcctgaca tctgaggact ctgcagtcta ttactgtgca    1020
agatattata atgatcaata ctgccttgac tactggggcc aaggcaccac tctcacagtc    1080
tcctcagtcg aaggtggaag tggaggttct ggtggaagtg gaggttcagg tggagtcgac    1140
gacattcagc tgacccagtc tccagcaatc atgtctgcat ctccagggga aaggtcacc     1200
atgacctgca gagccagttc aagtgtaagt tacatgaact ggtaccagca gaagtcaggc    1260
acctccccca aaagatggat ttatgacaca tccaaagtgg cttctggagt cccttatcgc    1320
ttcagtggca gtgggtctgg gacctcatac tctctcacaa tcagcagcat ggaggctgaa    1380
gatgctgcca cttattactg ccaacagtgg agtagtaacc cgctcacgtt cggtgctggg    1440
accaagctgg agctgaaaca tcatcaccat catcattag                           1479
```

<210> SEQ ID NO 75
<211> LENGTH: 492
<212> TYPE: PRT
<213> ORGANISM: artificial sequence
<220> FEATURE:
<223> OTHER INFORMATION: scFv EpCAMxCD3 with M14 mutant in anti-CD3 part

<400> SEQUENCE: 75

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95
```

```
Thr Phe Gly Ala Gly Thr Lys Leu Glu Ile Lys Gly Gly Gly Ser
                100                 105                 110

Gly Gly Gly Gly Ser Gly Gly Gly Gly Ser Gln Val Lys Leu Gln Glu
            115                 120                 125

Ser Gly Pro Gly Leu Val Gln Pro Ser Gln Ser Leu Ser Ile Thr Cys
        130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
        195                 200                 205

Ala Asn Asp Thr Ala Ile Tyr Tyr Cys Ala Arg Met Glu Asn Trp Ser
210                 215                 220

Phe Ala Tyr Trp Gly Gln Gly Thr Thr Val Thr Val Ser Ser Gly Gly
225                 230                 235                 240

Gly Gly Ser Asp Ile Lys Leu Gln Gln Ser Gly Ala Glu Leu Ala Arg
            245                 250                 255

Pro Gly Ala Ser Val Lys Met Ser Cys Lys Thr Ser Gly Tyr Thr Phe
        260                 265                 270

Thr Arg Tyr Thr Met His Trp Val Lys Gln Arg Pro Gly Gln Gly Leu
    275                 280                 285

Glu Trp Ile Gly Tyr Ile Asn Pro Ser Arg Gly Tyr Thr Asn Tyr Asn
290                 295                 300

Gln Lys Phe Lys Asp Lys Ala Thr Leu Thr Thr Asp Lys Ser Ser Ser
305                 310                 315                 320

Thr Ala Tyr Met Gln Leu Ser Ser Leu Thr Ser Glu Asp Ser Ala Val
            325                 330                 335

Tyr Tyr Cys Ala Arg Tyr Tyr Asp Ala His Asn Cys Leu Asp Tyr Trp
        340                 345                 350

Gly Gln Gly Thr Thr Leu Thr Val Ser Ser Val Glu Gly Gly Ser Gly
    355                 360                 365

Gly Ser Gly Gly Ser Gly Gly Ser Gly Gly Val Asp Asp Ile Gln Leu
            370                 375                 380

Thr Gln Ser Pro Ala Ile Met Ser Ala Ser Pro Gly Glu Lys Val Thr
385                 390                 395                 400

Met Thr Cys Arg Ala Ser Ser Ser Val Ser Tyr Met Asn Trp Tyr Gln
                405                 410                 415

Gln Lys Ser Gly Thr Ser Pro Lys Arg Trp Ile Tyr Asp Thr Ser Lys
            420                 425                 430

Val Ala Ser Gly Val Pro Tyr Arg Phe Ser Gly Ser Gly Ser Gly Thr
        435                 440                 445

Ser Tyr Ser Leu Thr Ile Ser Ser Met Glu Ala Glu Asp Ala Ala Thr
    450                 455                 460

Tyr Tyr Cys Gln Gln Trp Ser Ser Asn Pro Leu Thr Phe Gly Ala Gly
465                 470                 475                 480

Thr Lys Leu Glu Leu Lys His His His His His
                485                 490

<210> SEQ ID NO 76
<211> LENGTH: 1479
```

<210> SEQ ID NO 76
<211> LENGTH: 1479
<212> TYPE: DNA
<213> ORGANISM: artificial sequence
<220> FEATURE:
<223> OTHER INFORMATION: scFv EpCAMxCD3 with M14 mutant in anti-CD3 part

<400> SEQUENCE: 76

```
gatatccagc tgacccagtc tcaaaaattc atgtccacat cagtaggaga cagggtcagc    60
gtcacctgca aggccagtca gaatgtgggt actaatgtag cctggtatca acagaaacca   120
gggcaatctc ctaaagcact gatttactcg gcatcctacc ggtacagtgg agtccctgat   180
cgcttcacag gcagtggatc tgggacagat ttcactctca ccatcagcaa tgtgcagtct   240
gaagacttgg cagagtattt ctgtcagcaa tataacagct atccgctcac gttcggtgct   300
gggaccaagc tcgagatcaa aggtggtggt ggttctggcg gcggcggctc cggtggtggt   360
ggttctcagg tgaaactgca ggagtcagga cctggcctag tgcagccctc acagagcctg   420
tccatcacct gcacagtctc tggtttctca ttaactagct atggtgtaca ctgggttcgc   480
cagtctccag gaaagggtct ggagtggctg ggagtgatat ggagtggtgg aagcacagac   540
tataatgcag ctttcatatc cagactgagc atcagcaagg acaattccaa gagccaagtt   600
ttctttaaaa tgaacagtct gcaagctaat gacacagcca tatattactg tgccagaatg   660
gagaactggt cgtttgctta ctggggccaa gggaccacgg tcaccgtctc ctccggaggt   720
ggtggatccg atatcaaact gcagcagtca ggggctgaac tggcaagacc tggggcctca   780
gtgaagatgt cctgcaagac ttctggctac acctttacta ggtacacgat gcactgggta   840
aaacagaggc ctggacaggg tctggaatgg attggataca ttaatcctag ccgtggttat   900
actaattaca atcagaagtt caaggacaag gccacattga ctacagacaa atcctccagc   960
acagcctaca tgcaactgag cagcctgaca tctgaggact ctgcagtcta ttactgtgca  1020
agatattatg atgctcataa ttgccttgac tactggggcc aaggcaccac tctcacagtc  1080
tcctcagtcg aaggtggaag tggaggttct ggtggaagtg gaggttcagg tggagtcgac  1140
gacattcagc tgacccagtc tccagcaatc atgtctgcat ctccagggga aggtcacc    1200
atgacctgca gagccagttc aagtgtaagt tacatgaact ggtaccagca gaagtcaggc  1260
acctccccca aaagatggat ttatgacaca tccaaagtgg cttctggagt cccttatcgc  1320
ttcagtggca gtgggtctgg gacctcatac tctctcacaa tcagcagcat ggaggctgaa  1380
gatgctgcca cttattactg ccaacagtgg agtagtaacc cgctcacgtt cggtgctggg  1440
accaagctgg agctgaaaca tcatcaccat catcattag                         1479
```

<210> SEQ ID NO 77
<211> LENGTH: 492
<212> TYPE: PRT
<213> ORGANISM: artificial sequence
<220> FEATURE:
<223> OTHER INFORMATION: scFv EpCAMxCD3 with M20 mutant in anti-CD3 part

<400> SEQUENCE: 77

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60
```

```
Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Leu
                 85                  90                  95

Thr Phe Gly Ala Gly Thr Lys Leu Glu Ile Lys Gly Gly Gly Gly Ser
            100                 105                 110

Gly Gly Gly Gly Ser Gly Gly Gly Ser Gln Val Lys Leu Gln Glu
            115                 120                 125

Ser Gly Pro Gly Leu Val Gln Pro Ser Gln Ser Leu Ser Ile Thr Cys
130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
            195                 200                 205

Ala Asn Asp Thr Ala Ile Tyr Tyr Cys Ala Arg Met Glu Asn Trp Ser
210                 215                 220

Phe Ala Tyr Trp Gly Gln Gly Thr Thr Val Thr Val Ser Ser Gly Gly
225                 230                 235                 240

Gly Gly Ser Asp Ile Lys Leu Gln Gln Ser Gly Ala Glu Leu Ala Arg
            245                 250                 255

Pro Gly Ala Ser Val Lys Met Ser Cys Lys Thr Ser Gly Tyr Thr Phe
            260                 265                 270

Thr Arg Tyr Thr Met His Trp Val Lys Gln Arg Pro Gly Gln Gly Leu
            275                 280                 285

Glu Trp Ile Gly Tyr Ile Asn Pro Ser Arg Gly Tyr Thr Asn Tyr Asn
    290                 295                 300

Gln Lys Phe Lys Asp Lys Ala Thr Leu Thr Thr Asp Lys Ser Ser Ser
305                 310                 315                 320

Thr Ala Tyr Met Gln Leu Ser Ser Leu Thr Ser Glu Asp Ser Ala Val
                325                 330                 335

Tyr Tyr Cys Ala Arg Tyr His Asp Asp Pro Tyr Cys Leu Asp Tyr Trp
            340                 345                 350

Gly Gln Gly Thr Thr Leu Thr Val Ser Ser Val Glu Gly Gly Ser Gly
            355                 360                 365

Gly Ser Gly Gly Ser Gly Gly Ser Gly Gly Val Asp Asp Ile Gln Leu
            370                 375                 380

Thr Gln Ser Pro Ala Ile Met Ser Ala Ser Pro Gly Glu Lys Val Thr
385                 390                 395                 400

Met Thr Cys Arg Ala Ser Ser Ser Val Ser Tyr Met Asn Trp Tyr Gln
                405                 410                 415

Gln Lys Ser Gly Thr Ser Pro Lys Arg Trp Ile Tyr Asp Thr Ser Lys
            420                 425                 430

Val Ala Ser Gly Val Pro Tyr Arg Phe Ser Gly Ser Gly Ser Gly Thr
            435                 440                 445

Ser Tyr Ser Leu Thr Ile Ser Ser Met Glu Ala Glu Asp Ala Ala Thr
            450                 455                 460

Tyr Tyr Cys Gln Gln Trp Ser Ser Asn Pro Leu Thr Phe Gly Ala Gly
465                 470                 475                 480

Thr Lys Leu Glu Leu Lys His His His His His His
```

<210> SEQ ID NO 78
<211> LENGTH: 1479
<212> TYPE: DNA
<213> ORGANISM: artificial sequence
<220> FEATURE:
<223> OTHER INFORMATION: scFv EpCAMxCD3 with M20 mutant in anti-CD3 part

<400> SEQUENCE: 78

```
gatatccagc tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgctcac gttcggtgct     300
gggaccaagc tcgagatcaa aggtggtggt ggttctggcg gcggcggctc cggtggtggt     360
ggttctcagg tgaaactgca ggagtcagga cctggcctag tgcagccctc acagagcctg     420
tccatcacct gcacagtctc tggtttctca ttaactagct atggtgtaca ctgggttcgc     480
cagtctccag gaaagggtct ggagtggctg ggagtgatat ggagtggtgg aagcacagac     540
tataatgcag ctttcatatc agactgagc atcagcaagg acaattccaa gagccaagtt     600
ttctttaaaa tgaacagtct gcaagctaat gacacagcca tatattactg tgccagaatg     660
gagaactggt cgtttgctta ctggggccaa gggaccacgg tcaccgtctc ctccggaggt     720
ggtggatccg atatcaaact gcagcagtca ggggctgaac tggcaagacc tggggcctca     780
gtgaagatgt cctgcaagac ttctggctac acctttacta ggtacacgat gcactgggta     840
aaacagaggc ctggacaggg tctggaatgg attggataca ttaatcctag ccgtggttat     900
actaattaca atcagaagtt caaggacaag gccacattga ctacagacaa atcctccagc     960
acagcctaca tgcaactgag cagcctgaca tctgaggact ctgcagtcta ttactgtgca    1020
agatatcatg atgatccata ctgccttgac tactggggcc aaggcaccac tctcacagtc    1080
tcctcagtcg aaggtggaag tggaggttct ggtggaagtg gaggttcagg tggagtcgac    1140
gacattcagc tgacccagtc tccagcaatc atgtctgcat ctccagggga aaggtcacc    1200
atgacctgca gagccagttc aagtgtaagt tacatgaact ggtaccagca gaagtcaggc    1260
acctccccca aaagatggat ttatgacaca tccaaagtgg cttctggagt cccttatcgc    1320
ttcagtggca gtgggtctgg gacctcatac tctctcacaa tcagcagcat ggaggctgaa    1380
gatgctgcca cttattactg ccaacagtgg agtagtaacc cgctcacgtt cggtgctggg    1440
accaagctgg agctgaaaca tcatcaccat catcattag                          1479
```

<210> SEQ ID NO 79
<211> LENGTH: 492
<212> TYPE: PRT
<213> ORGANISM: artificial sequence
<220> FEATURE:
<223> OTHER INFORMATION: scFv EpCAMxCD3 with M31 mutant in anti-CD3 part

<400> SEQUENCE: 79

Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile

```
                35                  40                  45
Tyr Ser Ala Ser Tyr Arg Tyr Ser Gly Val Pro Asp Arg Phe Thr Gly
 50                  55                  60
Ser Gly Ser Gly Thr Asp Phe Thr Leu Thr Ile Ser Asn Val Gln Ser
 65                  70                  75                  80
Glu Asp Leu Ala Glu Tyr Phe Cys Gln Gln Tyr Asn Ser Tyr Pro Leu
                 85                  90                  95
Thr Phe Gly Ala Gly Thr Lys Leu Glu Ile Lys Gly Gly Gly Gly Ser
                100                 105                 110
Gly Gly Gly Gly Ser Gly Gly Gly Ser Gln Val Lys Leu Gln Glu
            115                 120                 125
Ser Gly Pro Gly Leu Val Gln Pro Ser Gln Ser Leu Ser Ile Thr Cys
130                 135                 140
Thr Val Ser Gly Phe Ser Leu Thr Ser Tyr Gly Val His Trp Val Arg
145                 150                 155                 160
Gln Ser Pro Gly Lys Gly Leu Glu Trp Leu Gly Val Ile Trp Ser Gly
                165                 170                 175
Gly Ser Thr Asp Tyr Asn Ala Ala Phe Ile Ser Arg Leu Ser Ile Ser
            180                 185                 190
Lys Asp Asn Ser Lys Ser Gln Val Phe Phe Lys Met Asn Ser Leu Gln
            195                 200                 205
Ala Asn Asp Thr Ala Ile Tyr Tyr Cys Ala Arg Met Glu Asn Trp Ser
210                 215                 220
Phe Ala Tyr Trp Gly Gln Gly Thr Thr Val Thr Val Ser Ser Gly Gly
225                 230                 235                 240
Gly Gly Ser Asp Ile Lys Leu Gln Gln Ser Gly Ala Glu Leu Ala Arg
            245                 250                 255
Pro Gly Ala Ser Val Lys Met Ser Cys Lys Thr Ser Gly Tyr Thr Phe
            260                 265                 270
Thr Arg Tyr Thr Met His Trp Val Lys Gln Arg Pro Gly Gln Gly Leu
            275                 280                 285
Glu Trp Ile Gly Tyr Ile Asn Pro Ser Arg Gly Tyr Thr Asn Tyr Asn
290                 295                 300
Gln Lys Phe Lys Asp Lys Ala Thr Leu Thr Thr Asp Lys Ser Ser Ser
305                 310                 315                 320
Thr Ala Tyr Met Gln Leu Ser Ser Leu Thr Ser Glu Asp Ser Ala Val
                325                 330                 335
Tyr Tyr Cys Ala Arg Tyr Tyr Glu Gly Arg Tyr Cys Leu Asp Tyr Trp
            340                 345                 350
Gly Gln Gly Thr Thr Leu Thr Val Ser Ser Val Glu Gly Gly Ser Gly
            355                 360                 365
Gly Ser Gly Gly Ser Gly Gly Ser Gly Gly Val Asp Asp Ile Gln Leu
        370                 375                 380
Thr Gln Ser Pro Ala Ile Met Ser Ala Ser Pro Gly Glu Lys Val Thr
385                 390                 395                 400
Met Thr Cys Arg Ala Ser Ser Ser Val Ser Tyr Met Asn Trp Tyr Gln
                405                 410                 415
Gln Lys Ser Gly Thr Ser Pro Lys Arg Trp Ile Tyr Asp Thr Ser Lys
            420                 425                 430
Val Ala Ser Gly Val Pro Tyr Arg Phe Ser Gly Ser Gly Ser Gly Thr
            435                 440                 445
Ser Tyr Ser Leu Thr Ile Ser Ser Met Glu Ala Glu Asp Ala Ala Thr
450                 455                 460
```

Tyr Tyr Cys Gln Gln Trp Ser Ser Asn Pro Leu Thr Phe Gly Ala Gly
465                 470                 475                 480

Thr Lys Leu Glu Leu Lys His His His His His
            485                 490

<210> SEQ ID NO 80
<211> LENGTH: 1479
<212> TYPE: DNA
<213> ORGANISM: artificial sequence
<220> FEATURE:
<223> OTHER INFORMATION: scFv EpCAMxCD3 with M31 mutant in anti-CD3 part

<400> SEQUENCE: 80

| | | | | | |
|---|---|---|---|---|---|
| gatatccagc | tgacccagtc | tcaaaaattc | atgtccacat | cagtaggaga | cagggtcagc | 60 |
| gtcacctgca | aggccagtca | gaatgtgggt | actaatgtag | cctggtatca | acagaaacca | 120 |
| gggcaatctc | ctaaagcact | gatttactcg | gcatcctacc | ggtacagtgg | agtccctgat | 180 |
| cgcttcacag | gcagtggatc | tgggacagat | ttcactctca | ccatcagcaa | tgtgcagtct | 240 |
| gaagacttgg | cagagtattt | ctgtcagcaa | tataacagct | atccgctcac | gttcggtgct | 300 |
| gggaccaagc | tcgagatcaa | aggtggtggt | ggttctggcg | gcggcggctc | cggtggtggt | 360 |
| ggttctcagg | tgaaactgca | ggagtcagga | cctggcctag | tgcagccctc | acagagcctg | 420 |
| tccatcacct | gcacagtctc | tggtttctca | ttaactagct | atggtgtaca | ctgggttcgc | 480 |
| cagtctccag | gaaagggtct | ggagtggctg | ggagtgatat | ggagtggtgg | aagcacagac | 540 |
| tataatgcag | ctttcatatc | cagactgagc | atcagcaagg | acaattccaa | gagccaagtt | 600 |
| ttctttaaaa | tgaacagtct | gcaagctaat | gacacagcca | tatattactg | tgccagaatg | 660 |
| gagaactggt | cgtttgctta | ctggggccaa | gggaccacgg | tcaccgtctc | ctccggaggt | 720 |
| ggtggatccg | atatcaaact | gcagcagtca | ggggctgaac | tggcaagacc | tggggcctca | 780 |
| gtgaagatgt | cctgcaagac | ttctggctac | acctttacta | ggtacacgat | gcactgggta | 840 |
| aaacagaggc | ctggacaggg | tctggaatgg | attggataca | ttaatcctag | ccgtggttat | 900 |
| actaattaca | atcagaagtt | caaggacaag | gccacattga | ctacagacaa | atcctccagc | 960 |
| acagcctaca | tgcaactgag | cagcctgaca | tctgaggact | ctgcagtcta | ttactgtgca | 1020 |
| agatattatg | atgatcatta | ctgccttgac | tactggggcc | aaggcaccac | tctcacagtc | 1080 |
| tcctcagtcg | aaggtggaag | tggaggttct | ggtggaagtg | gaggttcagg | tggagtcgac | 1140 |
| gacattcagc | tgacccagtc | tccagcaatc | atgtctgcat | ctccagggga | gaaggtcacc | 1200 |
| atgacctgca | gagccagttc | aagtgtaagt | tacatgaact | ggtaccagca | gaagtcaggc | 1260 |
| acctccccca | aaagatggat | ttatgacaca | tccaaagtgg | cttctggagt | cccttatcgc | 1320 |
| ttcagtggca | gtgggtctgg | gacctcatac | tctctcacaa | tcagcagcat | ggaggctgaa | 1380 |
| gatgctgcca | cttattactg | ccaacagtgg | agtagtaacc | cgctcacgtt | cggtgctggg | 1440 |
| accaagctgg | agctgaaaca | tcatcaccat | catcattag | | | 1479 |

<210> SEQ ID NO 81
<211> LENGTH: 492
<212> TYPE: PRT
<213> ORGANISM: artificial sequence
<220> FEATURE:
<223> OTHER INFORMATION: scFv EpCAMxCD3 with M58 mutant in anti-CD3 part

<400> SEQUENCE: 81

Asp Ile Gln Leu Thr Gln Ser Gln Lys Phe Met Ser Thr Ser Val Gly
1               5                   10                  15

-continued

```
Asp Arg Val Ser Val Thr Cys Lys Ala Ser Gln Asn Val Gly Thr Asn
            20                  25                  30
Val Ala Trp Tyr Gln Gln Lys Pro Gly Gln Ser Pro Lys Ala Leu Ile
        35                  40                  45
Tyr Ser Ala Ser Tyr Arg Tyr Ser Gly Val Pro Asp Arg Phe Thr Gly
    50                  55                  60
Ser Gly Ser Gly Thr Asp Phe Thr Leu Thr Ile Ser Asn Val Gln Ser
65                  70                  75                  80
Glu Asp Leu Ala Glu Tyr Phe Cys Gln Gln Tyr Asn Ser Tyr Pro Leu
                85                  90                  95
Thr Phe Gly Ala Gly Thr Lys Leu Glu Ile Lys Gly Gly Gly Gly Ser
            100                 105                 110
Gly Gly Gly Gly Ser Gly Gly Gly Ser Gln Val Lys Leu Gln Glu
        115                 120                 125
Ser Gly Pro Gly Leu Val Gln Pro Ser Gln Ser Leu Ser Ile Thr Cys
    130                 135                 140
Thr Val Ser Gly Phe Ser Leu Thr Ser Tyr Gly Val His Trp Val Arg
145                 150                 155                 160
Gln Ser Pro Gly Lys Gly Leu Glu Trp Leu Gly Val Ile Trp Ser Gly
                165                 170                 175
Gly Ser Thr Asp Tyr Asn Ala Ala Phe Ile Ser Arg Leu Ser Ile Ser
            180                 185                 190
Lys Asp Asn Ser Lys Ser Gln Val Phe Phe Lys Met Asn Ser Leu Gln
        195                 200                 205
Ala Asn Asp Thr Ala Ile Tyr Tyr Cys Ala Arg Met Glu Asn Trp Ser
    210                 215                 220
Phe Ala Tyr Trp Gly Gln Gly Thr Thr Val Thr Val Ser Ser Gly Gly
225                 230                 235                 240
Gly Gly Ser Asp Ile Lys Leu Gln Gln Ser Gly Ala Glu Leu Ala Arg
                245                 250                 255
Pro Gly Ala Ser Val Lys Met Ser Cys Lys Thr Ser Gly Tyr Thr Phe
            260                 265                 270
Thr Arg Tyr Thr Met His Trp Val Lys Gln Arg Pro Gly Gln Gly Leu
        275                 280                 285
Glu Trp Ile Gly Tyr Ile Asn Pro Ser Arg Gly Tyr Thr Asn Tyr Asn
    290                 295                 300
Gln Lys Phe Lys Asp Lys Ala Thr Leu Thr Thr Asp Lys Ser Ser Ser
305                 310                 315                 320
Thr Ala Tyr Met Gln Leu Ser Ser Leu Thr Ser Glu Asp Ser Ala Val
                325                 330                 335
Tyr Tyr Cys Ala Arg Tyr Ser Asp Val Tyr Tyr Cys Leu Asp Tyr Trp
            340                 345                 350
Gly Gln Gly Thr Thr Leu Thr Val Ser Ser Val Glu Gly Gly Ser Gly
        355                 360                 365
Gly Ser Gly Gly Ser Gly Gly Ser Gly Gly Val Asp Asp Ile Gln Leu
    370                 375                 380
Thr Gln Ser Pro Ala Ile Met Ser Ala Ser Pro Gly Glu Lys Val Thr
385                 390                 395                 400
Met Thr Cys Arg Ala Ser Ser Ser Val Ser Tyr Met Asn Trp Tyr Gln
                405                 410                 415
Gln Lys Ser Gly Thr Ser Pro Lys Arg Trp Ile Tyr Asp Thr Ser Lys
            420                 425                 430
```

Val Ala Ser Gly Val Pro Tyr Arg Phe Ser Gly Ser Gly Ser Gly Thr
         435                 440                 445

Ser Tyr Ser Leu Thr Ile Ser Ser Met Glu Ala Glu Asp Ala Ala Thr
         450                 455                 460

Tyr Tyr Cys Gln Gln Trp Ser Ser Asn Pro Leu Thr Phe Gly Ala Gly
465                 470                 475                 480

Thr Lys Leu Glu Leu Lys His His His His His His
                485                 490

<210> SEQ ID NO 82
<211> LENGTH: 1479
<212> TYPE: DNA
<213> ORGANISM: artificial sequence
<220> FEATURE:
<223> OTHER INFORMATION: scFv EpCAMxCD3 with M58 mutant in anti-CD3 part

<400> SEQUENCE: 82

```
gatatccagc tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgctcac gttcggtgct     300
gggaccaagc tcgagatcaa aggtggtggt ggttctggcg gcggcggctc cggtggtggt     360
ggttctcagg tgaaactgca ggagtcagga cctggcctag tgcagccctc acagagcctg     420
tccatcacct gcacagtctc tggtttctca ttaactagct atggtgtaca ctgggttcgc     480
cagtctccag gaaagggtct ggagtggctg gagtgatat ggagtggtgg aagcacagac     540
tataatgcag ctttcatatc cagactgagc atcagcaagg acaattccaa gagccaagtt     600
ttctttaaaa tgaacagtct gcaagctaat gacacagcca tatattactg tgccagaatg     660
gagaactggt cgtttgctta ctggggccaa gggaccacgg tcaccgtctc ctccggaggt     720
ggtggatccg atatcaaact gcagcagtca ggggctgaac tggcaagacc tggggcctca     780
gtgaagatgt cctgcaagac ttctggctac acctttacta ggtacacgat gcactgggta     840
aaacagaggc ctggacaggg tctggaatgg attggataca ttaatcctag ccgtggttat     900
actaattaca atcagaagtt caaggacaag gccacattga ctacagacaa atcctccagc     960
acagcctaca tgcaactgag cagcctgaca tctgaggact ctgcagtcta ttactgtgca    1020
agatattctg atgtttatta ctgccttgac tactggggcc aaggcaccac tctcacagtc    1080
tcctcagtcg aaggtggaag tggaggttct ggtggaagtg gaggttcagg tggagtcgac    1140
gacattcagc tgacccagtc tccagcaatc atgtctgcat ctccagggga aaggtcacc    1200
atgacctgca gagccagttc aagtgtaagt tacatgaact ggtaccagca gaagtcaggc    1260
acctccccca aaagatggat ttatgacaca tccaaagtgg cttctggagt cccttatcgc    1320
ttcagtggca gtgggtctgg gacctcatac tctctcacaa tcagcagcat ggaggctgaa    1380
gatgctgcca cttattactg ccaacagtgg agtagtaacc cgctcacgtt cggtgctggg    1440
accaagctgg agctgaaaca tcatcaccat catcattag                             1479
```

<210> SEQ ID NO 83
<211> LENGTH: 492
<212> TYPE: PRT
<213> ORGANISM: artificial sequence
<220> FEATURE:
<223> OTHER INFORMATION: scFv EpCAMxCD3 with M65 mutant in anti-CD3 part

<400> SEQUENCE: 83

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Gly Gly Gly Gly Ser
            100                 105                 110

Gly Gly Gly Gly Ser Gly Gly Gly Ser Gln Val Lys Leu Gln Glu
        115                 120                 125

Ser Gly Pro Gly Leu Val Gln Pro Ser Gln Ser Leu Ser Ile Thr Cys
    130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
        195                 200                 205

Ala Asn Asp Thr Ala Ile Tyr Tyr Cys Ala Arg Met Glu Asn Trp Ser
    210                 215                 220

Phe Ala Tyr Trp Gly Gln Gly Thr Thr Val Thr Val Ser Ser Gly Gly
225                 230                 235                 240

Gly Gly Ser Asp Ile Lys Leu Gln Gln Ser Gly Ala Glu Leu Ala Arg
                245                 250                 255

Pro Gly Ala Ser Val Lys Met Ser Cys Lys Thr Ser Gly Tyr Thr Phe
            260                 265                 270

Thr Arg Tyr Thr Met His Trp Val Lys Gln Arg Pro Gly Gln Gly Leu
        275                 280                 285

Glu Trp Ile Gly Tyr Ile Asn Pro Ser Arg Gly Tyr Thr Asn Tyr Asn
    290                 295                 300

Gln Lys Phe Lys Asp Lys Ala Thr Leu Thr Thr Asp Lys Ser Ser Ser
305                 310                 315                 320

Thr Ala Tyr Met Gln Leu Ser Ser Leu Thr Ser Glu Asp Ser Ala Val
                325                 330                 335

Tyr Tyr Cys Ala Arg Tyr Ser Asp Asp Arg Tyr Cys Leu Asp Tyr Trp
            340                 345                 350

Gly Gln Gly Thr Thr Leu Thr Val Ser Ser Val Glu Gly Gly Ser Gly
        355                 360                 365

Gly Ser Gly Gly Ser Gly Gly Ser Gly Gly Val Asp Asp Ile Gln Leu
    370                 375                 380

Thr Gln Ser Pro Ala Ile Met Ser Ala Ser Pro Gly Glu Lys Val Thr
385                 390                 395                 400

Met Thr Cys Arg Ala Ser Ser Ser Val Ser Tyr Met Asn Trp Tyr Gln
```

-continued

```
                    405                 410                 415
Gln Lys Ser Gly Thr Ser Pro Lys Arg Trp Ile Tyr Asp Thr Ser Lys
                420                 425                 430

Val Ala Ser Gly Val Pro Tyr Arg Phe Ser Gly Ser Gly Ser Gly Thr
            435                 440                 445

Ser Tyr Ser Leu Thr Ile Ser Ser Met Glu Ala Glu Asp Ala Ala Thr
        450                 455                 460

Tyr Tyr Cys Gln Gln Trp Ser Ser Asn Pro Leu Thr Phe Gly Ala Gly
465                 470                 475                 480

Thr Lys Leu Glu Leu Lys His His His His His His
                485                 490
```

<210> SEQ ID NO 84
<211> LENGTH: 1479
<212> TYPE: DNA
<213> ORGANISM: artificial sequence
<220> FEATURE:
<223> OTHER INFORMATION: scFv EpCAMxCD3 with M65 mutant in anti-CD3 part

<400> SEQUENCE: 84

| | |
|---|---|
| gatatccagc tgacccagtc tcaaaaattc atgtccacat cagtaggaga cagggtcagc | 60 |
| gtcacctgca aggccagtca gaatgtgggt actaatgtag cctggtatca acagaaacca | 120 |
| gggcaatctc ctaaagcact gatttactcg catcctacc ggtacagtgg agtccctgat | 180 |
| cgcttcacag gcagtggatc tgggacagat tcactctca ccatcagcaa tgtgcagtct | 240 |
| gaagacttgg cagagtattt ctgtcagcaa tataacagct atccgctcac gttcggtgct | 300 |
| gggaccaagc tcgagatcaa aggtggtggt ggttctggcg gcggcggctc cggtggtggt | 360 |
| ggttctcagg tgaaactgca ggagtcagga cctggcctag tgcagccctc acagagcctg | 420 |
| tccatcacct gcacagtctc tggtttctca ttaactagct atggtgtaca ctgggttcgc | 480 |
| cagtctccag gaaagggtct ggagtggctg ggagtgatat ggagtggtgg aagcacagac | 540 |
| tataatgcag ctttcatatc cagactgagc atcagcaagg acaattccaa gagccaagtt | 600 |
| ttctttaaaa tgaacagtct gcaagctaat gacacagcca tatattactg tgccagaatg | 660 |
| gagaactggt cgtttgctta ctggggccaa gggaccacgg tcaccgtctc ctccggaggt | 720 |
| ggtggatccg atatcaaact gcagcagtca ggggctgaac tggcaagacc tggggcctca | 780 |
| gtgaagatgt cctgcaagac ttctggctac acctttacta ggtacacgat gcactgggta | 840 |
| aaacagaggc ctggacaggg tctggaatgg attggataca ttaatcctag ccgtggttat | 900 |
| actaattaca atcagaagtt caaggacaag gccacattga ctacagacaa atcctccagc | 960 |
| acagcctaca tgcaactgag cagcctgaca tctgaggact ctgcagtcta ttactgtgca | 1020 |
| agatattctg atgatcgtta ctgccttgac tactggggcc aaggcaccac tctcacagtc | 1080 |
| tcctcagtcg aaggtggaag tggaggttct ggtggaagtg gaggttcagg tggagtcgac | 1140 |
| gacattcagc tgacccagtc tccagcaatc atgtctgcat ctccagggga aaggtcacc | 1200 |
| atgacctgca gagccagttc aagtgtaagt tacatgaact ggtaccagca gaagtcaggc | 1260 |
| acctccccca aaagatggat ttatgacaca tccaaagtgg cttctggagt cccttatcgc | 1320 |
| ttcagtggca gtgggtctgg gacctcatac tctctcacaa tcagcagcat ggaggctgaa | 1380 |
| gatgctgcca cttattactg ccaacagtgg agtagtaacc cgctcacgtt cggtgctggg | 1440 |
| accaagctgg agctgaaaca tcatcaccat catcattag | 1479 |

<210> SEQ ID NO 85

<211> LENGTH: 492
<212> TYPE: PRT
<213> ORGANISM: artificial sequence
<220> FEATURE:
<223> OTHER INFORMATION: scFv EpCAMxCD3 with M69 mutant in anti-CD3 part

<400> SEQUENCE: 85

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Gly Gly Gly Gly Ser
            100                 105                 110

Gly Gly Gly Gly Ser Gly Gly Gly Ser Gln Val Lys Leu Gln Glu
        115                 120                 125

Ser Gly Pro Gly Leu Val Gln Pro Ser Gln Ser Leu Ser Ile Thr Cys
    130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
        195                 200                 205

Ala Asn Asp Thr Ala Ile Tyr Tyr Cys Ala Arg Met Glu Asn Trp Ser
    210                 215                 220

Phe Ala Tyr Trp Gly Gln Gly Thr Thr Val Thr Val Ser Ser Gly Gly
225                 230                 235                 240

Gly Gly Ser Asp Ile Lys Leu Gln Gln Ser Gly Ala Glu Leu Ala Arg
                245                 250                 255

Pro Gly Ala Ser Val Lys Met Ser Cys Lys Thr Ser Gly Tyr Thr Phe
            260                 265                 270

Thr Arg Tyr Thr Met His Trp Val Lys Gln Arg Pro Gly Gln Gly Leu
        275                 280                 285

Glu Trp Ile Gly Tyr Ile Asn Pro Ser Arg Gly Tyr Thr Asn Tyr Asn
    290                 295                 300

Gln Lys Phe Lys Asp Lys Ala Thr Leu Thr Thr Asp Lys Ser Ser Ser
305                 310                 315                 320

Thr Ala Tyr Met Gln Leu Ser Ser Leu Thr Ser Glu Asp Ser Ala Val
                325                 330                 335

Tyr Tyr Cys Ala Arg Tyr Asn Asp His Tyr Cys Leu Asp Tyr Trp
            340                 345                 350

Gly Gln Gly Thr Thr Leu Thr Val Ser Ser Val Glu Gly Gly Ser Gly
        355                 360                 365

Gly Ser Gly Gly Ser Gly Gly Ser Gly Gly Val Asp Asp Ile Gln Leu
    370                 375                 380
```

```
Thr Gln Ser Pro Ala Ile Met Ser Ala Ser Pro Gly Glu Lys Val Thr
385                 390                 395                 400

Met Thr Cys Arg Ala Ser Ser Val Ser Tyr Met Asn Trp Tyr Gln
            405                 410                 415

Gln Lys Ser Gly Thr Ser Pro Lys Arg Trp Ile Tyr Asp Thr Ser Lys
            420                 425                 430

Val Ala Ser Gly Val Pro Tyr Arg Phe Ser Gly Ser Gly Ser Gly Thr
            435                 440                 445

Ser Tyr Ser Leu Thr Ile Ser Ser Met Glu Ala Glu Asp Ala Ala Thr
        450                 455                 460

Tyr Tyr Cys Gln Gln Trp Ser Ser Asn Pro Leu Thr Phe Gly Ala Gly
465             470                 475                 480

Thr Lys Leu Glu Leu Lys His His His His His His
            485                 490
```

<210> SEQ ID NO 86
<211> LENGTH: 1479
<212> TYPE: DNA
<213> ORGANISM: artificial sequence
<220> FEATURE:
<223> OTHER INFORMATION: scFv EpCAMxCD3 with M69 mutant in anti-CD3 part

<400> SEQUENCE: 86

```
gatatccagc tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgctcac gttcggtgct     300
gggaccaagc tcgagatcaa aggtggtggt ggttctggcg gcggcggctc cggtggtggt     360
ggttctcagg tgaaactgca ggagtcagga cctggcctag tgcagccctc acagagcctg     420
tccatcacct gcacagtctc tggtttctca ttaactagct atggtgtaca ctgggttcgc     480
cagtctccag gaaagggtct ggagtggctg ggagtgatat ggagtggtgg aagcacagac     540
tataatgcag ctttcatatc agactgagc atcagcaagg acaattccaa gagccaagtt     600
ttctttaaaa tgaacagtct gcaagctaat gacacagcca tatattactg tgccagaatg     660
gagaactggt cgtttgctta ctggggccaa gggaccacgg tcaccgtctc ctccggaggt     720
ggtggatccg atatcaaact gcagcagtca ggggctgaac tggcaagacc tggggcctca     780
gtgaagatgt cctgcaagac ttctggctac acctttacta ggtacacgat gcactgggta     840
aaacagaggc ctggacaggg tctggaatgg attggataca ttaatcctag ccgtggttat     900
actaattaca atcagaagtt caaggacaag gccacattga ctacagacaa atcctccagc     960
acagcctaca tgcaactgag cagcctgaca tctgaggact ctgcagtcta ttactgtgca    1020
agatataatg atgaacatta ctgccttgac tactggggcc aaggcaccac tctcacagtc    1080
tcctcagtcg aaggtggaag tggaggttct ggtggaagtg gaggttcagg tggagtcgac    1140
gacattcagc tgacccagtc tccagcaatc atgtctgcat ctccagggga aggtcacc     1200
atgacctgca gagccagttc aagtgtaagt tacatgaact ggtaccagca gaagtcaggc    1260
acctccccca aagatggat ttatgacaca tccaaagtgg cttctggagt cccttatcgc    1320
ttcagtggca gtgggtctgg gacctcatac tctctcacaa tcagcagcat ggaggctgaa    1380
gatgctgcca cttattactg ccaacagtgg agtagtaacc cgctcacgtt cggtgctggg    1440
```

```
accaagctgg agctgaaaca tcatcaccat catcattag                     1479
```

<210> SEQ ID NO 87
<211> LENGTH: 492
<212> TYPE: PRT
<213> ORGANISM: artificial sequence
<220> FEATURE:
<223> OTHER INFORMATION: scFv EpCAMxCD3 with M76 mutant in anti-CD3 part

<400> SEQUENCE: 87

```
Asp Ile Gln Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys Gly Gly Gly Gly Ser
            100                 105                 110

Gly Gly Gly Gly Ser Gly Gly Gly Ser Gln Val Lys Leu Gln Glu
        115                 120                 125

Ser Gly Pro Gly Leu Val Gln Pro Ser Gln Ser Leu Ser Ile Thr Cys
    130                 135                 140

Thr Val Ser Gly Phe Ser Leu Thr Ser Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Ser Thr Asp Tyr Asn Ala Ala Phe Ile Ser Arg Leu Ser Ile Ser
            180                 185                 190

Lys Asp Asn Ser Lys Ser Gln Val Phe Phe Lys Met Asn Ser Leu Gln
        195                 200                 205

Ala Asn Asp Thr Ala Ile Tyr Tyr Cys Ala Arg Met Glu Asn Trp Ser
    210                 215                 220

Phe Ala Tyr Trp Gly Gln Gly Thr Thr Val Thr Val Ser Ser Gly Gly
225                 230                 235                 240

Gly Gly Ser Asp Ile Lys Leu Gln Gln Ser Gly Ala Glu Leu Ala Arg
                245                 250                 255

Pro Gly Ala Ser Val Lys Met Ser Cys Lys Thr Ser Gly Tyr Thr Phe
            260                 265                 270

Thr Arg Tyr Thr Met His Trp Val Lys Gln Arg Pro Gly Gln Gly Leu
        275                 280                 285

Glu Trp Ile Gly Tyr Ile Asn Pro Ser Arg Gly Tyr Thr Asn Tyr Asn
    290                 295                 300

Gln Lys Phe Lys Asp Lys Ala Thr Leu Thr Thr Asp Lys Ser Ser Ser
305                 310                 315                 320

Thr Ala Tyr Met Gln Leu Ser Ser Leu Thr Ser Glu Asp Ser Ala Val
                325                 330                 335

Tyr Tyr Cys Ala Arg Tyr Tyr Asp Asp His Tyr Cys Leu Asp Tyr Trp
            340                 345                 350
```

-continued

```
Gly Gln Gly Thr Thr Leu Thr Val Ser Ser Val Glu Gly Gly Ser Gly
        355                 360                 365
Gly Ser Gly Gly Ser Gly Gly Ser Gly Gly Val Asp Asp Ile Gln Leu
    370                 375                 380
Thr Gln Ser Pro Ala Ile Met Ser Ala Ser Pro Gly Glu Lys Val Thr
385                 390                 395                 400
Met Thr Cys Arg Ala Ser Ser Val Ser Tyr Met Asn Trp Tyr Gln
                405                 410                 415
Gln Lys Ser Gly Thr Ser Pro Lys Arg Trp Ile Tyr Asp Thr Ser Lys
            420                 425                 430
Val Ala Ser Gly Val Pro Tyr Arg Phe Ser Gly Ser Gly Ser Gly Thr
        435                 440                 445
Ser Tyr Ser Leu Thr Ile Ser Ser Met Glu Ala Glu Asp Ala Ala Thr
    450                 455                 460
Tyr Tyr Cys Gln Gln Trp Ser Ser Asn Pro Leu Thr Phe Gly Ala Gly
465                 470                 475                 480
Thr Lys Leu Glu Leu Lys His His His His His His
                485                 490
```

<210> SEQ ID NO 88
<211> LENGTH: 1479
<212> TYPE: DNA
<213> ORGANISM: artificial sequence
<220> FEATURE:
<223> OTHER INFORMATION: scFv EpCAMxCD3 with M76 mutant in anti-CD3 part

<400> SEQUENCE: 88

```
gatatccagc tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgctcac gttcggtgct     300
gggaccaagc tcgagatcaa aggtggtggt ggttctggcg gcggcggctc cggtggtggt     360
ggttctcagg tgaaactgca ggagtcagga cctggcctag tgcagccctc acagagcctg     420
tccatcacct gcacagtctc tggtttctca ttaactagct atggtgtaca ctgggttcgc     480
cagtctccag gaaagggtct ggagtggctg ggagtgatat ggagtggtgg aagcacagac     540
tataatgcag ctttcatatc agactgagc atcagcaagg acaattccaa gagccaagtt     600
ttctttaaaa tgaacagtct gcaagctaat gacacagcca tatattactg tccagaatg     660
gagaactggt cgtttgctta ctggggccaa gggaccacgg tcaccgtctc ctccggaggt     720
ggtggatccg atatcaaact gcagcagtca ggggctgaac tggcaagacc tggggcctca     780
gtgaagatgt cctgcaagac ttctggctac acctttacta ggtacacgat gcactgggta     840
aaacagaggc ctggacaggg tctggaatgg attggataca ttaatcctag ccgtggttat     900
actaattaca atcagaagtt caaggacaag gccacattga ctacagacaa atcctccagc     960
acagcctaca tgcaactgag cagcctgaca tctgaggact ctgcagtcta ttactgtgca    1020
agatattatg atgataatta ctgccttgac tactggggcc aaggcaccac tctcacagtc    1080
tcctcagtcg aaggtggaag tggaggttct ggtggaagtg aggttcagg tggagtcgac    1140
gacattcagc tgacccagtc tccagcaatc atgtctgcat ctccagggga gaaggtcacc    1200
atgacctgca gagccagttc aagtgtaagt tacatgaact ggtaccagca gaagtcaggc    1260
```

-continued

```
acctccccca aaagatggat ttatgacaca tccaaagtgg cttctggagt ccctta tcgc    1320 ttcagtggca gtgggtctgg gacctcatac tctctcacaa tcagcagcat ggaggctgaa    1380
gatgctgcca cttattactg ccaacagtgg agtagtaacc cgctcacgtt cggtgctggg    1440
accaagctgg agctgaaaca tcatcaccat catcattag                           1479
```

<210> SEQ ID NO 89
<211> LENGTH: 18
<212> TYPE: DNA
<213> ORGANISM: artificial sequence
<220> FEATURE:
<223> OTHER INFORMATION: CDR3 anti-CD3 heavy chain

<400> SEQUENCE: 89

```
tattatgatg atcattac                                                    18
```